US012303471B2

(12) United States Patent
Narain et al.

(10) Patent No.: US 12,303,471 B2
(45) Date of Patent: May 20, 2025

(54) METHODS OF TREATMENT OF TEMOZOLOMIDE-RESISTANT GLIOMA USING COENZYME Q10

(71) Applicant: BPGbio, Inc., Framingham, MA (US)

(72) Inventors: Niven Rajin Narain, Cambridge, MA (US); Rangaprasad Sarangarajan, Boylston, MA (US); Vivek K. Vishnudas, Bedford, MA (US); Anne R. Diers, Wilmington, MA (US); Stephane Gesta, Concord, MA (US)

(73) Assignee: BPGbio, Inc., Framingham, MA (US)

( * ) Notice: Subject to any disclaimer, the term of this patent is extended or adjusted under 35 U.S.C. 154(b) by 0 days.

(21) Appl. No.: 17/572,092

(22) Filed: Jan. 10, 2022

(65) Prior Publication Data

US 2022/0202741 A1    Jun. 30, 2022

Related U.S. Application Data

(63) Continuation of application No. 15/353,724, filed on Nov. 16, 2016, now abandoned.

(60) Provisional application No. 62/256,107, filed on Nov. 16, 2015.

(51) Int. Cl.
| | | |
|---|---|---|
| *A61K 31/122* | (2006.01) | |
| *A61K 9/00* | (2006.01) | |
| *A61K 31/495* | (2006.01) | |
| *A61K 39/00* | (2006.01) | |
| *A61K 39/395* | (2006.01) | |
| *A61K 45/06* | (2006.01) | |
| *C07K 16/22* | (2006.01) | |

(52) U.S. Cl.
CPC .......... *A61K 31/122* (2013.01); *A61K 9/0019* (2013.01); *A61K 31/495* (2013.01); *A61K 39/3955* (2013.01); *A61K 45/06* (2013.01); *C07K 16/22* (2013.01); *A61K 2039/505* (2013.01); *C07K 2317/24* (2013.01)

(58) Field of Classification Search
CPC .. A61K 31/122; A61K 9/0019; A61K 31/495; A61K 39/3955; A61K 45/06; A61K 2039/505; C07K 16/22; C07K 2317/24; A61P 35/00
See application file for complete search history.

(56) References Cited

U.S. PATENT DOCUMENTS

| | | |
|---|---|---|
| 4,483,873 A | 11/1984 | Ohashi et al. |
| 4,515,736 A | 5/1985 | Deamer |
| 4,525,350 A | 6/1985 | Casey et al. |
| 4,636,381 A | 1/1987 | Takada et al. |
| 4,654,373 A | 3/1987 | Bertelli |
| 4,824,669 A | 4/1989 | Folkers et al. |
| 4,833,128 A | 5/1989 | Solomon et al. |
| 4,895,727 A | 1/1990 | Allen |
| 5,015,483 A | 5/1991 | Haynes et al. |
| 5,045,559 A | 9/1991 | Scott |
| 5,362,494 A | 11/1994 | Zysman et al. |
| 5,378,461 A | 1/1995 | Neigut |
| 5,527,789 A | 6/1996 | Nyce |
| 5,602,184 A | 2/1997 | Myers et al. |
| 5,603,958 A | 2/1997 | Morein et al. |
| 5,605,930 A | 2/1997 | Samid |
| 5,651,991 A | 7/1997 | Sugiyama et al. |
| 5,700,482 A | 12/1997 | Frederiksen et al. |
| 5,719,303 A | 2/1998 | Yoshida et al. |
| 5,770,222 A | 6/1998 | Unger et al. |
| 5,876,737 A | 3/1999 | Schonrock et al. |
| 5,889,062 A | 3/1999 | Hoppe et al. |
| 5,891,465 A | 4/1999 | Keller et al. |
| 5,912,272 A | 6/1999 | Hoppe et al. |
| 5,944,012 A | 8/1999 | Pera |
| 5,962,243 A | 10/1999 | Brown et al. |
| 6,005,086 A | 12/1999 | Evans et al. |
| 6,048,886 A | 4/2000 | Neigut |
| 6,063,820 A | 5/2000 | Cavazza |
| 6,071,495 A | 6/2000 | Unger et al. |
| 6,093,706 A | 7/2000 | Zeligs |
| 6,093,743 A | 7/2000 | Lai et al. |
| 6,184,353 B1 | 2/2001 | Evans et al. |
| 6,228,891 B1 | 5/2001 | Enzmann et al. |
| 6,261,575 B1 | 7/2001 | Hoppe et al. |
| 6,348,506 B2 | 2/2002 | Sneed |
| 6,372,234 B1 | 4/2002 | Deckers et al. |

(Continued)

FOREIGN PATENT DOCUMENTS

| | | |
|---|---|---|
| CA | 2436374 A1 | 8/2002 |
| CA | 2553690 A1 | 8/2005 |

(Continued)

OTHER PUBLICATIONS

Adeberg et al., Radiotherapy plus concomitant temozolomide in primary gliosarcoma. J Neurooncol. Jun. 2016;128(2):341-8.
Liao et al., The compounding effects of coenzyme q10 and radiation treatment on glial fibrillary acidic protein network of glioma in vitro. Cancer Res. 2019;79(13 Suppl):2931. 4 pages.
Marin et al., Overview of the molecular bases of resistance to chemotherapy in liver and gastrointestinal tumours. Curr Mol Med. Dec. 2009;9(9):1108-29.

(Continued)

*Primary Examiner* — Alana Harris Dent
(74) *Attorney, Agent, or Firm* — McCarter & English, LLP; Jill Mello

(57) ABSTRACT

The invention provides methods and compositions for treatment of a subject with a glioma that has failed treatment with temozolomide (TMZ) comprising administration of a composition comprising a Coenzyme Q10 compound to the subject. The invention also provides a method of treating a cancer that exhibits increased Complex II activity in a subject comprising administration of a composition comprising a Coenzyme Q10 compound to the subject.

21 Claims, 15 Drawing Sheets

(56) References Cited

U.S. PATENT DOCUMENTS

| | | |
|---|---|---|
| 6,403,116 B1 | 6/2002 | Anderson et al. |
| 6,416,957 B1 | 7/2002 | Evans et al. |
| 6,417,233 B1 | 7/2002 | Sears et al. |
| 6,441,050 B1 | 8/2002 | Chopra |
| 6,461,593 B1 | 10/2002 | Hanioka et al. |
| 6,465,517 B1 | 10/2002 | Van Der Zee |
| 6,468,552 B1 | 10/2002 | Stahl et al. |
| 6,469,061 B1 | 10/2002 | Flescher et al. |
| 6,482,943 B1 | 11/2002 | Blokhin et al. |
| 6,503,506 B1 | 1/2003 | Germano |
| 6,503,523 B2 | 1/2003 | Hoppe et al. |
| 6,506,915 B1 | 1/2003 | West |
| 6,511,800 B1 | 1/2003 | Singh |
| 6,531,117 B2 | 3/2003 | Heger et al. |
| 6,569,463 B2 | 5/2003 | Patel et al. |
| 6,573,284 B1 | 6/2003 | Riley et al. |
| 6,576,660 B1 | 6/2003 | Liao et al. |
| 6,576,678 B1 | 6/2003 | Bruening et al. |
| 6,582,710 B2 | 6/2003 | Deckers et al. |
| 6,582,723 B2 | 6/2003 | Gorsek |
| 6,596,287 B2 | 7/2003 | Deckers et al. |
| 6,599,513 B2 | 7/2003 | Deckers et al. |
| 6,623,746 B1 | 9/2003 | Wadle et al. |
| 6,630,160 B1 | 10/2003 | Evans et al. |
| 6,632,443 B2 | 10/2003 | Borowy-Borowski et al. |
| 6,652,891 B2 | 11/2003 | Selzer |
| 6,682,763 B2 | 1/2004 | Kuno et al. |
| 6,686,485 B2 | 2/2004 | West |
| 6,696,484 B2 | 2/2004 | Liao et al. |
| 6,726,924 B2 | 4/2004 | Keller |
| 6,727,234 B2 | 4/2004 | Wiemer et al. |
| 6,733,790 B1 | 5/2004 | Garces Garces |
| 6,753,325 B2 | 6/2004 | Rosenbloom |
| 6,803,193 B1 | 10/2004 | Hopper et al. |
| 6,806,069 B2 | 10/2004 | Chokshi |
| 6,809,176 B2 | 10/2004 | Blokhin et al. |
| 6,866,864 B2 | 3/2005 | Mousa |
| 6,867,024 B2 | 3/2005 | Chokshi |
| 6,906,106 B2 | 6/2005 | Chevalier |
| 6,923,988 B2 | 8/2005 | Patel et al. |
| 7,005,274 B1 | 2/2006 | Terkeltaub et al. |
| 7,060,733 B2 | 6/2006 | Pandol et al. |
| 7,083,572 B2 | 8/2006 | Unger et al. |
| 7,083,780 B2 | 8/2006 | Ansmann et al. |
| 7,091,241 B2 | 8/2006 | Gilloteaux et al. |
| 7,101,536 B2 | 9/2006 | Mongiat et al. |
| 7,132,268 B2 | 11/2006 | Miyake et al. |
| 7,147,841 B2 | 12/2006 | Herzog |
| 7,169,385 B2 | 1/2007 | Fantuzzi et al. |
| 7,169,590 B2 | 1/2007 | Ueda et al. |
| 7,176,171 B2 | 2/2007 | Nieendick et al. |
| 7,179,880 B2 | 2/2007 | Kawa et al. |
| 7,182,938 B2 | 2/2007 | Andre et al. |
| 7,182,950 B2 | 2/2007 | Garti et al. |
| 7,198,801 B2 | 4/2007 | Carrara et al. |
| 7,208,298 B2 | 4/2007 | Miyake et al. |
| 7,247,714 B2 | 7/2007 | Kunsch et al. |
| 7,250,174 B2 | 7/2007 | Lee et al. |
| 7,268,107 B2 | 9/2007 | Nieendick et al. |
| 7,273,606 B2 | 9/2007 | Fantuzzi et al. |
| 7,279,456 B2 | 10/2007 | Dufay et al. |
| 7,311,897 B2 | 12/2007 | Ehlis et al. |
| 7,318,929 B2 | 1/2008 | Schieferstein et al. |
| 7,357,918 B2 | 4/2008 | Comte et al. |
| 7,456,161 B2 | 11/2008 | Nyce |
| 7,635,722 B1 | 12/2009 | Bachynsky et al. |
| 7,776,894 B2 | 8/2010 | Ronai et al. |
| 7,824,673 B2 | 11/2010 | Wegman et al. |
| 7,858,659 B2 | 12/2010 | Hoffman et al. |
| 7,879,823 B2 | 2/2011 | Seiberg et al. |
| 7,906,140 B2 | 3/2011 | Bromley et al. |
| 8,147,825 B2 | 4/2012 | Hsia et al. |
| 8,293,227 B2 | 10/2012 | Hsia et al. |
| 8,562,976 B2 | 10/2013 | Hsia et al. |
| 8,586,030 B2 | 11/2013 | Hsia et al. |
| 8,746,515 B2 | 6/2014 | Fatherazi et al. |
| 8,771,680 B2 | 7/2014 | Hsia et al. |
| 9,205,064 B2 | 12/2015 | Narain et al. |
| 9,220,776 B2 | 12/2015 | Sharma et al. |
| 9,896,731 B2 | 2/2018 | Narain et al. |
| 9,901,542 B2 | 2/2018 | Narain et al. |
| 9,926,580 B2 | 3/2018 | Yajima et al. |
| 10,351,915 B2 | 7/2019 | Narain et al. |
| 10,376,477 B2 | 8/2019 | Jimenez et al. |
| 10,519,504 B2 | 12/2019 | Narain et al. |
| 10,583,098 B2 | 3/2020 | Hsia et al. |
| 10,933,032 B2 | 3/2021 | Narain et al. |
| 11,028,446 B2 | 6/2021 | Narain et al. |
| 11,298,313 B2 | 4/2022 | Narain et al. |
| 2001/0022965 A1 | 9/2001 | Heger et al. |
| 2001/0043909 A1 | 11/2001 | SaNogueira et al. |
| 2001/0053356 A1 | 12/2001 | Mousa |
| 2002/0039595 A1 | 4/2002 | Keller |
| 2002/0044913 A1 | 4/2002 | Hamilton |
| 2002/0045230 A1 | 4/2002 | Rosen et al. |
| 2002/0048559 A1 | 4/2002 | Shinoda et al. |
| 2002/0048798 A1 | 4/2002 | Avery et al. |
| 2002/0049176 A1 | 4/2002 | Anderson et al. |
| 2002/0049253 A1 | 4/2002 | Kaddurah-Daouk |
| 2002/0049422 A1 | 4/2002 | Brewitt |
| 2002/0058712 A1 | 5/2002 | Sneed |
| 2002/0071852 A1 | 6/2002 | Deckers et al. |
| 2002/0091288 A1 | 7/2002 | Wilbur et al. |
| 2002/0098169 A1 | 7/2002 | Smith |
| 2002/0106337 A1 | 8/2002 | Deckers et al. |
| 2002/0114820 A1 | 8/2002 | Deckers et al. |
| 2002/0127252 A1 | 9/2002 | Kramer et al. |
| 2002/0136711 A1 | 9/2002 | Cochran |
| 2002/0146463 A1 | 10/2002 | Clayton |
| 2002/0155151 A1 | 10/2002 | Enzmann et al. |
| 2002/0156302 A1 | 10/2002 | West |
| 2002/0164317 A1 | 11/2002 | Gorsek |
| 2002/0182199 A1 | 12/2002 | Hoppe et al. |
| 2002/0198177 A1 | 12/2002 | Horrobin |
| 2003/0012762 A1 | 1/2003 | Zulli et al. |
| 2003/0012779 A1 | 1/2003 | Grieb et al. |
| 2003/0012825 A1 | 1/2003 | Kapper |
| 2003/0031688 A1 | 2/2003 | Ghosh et al. |
| 2003/0044441 A1 | 3/2003 | Schmid et al. |
| 2003/0077297 A1 | 4/2003 | Chen et al. |
| 2003/0077335 A1 | 4/2003 | Richardson et al. |
| 2003/0087331 A1 | 5/2003 | Pettit et al. |
| 2003/0091518 A1 | 5/2003 | Pauly et al. |
| 2003/0103954 A1 | 6/2003 | Rosenbloom |
| 2003/0104048 A1 | 6/2003 | Patel et al. |
| 2003/0104080 A1 | 6/2003 | Singh et al. |
| 2003/0105027 A1 | 6/2003 | Rosenbloom |
| 2003/0105030 A1 | 6/2003 | Liao et al. |
| 2003/0105031 A1 | 6/2003 | Rosenbloom |
| 2003/0108493 A1 | 6/2003 | Henry et al. |
| 2003/0113354 A1 | 6/2003 | Schmid et al. |
| 2003/0118525 A1 | 6/2003 | Grigg |
| 2003/0118536 A1 | 6/2003 | Rosenbloom |
| 2003/0118576 A1 | 6/2003 | Brancato et al. |
| 2003/0124158 A1 | 7/2003 | Heidenfelder et al. |
| 2003/0129150 A1 | 7/2003 | Pauly et al. |
| 2003/0138792 A1 | 7/2003 | Schlegel et al. |
| 2003/0143166 A1 | 7/2003 | Heger et al. |
| 2003/0144346 A1 | 7/2003 | Liao et al. |
| 2003/0152598 A1 | 8/2003 | Heidenfelder et al. |
| 2003/0161849 A1 | 8/2003 | Heidenfelder et al. |
| 2003/0167556 A1 | 9/2003 | Kelley |
| 2003/0170265 A1 | 9/2003 | Henry et al. |
| 2003/0180231 A1 | 9/2003 | Danoux et al. |
| 2003/0180278 A1 | 9/2003 | Hoppe et al. |
| 2003/0180352 A1 | 9/2003 | Patel et al. |
| 2003/0185865 A1 | 10/2003 | Jentzsch et al. |
| 2003/0207834 A1 | 11/2003 | Dale et al. |
| 2003/0212114 A1 | 11/2003 | Sato |
| 2003/0215406 A1 | 11/2003 | Schreiner et al. |
| 2003/0219472 A1 | 11/2003 | Pauletti et al. |
| 2003/0235812 A1 | 12/2003 | Anderson et al. |
| 2004/0028614 A1 | 2/2004 | Corbella et al. |
| 2004/0028668 A1 | 2/2004 | Gaetani |

(56) References Cited

U.S. PATENT DOCUMENTS

| | | |
|---|---|---|
| 2004/0034107 A1 | 2/2004 | Enzmann |
| 2004/0043045 A1 | 3/2004 | Seipel et al. |
| 2004/0047896 A1 | 3/2004 | Malnoe et al. |
| 2004/0049022 A1 | 3/2004 | Nyce et al. |
| 2004/0063648 A1 | 4/2004 | Pandol et al. |
| 2004/0063661 A1 | 4/2004 | Linnane |
| 2004/0067260 A1 | 4/2004 | Milley et al. |
| 2004/0082522 A1 | 4/2004 | Nyce |
| 2004/0086538 A1 | 5/2004 | Sauermann et al. |
| 2004/0101874 A1 | 5/2004 | Ghosh et al. |
| 2004/0109880 A1 | 6/2004 | Pauly et al. |
| 2004/0110848 A1 | 6/2004 | Peffley et al. |
| 2004/0115181 A1 | 6/2004 | Fujii et al. |
| 2004/0122109 A1 | 6/2004 | Fujii et al. |
| 2004/0126367 A1 | 7/2004 | Fujii et al. |
| 2004/0133352 A1 | 7/2004 | Bevilacqua et al. |
| 2004/0142006 A1 | 7/2004 | Bleckmann et al. |
| 2004/0142007 A1 | 7/2004 | Moussou et al. |
| 2004/0142009 A1 | 7/2004 | Ansmann et al. |
| 2004/0151710 A1 | 8/2004 | Bozzacco |
| 2004/0151711 A1 | 8/2004 | West |
| 2004/0170560 A1 | 9/2004 | Fossheim et al. |
| 2004/0170581 A1 | 9/2004 | Henry et al. |
| 2004/0185071 A1 | 9/2004 | Hatazaki |
| 2004/0191190 A1 | 9/2004 | Pauly et al. |
| 2004/0191263 A1 | 9/2004 | Hageman et al. |
| 2004/0197279 A1 | 10/2004 | Bleckmann et al. |
| 2004/0197354 A1 | 10/2004 | Doring et al. |
| 2004/0202740 A1 | 10/2004 | Tan |
| 2004/0219114 A1 | 11/2004 | Andersson et al. |
| 2004/0228910 A1 | 11/2004 | Enzmann et al. |
| 2004/0234559 A1 | 11/2004 | Bleckmann et al. |
| 2004/0253323 A1 | 12/2004 | Giles |
| 2004/0258717 A1 | 12/2004 | Sauermann et al. |
| 2005/0000390 A1 | 1/2005 | Nieendick et al. |
| 2005/0008581 A1 | 1/2005 | Parkhideh |
| 2005/0019268 A1 | 1/2005 | Enzmann |
| 2005/0019278 A1 | 1/2005 | Berg-Schultz |
| 2005/0019353 A1 | 1/2005 | Prinz et al. |
| 2005/0025756 A1 | 2/2005 | Erwin |
| 2005/0026848 A1 | 2/2005 | Robinson et al. |
| 2005/0026850 A1 | 2/2005 | Robinson et al. |
| 2005/0036976 A1 | 2/2005 | Rubin et al. |
| 2005/0037036 A1 | 2/2005 | Nielsen et al. |
| 2005/0037102 A1 | 2/2005 | Tan et al. |
| 2005/0042678 A1 | 2/2005 | Epstein et al. |
| 2005/0043336 A1 | 2/2005 | Hennequin et al. |
| 2005/0058610 A1 | 3/2005 | Baschong et al. |
| 2005/0069582 A1 | 3/2005 | Fantuzzi |
| 2005/0070610 A1 | 3/2005 | Fujii et al. |
| 2005/0070611 A1 | 3/2005 | Fantuzzi |
| 2005/0079164 A1 | 4/2005 | Fantuzzi et al. |
| 2005/0100537 A1 | 5/2005 | Evans et al. |
| 2005/0106190 A1 | 5/2005 | Kawa et al. |
| 2005/0106199 A1 | 5/2005 | Schreiber et al. |
| 2005/0112156 A1 | 5/2005 | Busch et al. |
| 2005/0118151 A1 | 6/2005 | Larsen et al. |
| 2005/0118209 A1 | 6/2005 | Jentzsch et al. |
| 2005/0136081 A1 | 6/2005 | Kawa et al. |
| 2005/0142123 A1 | 6/2005 | Chen et al. |
| 2005/0142153 A1 | 6/2005 | Schreiber et al. |
| 2005/0147598 A1 | 7/2005 | Ueda et al. |
| 2005/0148603 A1 | 7/2005 | Jimenez et al. |
| 2005/0152856 A2 | 7/2005 | Andersson et al. |
| 2005/0184275 A1 | 8/2005 | Mora-Gutierrez et al. |
| 2005/0202521 A1 | 9/2005 | Crum |
| 2005/0214333 A1 | 9/2005 | Lanzendoerfer et al. |
| 2005/0220726 A1 | 10/2005 | Pauly et al. |
| 2005/0220826 A1 | 10/2005 | Kawa et al. |
| 2005/0226824 A1 | 10/2005 | Kawa et al. |
| 2005/0226858 A1 | 10/2005 | Kitamura et al. |
| 2005/0226947 A1 | 10/2005 | Kern |
| 2005/0238679 A1 | 10/2005 | Biergiesser et al. |
| 2005/0239721 A1 | 10/2005 | Rosenbloom |
| 2005/0255057 A1 | 11/2005 | Andre et al. |
| 2005/0276764 A1 | 12/2005 | Kolbe et al. |
| 2005/0281772 A1 | 12/2005 | Bromley et al. |
| 2005/0287206 A1 | 12/2005 | Fantuzzi et al. |
| 2005/0288333 A1 | 12/2005 | Kem |
| 2005/0288378 A1 | 12/2005 | Yan et al. |
| 2006/0002911 A1 | 1/2006 | Casteilla et al. |
| 2006/0002964 A9 | 1/2006 | Schreiber et al. |
| 2006/0008482 A1 | 1/2006 | Prinz et al. |
| 2006/0010519 A1 | 1/2006 | Kadowaki et al. |
| 2006/0013888 A1 | 1/2006 | Fantuzzi |
| 2006/0035981 A1 | 2/2006 | Mazzio et al. |
| 2006/0039956 A1 | 2/2006 | Hensen et al. |
| 2006/0041017 A1 | 2/2006 | Chopra |
| 2006/0051462 A1 | 3/2006 | Wang |
| 2006/0052438 A1 | 3/2006 | Ho et al. |
| 2006/0057081 A1 | 3/2006 | Boxrud |
| 2006/0062755 A1 | 3/2006 | Woodward |
| 2006/0069068 A1 | 3/2006 | Kajander et al. |
| 2006/0073106 A1 | 4/2006 | Berg-Schultz et al. |
| 2006/0093633 A1 | 5/2006 | Stab et al. |
| 2006/0099158 A1 | 5/2006 | Zander et al. |
| 2006/0099244 A1 | 5/2006 | Guilford |
| 2006/0110415 A1 | 5/2006 | Gupta |
| 2006/0120997 A1 | 6/2006 | Lipton |
| 2006/0121016 A1 | 6/2006 | Lee |
| 2006/0127384 A1 | 6/2006 | Capaccioli et al. |
| 2006/0127928 A1 | 6/2006 | Bacus et al. |
| 2006/0128643 A1 | 6/2006 | Kaddurah-Daouk et al. |
| 2006/0153783 A1 | 7/2006 | Ehlis et al. |
| 2006/0188459 A1 | 8/2006 | Heinrichs et al. |
| 2006/0188492 A1 | 8/2006 | Richardson et al. |
| 2006/0193905 A1 | 8/2006 | Ehringer et al. |
| 2006/0205771 A1 | 9/2006 | Noble et al. |
| 2006/0251690 A1 | 11/2006 | Lipshutz et al. |
| 2006/0251708 A1 | 11/2006 | Chen et al. |
| 2006/0252042 A1 | 11/2006 | Molero |
| 2006/0286046 A1 | 12/2006 | Haber |
| 2006/0292220 A1 | 12/2006 | Giordano et al. |
| 2007/0021360 A1 | 1/2007 | Nyce et al. |
| 2007/0026072 A1 | 2/2007 | Olsen et al. |
| 2007/0053985 A1 | 3/2007 | Ueda et al. |
| 2007/0054282 A1 | 3/2007 | Liew |
| 2007/0071779 A1 | 3/2007 | McKie |
| 2007/0085059 A1 | 4/2007 | Mora-Gutierrez et al. |
| 2007/0092469 A1 | 4/2007 | Jacobs |
| 2007/0104701 A1 | 5/2007 | Ueda et al. |
| 2007/0104810 A1 | 5/2007 | Kern |
| 2007/0110731 A1 | 5/2007 | Riley |
| 2007/0129428 A1 | 6/2007 | Richelle et al. |
| 2007/0149618 A1 | 6/2007 | Cuevas Sanchez et al. |
| 2007/0160685 A1 | 7/2007 | Knox et al. |
| 2007/0172436 A1 | 7/2007 | Zhang |
| 2007/0184041 A1 | 8/2007 | Burja |
| 2007/0184076 A1 | 8/2007 | Unger et al. |
| 2007/0189994 A1 | 8/2007 | Berg et al. |
| 2007/0196349 A1 | 8/2007 | Kitamura et al. |
| 2007/0196914 A1 | 8/2007 | Murray et al. |
| 2007/0202090 A1 | 8/2007 | Prosek et al. |
| 2007/0202496 A1 | 8/2007 | Beretta |
| 2007/0203091 A1 | 8/2007 | Rapaport |
| 2007/0218042 A1 | 9/2007 | Khaled |
| 2007/0225255 A1 | 9/2007 | Frohlich et al. |
| 2007/0243180 A1 | 10/2007 | Tanaka et al. |
| 2007/0248590 A1 | 10/2007 | Milne et al. |
| 2007/0248693 A1 | 10/2007 | Mazzio et al. |
| 2007/0253941 A1 | 11/2007 | Naidu et al. |
| 2007/0258966 A1 | 11/2007 | Ueda et al. |
| 2007/0258967 A1 | 11/2007 | Ueda et al. |
| 2007/0259009 A1 | 11/2007 | Linder |
| 2007/0275021 A1 | 11/2007 | Lee et al. |
| 2008/0014187 A1 | 1/2008 | Villeponteau |
| 2008/0020018 A1 | 1/2008 | Moodley et al. |
| 2008/0020022 A1 | 1/2008 | Udell |
| 2008/0025929 A1 | 1/2008 | Burton et al. |
| 2008/0031862 A1 | 2/2008 | Ghosal |
| 2008/0038736 A1 | 2/2008 | Llovet et al. |
| 2008/0057116 A1 | 3/2008 | Pleva |
| 2008/0063674 A1 | 3/2008 | Vollhardt et al. |
| 2008/0069779 A1 | 3/2008 | Tamarkin et al. |

(56) References Cited

U.S. PATENT DOCUMENTS

| | | | |
|---|---|---|---|
| 2008/0069898 A1 | 3/2008 | Smith et al. | |
| 2008/0075684 A1 | 3/2008 | Barg et al. | |
| 2008/0081034 A1 | 4/2008 | Zimmerman et al. | |
| 2008/0081082 A1 | 4/2008 | Zimmerman et al. | |
| 2008/0089852 A1 | 4/2008 | Hotz et al. | |
| 2008/0089913 A1 | 4/2008 | Kallmayer et al. | |
| 2008/0095719 A1 | 4/2008 | Herrmann et al. | |
| 2008/0102313 A1 | 5/2008 | Nilsen et al. | |
| 2008/0103104 A1* | 5/2008 | Moore | C07C 233/65 536/17.6 |
| 2008/0138326 A1 | 6/2008 | Fujii et al. | |
| 2008/0233183 A1 | 9/2008 | McCook et al. | |
| 2008/0260878 A1 | 10/2008 | Harano et al. | |
| 2008/0287541 A1 | 11/2008 | Hoffman et al. | |
| 2008/0299100 A1 | 12/2008 | Hsia et al. | |
| 2009/0005398 A1 | 1/2009 | Dar | |
| 2009/0010917 A1 | 1/2009 | Rosenblum et al. | |
| 2009/0036516 A1 | 2/2009 | Scherrer et al. | |
| 2009/0060891 A1 | 3/2009 | Harris et al. | |
| 2009/0068281 A1 | 3/2009 | Toyomura et al. | |
| 2009/0137556 A1 | 5/2009 | Bonnichsen | |
| 2009/0280987 A1 | 11/2009 | Strobel | |
| 2010/0062048 A1 | 3/2010 | Hsia et al. | |
| 2010/0150894 A1 | 6/2010 | Wakabayashi et al. | |
| 2010/0209388 A1 | 8/2010 | Mazzio et al. | |
| 2010/0209497 A1 | 8/2010 | Thornthwaite | |
| 2010/0239652 A1 | 9/2010 | Rochlitz et al. | |
| 2011/0020312 A1 | 1/2011 | Narain et al. | |
| 2011/0027247 A1 | 2/2011 | Narain et al. | |
| 2011/0064747 A1 | 3/2011 | Sarangarajan et al. | |
| 2011/0123550 A1 | 5/2011 | Shibayama et al. | |
| 2011/0123986 A1 | 5/2011 | Narain et al. | |
| 2011/0129503 A1 | 6/2011 | Strober et al. | |
| 2011/0136231 A1 | 6/2011 | Narain et al. | |
| 2011/0142914 A1 | 6/2011 | Persaud et al. | |
| 2011/0229554 A1 | 9/2011 | Narain et al. | |
| 2012/0164215 A1 | 6/2012 | Hsia et al. | |
| 2012/0183621 A1 | 7/2012 | Sinko et al. | |
| 2012/0201801 A1 | 8/2012 | Hsia et al. | |
| 2012/0269867 A1 | 10/2012 | Jimenez et al. | |
| 2012/0309086 A1 | 12/2012 | Narain et al. | |
| 2013/0203853 A1 | 8/2013 | Jacobson | |
| 2014/0017317 A1 | 1/2014 | Narain et al. | |
| 2014/0255372 A1 | 9/2014 | Hsia et al. | |
| 2014/0302014 A1* | 10/2014 | Narain | A61K 39/39558 424/94.1 |
| 2015/0023940 A1 | 1/2015 | Narain et al. | |
| 2016/0145693 A1 | 5/2016 | Narain et al. | |
| 2017/0137879 A1 | 5/2017 | Narain et al. | |
| 2017/0189350 A1 | 7/2017 | Narain et al. | |
| 2017/0216223 A1 | 8/2017 | Narain et al. | |
| 2018/0021270 A1 | 1/2018 | Nastke et al. | |
| 2018/0334721 A1 | 11/2018 | Narain et al. | |
| 2019/0010554 A1 | 1/2019 | Narain et al. | |
| 2020/0009377 A1 | 1/2020 | Chang et al. | |
| 2020/0078320 A1 | 3/2020 | Jimenez et al. | |
| 2020/0138744 A1 | 5/2020 | Sarangarajan et al. | |
| 2021/0002725 A1 | 1/2021 | Narain et al. | |
| 2021/0128453 A1 | 5/2021 | Hsia et al. | |
| 2021/0322339 A1 | 10/2021 | Narain et al. | |
| 2021/0332439 A1 | 10/2021 | Narain et al. | |
| 2021/0369645 A1 | 12/2021 | Narain et al. | |
| 2022/0081720 A1 | 3/2022 | Narain et al. | |
| 2022/0096399 A1 | 3/2022 | Narain et al. | |
| 2022/0096400 A1 | 3/2022 | Nastke et al. | |
| 2023/0149292 A1 | 5/2023 | Hsia et al. | |
| 2023/0285272 A1 | 9/2023 | Narain et al. | |

FOREIGN PATENT DOCUMENTS

| | | |
|---|---|---|
| CA | 2680825 A1 | 9/2008 |
| CA | 2791693 A1 | 9/2011 |
| CN | 1535605 A | 10/2004 |
| CN | 1853507 A | 11/2006 |
| CN | 1928556 A | 3/2007 |
| CN | 1953743 A | 4/2007 |
| CN | 101099084 A | 1/2008 |
| CN | 101102768 A | 1/2008 |
| CN | 101365806 A | 2/2009 |
| CN | 102481269 A | 5/2012 |
| DE | 4327063 A1 | 2/1995 |
| EA | 201001624 A1 | 6/2011 |
| EP | 1473043 A1 | 11/2004 |
| EP | 1493437 A1 | 1/2005 |
| EP | 1908459 A1 | 4/2008 |
| EP | 2028492 A1 | 2/2009 |
| EP | 2371362 A1 | 10/2011 |
| EP | 2371363 A1 | 10/2011 |
| EP | 2429512 A2 | 3/2012 |
| EP | 2854528 A1 | 4/2015 |
| JP | S57-075916 A | 5/1982 |
| JP | S62-123113 A | 6/1987 |
| JP | H01-143826 A | 6/1989 |
| JP | H02-273619 A | 11/1990 |
| JP | 2001-514209 A | 9/2001 |
| JP | 2004-345988 A | 12/2004 |
| JP | 2005-323573 A | 11/2005 |
| JP | 2007-001922 A | 1/2007 |
| JP | 2007-176804 A | 7/2007 |
| JP | 2007-518805 A | 7/2007 |
| JP | 2009-050168 A | 3/2009 |
| JP | 2009-096757 A | 5/2009 |
| JP | 2012-510932 A | 5/2012 |
| JP | 2015-515272 A | 5/2015 |
| JP | 2015-151900 A | 8/2015 |
| JP | 2018-109093 A | 7/2018 |
| JP | 2018-168164 A | 11/2018 |
| KR | 10-2005-0112942 A | 12/2005 |
| RU | 2307666 C2 | 10/2007 |
| RU | 2345367 | 1/2009 |
| WO | WO-1988/04173 A1 | 6/1988 |
| WO | WO-1993/016704 A1 | 9/1993 |
| WO | WO-1994/11547 A1 | 5/1994 |
| WO | WO-1995/05164 A1 | 2/1995 |
| WO | WO-1995/10271 A2 | 4/1995 |
| WO | WO-1996/017626 A2 | 6/1996 |
| WO | WO-1998/35660 A1 | 8/1998 |
| WO | WO-1999/11242 A1 | 3/1999 |
| WO | WO-1999/65469 A2 | 12/1999 |
| WO | WO-2000/007607 A1 | 2/2000 |
| WO | WO-2002/40012 A1 | 5/2002 |
| WO | WO-2002/060484 A1 | 8/2002 |
| WO | WO-2002/062329 A1 | 8/2002 |
| WO | WO-2002/062338 A1 | 8/2002 |
| WO | WO-2002/078727 A1 | 10/2002 |
| WO | WO-2002/085297 A2 | 10/2002 |
| WO | WO-2003/008405 A1 | 1/2003 |
| WO | WO-2003/077895 A1 | 9/2003 |
| WO | WO-2003/078456 A2 | 9/2003 |
| WO | WO-2004/003564 A2 | 1/2004 |
| WO | WO-2004/059293 A2 | 7/2004 |
| WO | WO-2004/060316 A2 | 7/2004 |
| WO | WO-2005/055738 A1 | 6/2005 |
| WO | WO-2005/069916 A2 | 8/2005 |
| WO | WO-2006/017494 A2 | 2/2006 |
| WO | WO-2006/063402 A1 | 6/2006 |
| WO | WO-2007/039184 A2 | 4/2007 |
| WO | WO-2007/095186 A2 | 8/2007 |
| WO | WO-2007/131047 A2 | 11/2007 |
| WO | WO-2008/049330 A1 | 5/2008 |
| WO | WO-2008/116135 A2 | 9/2008 |
| WO | WO-2008/156654 A2 | 12/2008 |
| WO | WO-2009/005215 A1 | 1/2009 |
| WO | WO-2009/006366 A2 | 1/2009 |
| WO | WO-2009/012718 A1 | 1/2009 |
| WO | WO-2009/014639 A2 | 1/2009 |
| WO | WO-2009/073843 A1 | 6/2009 |
| WO | WO-2009/126764 A1 | 10/2009 |
| WO | WO-2010/065601 A1 | 6/2010 |
| WO | WO-2010/132440 A2 | 11/2010 |
| WO | WO-2010/132507 A2 | 11/2010 |
| WO | WO-2011/031503 A2 | 3/2011 |
| WO | WO-2011/112900 A2 | 9/2011 |

(56) References Cited

FOREIGN PATENT DOCUMENTS

| WO | WO-2012/012347 A2 | 1/2012 |
| WO | WO-2012/138765 A1 | 10/2012 |
| WO | WO-2013/181639 A1 | 12/2013 |
| WO | WO-2014/168993 A1 | 10/2014 |
| WO | WO-2015035094 A1 | 3/2015 |
| WO | WO-2016/054574 A1 | 4/2016 |
| WO | WO-2016/062722 A1 | 4/2016 |
| WO | WO-2016/094639 A1 | 6/2016 |
| WO | WO-2017/087576 A1 | 5/2017 |

OTHER PUBLICATIONS

NatMed Pro, Vitamin K1 vs K2: what you should know. Retrieved online at: https://naturalmedicines.therapeuticresearch.com/news/news-items/2019/may/vitamin-k1-vs-k2-what-you-should-know.aspx. 1 page, May 2019.

Sun et al., BPM31510, a Coenzyme Q10 (CoQ10) containing lipid nanodispersion, enhances radiation effects to prolong survival in a rodent glioblastoma model. Cancer Res. 80(16 Suppl):2968, 2 pages.

Abe et al., Effect of coenzyme Q10 in patients with mitochondrial myopathy, encephalopathy, lactic acidosis, and stroke-like episodes (MELAS): evaluation by noninvasive tissue oximetry. J Neurol Sci. Jan. 1, 1999;162(1):65-8.

Abe et al., Marked reduction in CSF lactate and pyruvate levels after CoQ therapy in a patient with mitochondrial myopathy, encephalopathy, lactic acidosis and stroke-like episodes (MELAS). Acta Neurol Scand. Jun. 1991;83(6):356-9.

Aizawa, Morphology of polysorbate 80 (Tween 80) micelles in aqueous dimethyl sulfoxide solutions. J Appl Crystallogr. Jun. 1, 2010;43(Pt 3):630-631.

American Cancer Society, Brain and Spinal Cord Tumors in Adults. Retrieved online at: http://www.cancer.org/cancer/braincnstumorsinadults/detailedguide/brain-and-spinal-cord-tumors-in-adults-what-are-brain-spinal-tumors. Nov. 12, 2009. 4 pages.

American Cancer Society, Colorectal Cancer. Retrieved online at: http:www.cancer.org/acs/groups/cid/documents/webcontent/003096-pdf.pdf. 122 pages, (2016).

Anderson et al., The transcriptional response to a peroxisome proliferator-activated receptor alpha agonist includes increased expression of proteome maintenance genes. J Biol Chem. Dec. 10, 2004;279(50):52390-8.

Ansell et al., Brain tumor signs and symptoms: analysis of primary health care records from the UKCCS. Pediatrics. Jan. 2010;125(1):112-9.

Antoneeva et al., Markers of Apoptosis and Proliferation of Tumor Cells in the Dynamic of Ovarian Cancer Progression. Oncologiya. 2008;10(2):234-237.

Aris et al., Noise filtering and nonparametric analysis of microarray data underscores discriminating markers of oral, prostate, lung, ovarian and breast cancer. BMC Bioinformatics. Nov. 29, 2004;5(185):1-9.

Barbiroli et al., Coenzyme Q10 improves mitochondrial respiration in patients with mitochondrial cytopathies. An in vivo study on brain and skeletal muscle by phosphorous magnetic resonance spectroscopy. Cell Mol Biol (Noisy-le-grand). Jul. 1997;43(5):741-9.

Bjarnason, Chronobiology. Implications for cancer chemotherapy. Acta Oncol. 1995;34(5):615-24.

Bliznakov et al., Coenzymes Q: stimulants of the phagocytic activity in rats and immune response in mice. Experientia. Sep. 26, 1970;26(9):953-4.

Bliznakov, Effect of stimulation of the host defense system by coenzyme Q 0 on dibenzpyrene-induced tumors and infection with Friend leukemia virus in mice. Proc Natl Acad Sci U S A. Feb. 1973;70(2):390-4.

Blom et al., The risk of a venous thrombotic event in lung cancer patients: higher risk for adenocarcinoma than squamous cell carcinoma. J Thromb Haemost. Oct. 2004;2(10):1760-5.

Bresolin et al., Clinical and biochemical correlations in mitochondrial myopathies treated with coenzyme Q10. Neurology. Jun. 1988;38(6):892-9.

Buric et al., Modulation of Antioxidant Potential with Coenzyme Q10 Suppressed Invasion of Temozolomide-Resistant Rat Glioma In Vitro and In Vivo. Oxid Med Cell Longev. Mar. 12, 2019;2019:3061607, 14 pages.

Cabrera et al., Radiation therapy for glioblastoma: Executive summary of an American Society for Radiation Oncology Evidence-Based Clinical Practice Guideline. Pract Radiat Oncol. Jul.-Aug. 2016;6(4):217-225.

Cancer.net, Brain Tumor: Symptoms and Signs. Retrieved online at: https://www.cancer.net/cancer-types/brain-tumor/symptoms-and-signs. 4 pages, (2005).

Cancer.net, Stages of Cancer. Doctor-Approved Patient Information from ASCO. Retrieved online at: https://www.cancer.net/navigating-cancer-care/diagnosing-cancer/stages-cancer. 4 pages, Mar. 2018.

Carmona et al., Coadministration of coenzyme Q prevents rosiglitazone-induced adipogenesis in ob/ob mice. Int J Obes (Lond). Feb. 2009;33(2):204-11.

Chan et al., Metabolic changes in patients with mitochondrial myopathies and effects of coenzyme Q10 therapy. J Neurol. Oct. 1998;245(10):681-5.

Chang et al., Patterns of resistance and incomplete response to docetaxel by gene expression profiling in breast cancer patients. J Clin Oncol. Feb. 20, 2005;23(6):1169-77.

Chen et al., Coenzyme Q10 treatment in mitochondrial encephalomyopathies. Short-term double-blind, crossover study. Eur Neurol. 1997;37(4):212-8.

Cheung et al., Novel markers of subclinical disease for Ewing family tumors from gene expression profiling. Clin Cancer Res. Dec. 1, 2007;13(23):6978-83.

Chew et al., Coenzyme Q10 and diabetic endotheliopathy: oxidative stress and the 'recoupling hypothesis'. QJM. Aug. 2004;97(8):537-48.

Chop, Pediatric Leukemias. Children's Hospital of Philadelphia, retrieved online at: https://www.chop.edu/conditions-diseases/pediatric-leukemias. 9 pages, (2021).

ClinicalTrials.gov, BPM31510 Administered Intravenously With Gemcitabine in Advanced Pancreatic Cancer Patients. NCT02650804, 9 pages, Sep. 16, 2020.

ClinicalTrials.gov, NCT01928394, A Study of Nivolumab by Itself or Nivolumab Combined With Ipilimumab in Patients With Advanced or Metastatic Solid Tumors. 9 pages, Oct. 4, 2019.

Colman et al., Hemostasis and Thrombosis. Basic Principles and Clinical Practice, 5th Edition, Lippincott Williams & Wilkins, p. 1161 (2006).

Colon cancer: Tests and diagnosis—MayoClinic.com. Retrieved online at: http://www.mayoclinic.com/health/colon-cancer/ds00035/dsection=tests-and-diagnosis. 3 pages, Aug. 13, 2011.

Conklin, Cancer chemotherapy and antioxidants. J Nutr. Nov. 2004;134(11):3201S-3204S.

Conklin, Coenzyme q10 for prevention of anthracycline-induced cardiotoxicity. Integr Cancer Ther. Jun. 2005;4(2):110-30.

Crane, New Functions for Coenzyme Q. Protoplasma. 2000;213:127-133.

Crawford et al., Multiplex standardized RT-PCR for expression analysis of many genes in small samples. Biochem Biophys Res Commun. Apr. 26, 2002;293(1):509-16.

De Oliveria, A Nutritious Cocktail for the Treatment of Melanoma: A Case Report. The Journal of Orthomolecular Medicine. 1998;13(3)13, 2 pages.

Deeb et al., Vitamin D signalling pathways in cancer: potential for anticancer therapeutics. Nat Rev Cancer. Sep. 2007;7(9):684-700.

Doi et al., The JAK/STAT pathway is involved in the upregulation of PD-L1 expression in pancreatic cancer cell lines. Oncol Rep. 2017;37(3):1545-1554.

Domae et al., Cardiomyopathy and other chronic toxic effects induced in rabbits by doxorubicin and possible prevention by coenzyme Q10. Cancer Treat Rep. Jan.-Feb. 1981;65(1-2):79-91.

Eisenhauer et al., New response evaluation criteria in solid tumours: Revised RECIST guideline (version 1.1). European Journal of Cancer. 2009;45:228-247.

(56) References Cited

OTHER PUBLICATIONS

Family Caregiver Alliance, Fact Sheet: Brain Tumor. Los Angeles Caregiver Resource Center. Retrieved online at: http://lacrc.usc.edu/forms/brain tumor.pdf. 12 pages (2004).
Fang et al., Expression of ectonucleotide pyrophosphatase/phosphodiesterase 1 in human ovary and its relationship with polycystic ovary syndrome. ACTA Anatomica Sinica. 2008;39(4):552-556.
Fernández-Ayala et al., Coenzyme Q protects cells against serum withdrawal-induced apoptosis by inhibition of ceramide release and caspase-3 activation. Antioxid Redox Signal. 2000 Summer;2(2):263-75.
Ferrara et al., Protective role of chronic ubiquinone administration on acute cardiac oxidative stress. J Pharmacol Exp Ther. Aug. 1995;274(2):858-65.
Folkers et al., Survival of cancer patients on therapy with coenzyme Q10. Biochem Biophys Res Commun. Apr. 1, 19935;192(1):241-5.
Folkers, Relevance of the biosynthesis of coenzyme Q10 and of the four bases of DNA as a rationale for the molecular causes of cancer and a therapy. Biochem Biophys Res Commun. Jul. 16, 1996;224(2):358-61.
Foulkes et al., Triple-negative breast cancer. N Engl J Med. Nov. 11, 2010;363(20):1938-48.
Friedman et al., Temozolomide and Treatment of Malignant Glioma. Clinical Cancer Research. Jul. 2000;6:2585-2597, plus supplemental material.
Frontinan-Rubio et al., Regulation of the oxidative balance with coenzyme Q10 sensitizes human glioblastoma cells to radiation and temozolomide. Radiother Oncol. Aug. 2018;128(2):236-244.
Gaby, The Role of Coenzyme Q10 in Clinical Medicine: Part I. Alt Med Rev. 1996;1:11-17.
Galili et al., Clinical response of myelodysplastic syndromes patients to treatment with coenzyme Q10. Leuk Res. Jan. 2007;31(1):19-26.
Gao et al., Effects of coenzyme Q10 on vascular endothelial function in humans: a meta-analysis of randomized controlled trials. Atherosclerosis. Apr. 2012;221(2):311-6.
Garrel et al., The diagnostic accuracy of reverse transcription—PCR quantification of cytokeratin mRNA in the detection of sentinel lymph node invasion in oral and oropharyngeal squamous cell carcinoma: a comparison with immunohistochemistry. Clin Cancer Res. Apr. 15, 2006;12(8):2498-505.
Gersten, Brain Cancer Overview. The New York Times. Retrieved online at: http://health.nytimes.com/health/guides/disease/brain-tumor-adults. 3 pages.
Gesta et al., BPM31510, a clinical stage metabolic modulator demonstrates therapeutic efficacy in an in vivo C6 rat glioma model and synergizes with temozolomide. Cancer Research. Jul. 2017;77(Suppl. 13):Abstract 4067.
Gillet et al., Mechanisms of Multidrug Resistance in Cancer. Multi-Drug Resistance in Cancer, Methods in Molecular Biology, vol. 596, J. Zhou (Ed.). Humana Press. Chapter 4, pp. 47-76, (2010).
Gogvadze et al., Mitochondria as targets for chemotherapy. Apoptosis. Apr. 2009;14(4):624-40.
Golay et al., Link between obesity and type 2 diabetes. Best Pract Res Clin Endocrinol Metab. Dec. 2005;19(4):649-63.
Gorelick et al., Coenzyme Q10 and lipid-related gene induction in Hela cells. Am J Obstet Gynecol. May 2004;190(5):1432-4.
Groneberg et al., Coenzyme Q10 affects expression of genes involved in cell signaling, metabolism and transport in human CaCo-2 cells. The International Journal of Biochemistry and Cell Biology. 2005;37:1208-1218.
Haider et al., Effects of etanercept are distinct from infliximab in modulating proinflammatory genes in activated human leukocytes. J Investig Dermatol Symp Proc. May 2007;12(1):9-15.
Happold et al., Distinct molecular mechanisms of acquired resistance to temozolomide in glioblastoma cells. J Neurochem. Jul. 2012;122(2):444-55.
Hertz et al., Improved survival in patients with end-stage cancer treated with coenzyme Q(10) and other antioxidants: a pilot study. J Int Med Res. Nov.-Dec. 2009;37(6):1961-71.
Higdon et al., Obesity and oxidative stress: a direct link to CVD? Arterioscler Thromb Vasc Biol. Mar. 1, 2003;23(3):365-7.
Hill et al., Pharmacokinetics of drug infusions. Continuing Education in Anaesthesia. 2004. 4(3):76-80.
Hodges et al., CoQ10: could it have a role in cancer management? Biofactors. 1999;9(2-4):365-70.
Hodgson et al., Coenzyme Q10 improves blood pressure and glycaemic control: a controlled trial in subjects with type 2 diabetes. Eur J Clin Nutr. Nov. 2002;56(11):1137-42.
Huang et al., Treatment of refractory recurrent malignant glioma with adoptive cellular immunotherapy: a case report. Critical Reviews in Oncology/Hematology. 2001;57:17-23.
Hudson et al., Characterization of potentially chemopreventive phenols in extracts of brown rice that inhibit the growth of human breast and colon cancer cells. Cancer Epidemiol Biomarkers Prev. Nov. 2000;9(11):1163-70.
Iarussi et al., Protective effect of coenzyme Q10 on anthracyclines cardiotoxicity: control study in children with acute lymphoblastic leukemia and non-Hodgkin lymphoma. Mol Aspects Med. 1994;15 Suppl:s207-12.
Izyumov, Programmed Death of Cells and Oxidative Stress Caused by Inhibitors of Mitochondrial Functions. (synopsis of Ph.D. thesis), Moscow, 2005, pp. 17-20: URL: <http://www.lib.ua.net/diss/cont/151000.html>>.
Johnson et al., Gene expression profiles differentiate between sterile SIRS and early sepsis. Ann Surg. Apr. 2007;245(4):611-21.
Judy et al., Coenzyme Q10 Facts or Fiction. Natural Products Insider. 3 pages. Oct. 22, 2007.
Kawase et al., Enhancing effect of coenzyme, Q10 on immunorestoration with *Mycobacterium bovis* BCG in tumor-bearing mice. Gan. Aug. 1978;69(4):493-7.
Khan et al., Prolongation of Survival of Mice Bearing Leukemia 1210; Treated with Adriamycin and Coenzyme Q10. Proceedings of the American Association for Cancer Research. 1990;31:388, Poster 2303.
Kokawa et al., Coenzyme Q10 in cancer chemotherapy—experimental studies on augmentation of the effects of masked compounds, especially in the combined chemotherapy with immunopotentiators. Gan To Kagaku Ryoho. Mar. 1983;10(3):768-74. (Abstract only).
Kunitomo et al., Beneficial effect of coenzyme Q10 on increased oxidative and nitrative stress and inflammation and individual metabolic components developing in a rat model of metabolic syndrome. J Pharmacol Sci. Jun. 2008;107(2):128-37.
Lamson et al., Antioxidants in cancer therapy; their actions and interactions with oncologic therapies. Altern Med Rev. Oct. 1999;4(5):304-29.
Langer et al., Protein expression profiling in esophageal adenocarcinoma patients indicates association of heat-shock protein 27 expression and chemotherapy response. Clin Cancer Res. Dec. 15, 2008;14(24):8279-87.
Langham et al., Increased renal gene transcription of protein kinase C-beta in human diabetic nephropathy: relationship to long-term glycaemic control. Diabetologia. Apr. 2008;51(4):668-74.
Langsjoen, Alleviating Congestive Heart Failure with Coenzyme Q10. LifeExtension. http://www.lef.org/. Feb. 2008. 7 pages.
Laohapensang et al., An Unusual Complication of EVAR, Spontaneous Rectus Sheath Hematoma: A Case Report. Ann Vasc Dis. 2009;2(2):122-5.
Larsson, Effects of isoprenoids on growth of normal human mammary epithelial cells and breast cancer cells in vitro. Anticancer Res. Jan.-Feb. 1999;14(1A):123-8.
Lassman, Molecular Biology of Gliomas. Current Neurology and Neuroscience Reports. 2004;4:228-233.
Li et al., Candidate genes responsible for human hepatocellular carcinoma identified from differentially expressed genes in hepatocarcinogenesis of the tree shrew (*Tupaia belangeri chinesis*). Hepatol Res. Jan. 2008;38(1):85-95.
Li et al., Protective Effect of Coenzyme Q10 against the Adverse Reaction of Mytomycin G in Mouse Liver. Acta Histochemica et Cytochemica. 1987;20(4):455-467.

(56) References Cited

OTHER PUBLICATIONS

Liao et al., The compounding effects of coenzyme q10 and radiation treatment on glial fibrillary acidic protein network of glioma in vitro. AACR Annual Meeting. Oncodevelopment Biology and Medicine. Abstract 2931, Jul. 2019.
Littman et al., Effect of Cholesterol-Free, Fat-Free Diet and Hypocholesteremic Agents on Growth of Transplantable Animal Tumors. Cancer Chemotherapy Reports. Jan.-Feb. 1966;50(1 and 2):25-45.
Lockwood et al., Apparent partial remission of breast cancer in 'high risk' patients supplemented with nutritional antioxidants, essential fatty acids and coenzyme Q10. Mol Aspects Med. 1994;15 Suppl:s231-40.
Lockwood et al., Partial and complete regression of breast cancer in patients in relation to dosage of coenzyme Q10. Biochem Biophys Res Commun. Mar. 30, 1994;199(3):1504-8.
Lockwood et al., Progress on therapy of breast cancer with vitamin Q10 and the regression of metastases. Biochem Biophys Res Commun. Jul. 6, 1995;212(1):172-7.
Mazoff, Bleeding Disorders & Hepatitis C. HCV Advocate, HCSP Fact Sheet. www.hcvadvocate.org. HCSP, Version 3, 5 pages. Dec. 2014.
Mazzio et al., Effects of enhancing mitochondrial oxidative phosphorylation with reducing equivalents and ubiquinone on 1-methyl-4-phenylpyridinium toxicity and complex I-IV damage in neuroblastoma cells. Biochem Pharmacol. Mar. 15, 2004;67(6):1167-84.
Merck Manual Japanese Edition, 17th ed., pp. 59-63 (2002).
Merlo et al., FOXP3 expression and overall survival in breast cancer. J Clin Oncol. Apr. 10, 2009;27(11):1746-52.
Miles et al., Coenzyme Q10 changes are associated with metabolic syndrome. Clin Chim Acta. Jun. 2004;344(1-2):173-9.
Modi et al., Effect of coenzyme Q10 on catalase activity and other antioxidant parameters in streptozotocin-induced diabetic rats. Biol Trace Elem Res. Jan. 2006;109(1):25-34.
Mohammed et al., Prognostic significance of vascular endothelial cell growth factors-A, -C and -D in breast cancer and their relationship with angio- and lymphangiogenesis. Br J Cancer. Apr. 10, 2007;96(7):1092-100.
Mousa, Antithrombotic Effects of Naturally Derived Products on Coagulation and Platelet Function. Anticoagulants, Antiplatelets, and Thrombolytics, 2nd Edition. Humana Press, 2010, Chapter 9, pp. 229-240.
Mura et al., Evaluation of transcutol as a clonazepam transdermal permeation enhancer from hydrophilic gel formulations. Eur J Pharm Sci. Feb. 2000;9(4):365-72.
Narain et al., API 31510 as a potential agent in management of CNS leukemia. Cancer Research. 2011;71 (Suppl 8), Abstract 1565. Proceedings: AACR 102nd Annual Meeting 2011.
Narain et al., Effect of pretreatment, dose and route of administration of BPM31510 (Coenxyme Q10 containing proprietry formulation) alone or in combination with gemcitabine improves survival in pancreatic cancer. Cancer Res. 2014;74(19 Suppl.):Abstract 4321.
Neidle, Cancer Drug Design and Discovery. Elsevier/Academic Press. p. 431, (2008).
Nih, National Cancer Institute, Continuous Infusion. Retrieved online at: https://www.cancer.gov/publications/dictionaries/cancer-terms/def/continuous-infusion. 1 page, (2020).
Nih, National Cancer Institute, Drugs Approved for Different Types of Cancer. 7 pages, Jan. 16, 2015.
Nissim, A Gentle Cancer Killer. University of Miami Medicine-Online. Retrieved online at: http://www6.miami.edu/ummedicine-magazine/fall2005/fstory4.html. 3 pages. 2005.
O'Driscoll et al., Feasibility and relevance of global expression profiling of gene transcripts in serum from breast cancer patients using whole genome microarrays and quantitative RT-PCR. Cancer Genomics Proteomics. Mar.-Apr. 2008;5(2):94-104.
Ohanian et al., Is acute myeloid leukemia a liquid tumor? Int J Cancer. Aug. 1, 2013;133(3):534-43.
Ohira et al., Expression profiling and characterization of 4200 genes cloned from primary neuroblastomas: identification of 305 genes differentially expressed between favorable and unfavorable subsets. Oncogene. Aug. 21, 2003;22(35):5525-36.
Okumura et al., Identification of biomarkers in ductal carcinoma in situ of the breast with microinvasion. BMC Cancer. Oct. 6, 2008;8:287.
Olopade et al., Overexpression of BCL-x protein in primary breast cancer is associated with high tumor grade and nodal metastases. Cancer J Sci Am. Jul.-Aug. 1997;3(4):230-7.
Olson, Karl August Folkers (1906-1997). American Society for Nutritional Sciences, J. Nutr. 2001;131:2227-2230.
Palan et al., Plasma concentrations of coenzyme Q10 and tocopherols in cervical intraepithelial neoplasia and cervical cancer. Eur J Cancer Prev. Aug. 2003;12(4):321-6.
Panwar et al., Preparation, characterization, and in vitro release study of albendazole-encapsulated nanosize liposomes. Int J Nanomedicine. Mar. 9, 2010;5:101-8.
Peddinghaus et al., Evaluation of the Usage Pattern and Safety Profile of a Frozen Plasma Transfusion Protocol. Transfusion. 2009;49:159A, Abstract SP285.
Persaud et al., Apoptotic affect of Ubiquinone precursors in melanoma. Cancer Research. Cellular and Molecular Biology. AACR Annual Meeting. 2 pages. Abstract 3281. May 1, 2009.
Perumal et al., Combined efficacy of tamoxifen and coenzyme Q10 on the status of lipid peroxidation and antioxidants in DMBA induced breast cancer. Mol Cell Biochem. May 2005;273(1-2):151-60.
Perumal et al., Therapeutic effect of tamoxifen and energy-modulating vitamins on carbohydrate-metabolizing enzymes in breast cancer. Cancer Chemother Pharmacol. 2005 ul;56(1):105-14.
Pfaffl et al., Real-time RT-PCR quantification of insulin-like growth factor (IGF)-1, IGF-1 receptor, IGF-2, IGF-2 receptor, insulin receptor, growth hormone receptor, IGF-binding proteins 1, 2 and 3 in the bovine species. Domest Anim Endocrinol. Apr. 2002;22(2):91-102.
Pravst et al., Coenzyme Q10 contents in foods and fortification strategies. Crit Rev Food Sci Nutr. Apr. 2010;50(4):269-80.
Prostate-Specific Antigen (PSA) Test. Retrieved online at: http://www.cancer.gov/cancertopics/factsheet/detection/PSA. Mar. 18, 2009.
Rastogi, Analytical control of preservative labelling on skin creams. Contact Dermatitis. Dec. 2000;43(6):339-43. (Abstract only).
Recht et al., A Phase 1 Study of BPM31510 Plus Vitamin K in Subjects wtih High-grade Glioma that has Recurred on a Bevacizumab-containing Regimen. Neuro-Oncology. Nov. 2019;21(Suppl. 6):vi27, Abstract ACTR-59.
Riethdorf et al., Differential expression of CD66a (BGP), a cell adhesion molecule of the carcinoembryonic antigen family, in benign, premalignant, and malignant lesions of the human mammary gland. J Histochem Cytochem. Jul. 1997;45(7):957-63.
Roffe et al., Efficacy of coenzyme Q10 for improved tolerability of cancer treatments: a systematic review. J Clin Oncol. Nov. 1, 2004;22(21):4418-24.
Rydberg et al., Toll-like receptor agonists induce inflammation and cell death in a model of head and neck squamous cell carcinomas. Immunology. Sep. 2009;128(1 Suppl):e600-11.
Sander et al., Vesicle associated membrane protein (VAMP)-7 and VAMP-8, but not VAMP-2 or VAMP-3, are required for activation-induced degranulation of mature human mast cells. Eur J Immunol. Mar. 2008;38(3):855-63.
Scambia et al., Cathepsin D and epidermal growth factor in human breast cyst fluid. Br J Cancer. Nov. 1991;64(5):965-7.
Scotton et al., Analysis of CC chemokine and chemokine receptor expression in solid ovarian tumours. Br J Cancer. Sep. 14, 2001;85(6):891-7.
Seifried et al., The antioxidant conundrum in cancer. Cancer Res. Aug. 1, 2003;63(15):4295-8.
Shaoqiong et al., Related gene expressions in anti-keratinocyte aging induced by Ganoderma lucidum polysaccharides. J of Medical Colleges of PLA. 2008;23:167-175.
Shekelle et al., Effect of the supplemental use of antioxidants vitamin C, vitamin E, and coenzyme Q10 for the prevention and treatment of cancer. Evid Rep Technol Assess (Summ). Oct. 2003;(75):1-3.

(56) References Cited

OTHER PUBLICATIONS

Shen et al., Bioactive Components from the Mycelium of Antrodia salmonea. Journal of the Chinese Chemical Society. 2008;55:854-857.
Sheng et al., The efficacy of combining antiangiogenic agents with chemotherapy for patients with advanced non-small cell lung cancer who failed first-line chemotherapy: a systematic review and meta-analysis. PLoS One. Jun. 2, 2015;10(6):e0127306.
Shimada et al., Effect of high dose of pyridoxine on mammary tumorigenesis. Nutr Cancer. 2005;53(2):202-7.
Shimizu, Paclitaxel Pirarubicin Weekly. Japan J. Cancer and Chemotherapy, Jan. 2003;30:105-109.
Sieben et al., Differential Gene Expressionin Ovarian Tumors Reveals Dusp 4 and Serpina 5 as Key Regulators for Benign Behavior of Serous Borderline Tumors. J Clinical Oncology. Oct. 1, 2005;23(29):7275-7264.
Small Cell Lung Cancer Treatment (PDQ®)—National Cancer Institute. Retrieved online at: http://www.cancer.gov/cancertopics/pdq/treatment/small-cell-lung/healthprofessional. Jan. 20, 2012.
Soule et al., A human cell line from a pleural effusion derived from a breast carcinoma. J Natl Cancer Inst. Nov. 1973;51(5):1409-16.
Stafford et al., Meningioma radiosurgery: tumor control, outcomes, and complications among 190 consecutive patients. Neurosurgery. Nov. 2001;49(5):1029-37.
Sun et al., BPM31510 exploits differential redox vulnerabilities between normal and glioblastoma cells to mediate its anti-cancer effect. Molecular and Cellular Biology/Genetics. Abstract 3608, Jul. 1, 2019.
The National Cancer Institute, Coenzyme Q10 (PDQ.RTM.) Patient Version. Retrieved online at: http://www.cancer.gov/cancertopics/pdq/cam/coenzymeQ10/patient/allpages. 13 pages, Jul. 10, 2009.
Thibault et al., Phase I Study of Lovastatin, an Inhibitor of the Mevalonate Pathway, in Patients with Cancer. Clinical Cancer Research. Mar. 1996;2:483-491.
Tockman et al., Considerations in bringing a cancer biomarker to clinical application. Cancer Res. May 1, 1992;52(9 Suppl):2711s-2718s.
Todaro et al., Apoptosis resistance in epithelial tumors is mediated by tumor-cell-derived interleukin-4. Cell Death Differ. Apr. 2008;15(4):762-72.
Tsubaki et al., [Investigation of the preventive effect of CoQ10 against the side-effects of anthracycline antineoplastic agents]. Gan To Kagaku Ryoho. Jul. 1984;11(7):1420-7.
Tsuneki et al., Coenzyme Q10 prevents high glucose-induced oxidative stress in human umbilical vein endothelial cells. Eur J Pharmacol. Jul. 2, 2007;566(1-3):1-10.
UT Health Cancer Center, Clinical trial to study the safety and efficacy of MBG453 given alone and in combination with PDR001 in adults with advanced cancer. Retrieved online at: http://www.uthscsa.edu/pateint-care/ctrc/clinical-trial/HSC20150730HU. 3 pages, Jul. 30, 2015.
Verhoeff et al., Bevacizumab and dose-intense temozolomide in recurrent high-grade glioma. Ann Oncol. Aug. 2010;21(8):1723-7.
Vermeer, Vitamin K: the effect on health beyond coagulation—an overview. Food & Nutrition Research. 2012;56(5329):1-6.
Women's Health Update: Coenzyme Q10 and Breast Cancer. Retrieved online at: http://www.encognitive.com/node/13574 on Dec. 26, 2012. 4 pages.
Yagasaki et al., Clinical significance of E-cadherin and vimentin co-expression in breast cancer. Int J Oncol. Oct. 1996;9(4):755-61.
Yang et al., Efficiency Observations of 116 cases on Coenzyme Q10 as an Auxiliary Therapy for Treating Diabetes Combined with Coronary Heart Disease. Journal of Chinese Physician. Oct. 2002;4(10):1148-1149.
Yunis et al., Human pancreatic carcinoma (MIA PaCa-2) in continuous culture: sensitivity to asparaginase. Int J Cancer. Jan. 1977;19(1):128-35.
Zhang et al., Preparation and Physico-chemical Property of Coenzyme Q10 Submicroemulsion. China Pharmacy. 2007;18(19):1476-1478.
Zhao et al., The Clinical Application of Coenzyme Q10. Shandong Medical Journal. Jan. 31, 1996;36(1):52.
Zucher et al., Liposome drugs' loading efficiency: a working model based on loading conditions and drug's physicochemical properties. J Control Release. Oct. 1, 2009;139(1):73-80.
European Search Report for Application No. EP10775420, dated Feb. 18, 2013. 7 pages.
International Preliminary Report on Patentability for Application No. PCT/US2014/033402, dated Oct. 13, 2014.
International Search Report for Application No. PCT/US2007/068052, dated Apr. 15, 2008.
International Search Report for Application No. PCT/US2014/033402, dated Aug. 15, 2014.
U.S. Appl. No. 10/597,378, filed Aug. 21, 2008, U.S. Pat. No. 8,147,825.
U.S. Appl. No. 13/410,085, filed Mar. 1, 2012, U.S. Pat. No. 8,293,227.
U.S. Appl. No. 13/791,313, filed Mar. 8, 2013, U.S. Pat. No. 8,586,030.
U.S. Appl. No. 13/366,224, filed Feb. 3, 2012, U.S. Pat. No. 8,562,976.
U.S. Appl. No. 14/031,706, filed Sep. 19, 2013, U.S. Pat. No. 8,771,680.
U.S. Appl. No. 14/282,336, filed May 20, 2014, 2014-0255372.
U.S. Appl. No. 16/900,162, filed Jun. 12, 2020, 2021-0128453.
U.S. Appl. No. 17/712,326, filed Apr. 4, 2022, 2023-0149292.
U.S. Appl. No. 13/439,615, filed Apr. 4, 2012, 2012-0269867.
U.S. Appl. No. 15/376,243, filed Dec. 12, 2016, U.S. Pat. No. 10,373,477.
U.S. Appl. No. 16/444,296, filed Jun. 18, 2019, U.S. Pat. No. 11,452,699.
U.S. Appl. No. 14/248,313, filed Apr. 8, 2014, U.S. Pat. No. 10,933,032.
U.S. Appl. No. 17/141,499, filed Jan. 5, 2021, 2021-0369645.
U.S. Appl. No. 13/9077,726, filed May 31, 2013, 2014-0017317.
U.S. Appl. No. 15/289,770, filed Oct. 10, 2016, 2017-0216223.
U.S. Appl. No. 17/321,699, filed May 17, 2021, 2022-0096399.
U.S. Appl. No. 14/477,828, filed Sep. 4, 2014, U.S. Pat. No. 9,901,542.
U.S. Appl. No. 15/869,630, filed Jan. 12, 2018, U.S. Pat. No. 11,298,313.
U.S. Appl. No. 17/686,569, filed Mar. 4, 2022.
U.S. Appl. No. 15/656,986, filed Jul. 21, 2017, 2018-0021270.
U.S. Appl. No. 17/376,357, filed Jul. 15, 2021, 2022-0096400.
U.S. Appl. No. 15/353,724, filed Nov. 16, 2016, 2017-0189350.
U.S. Appl. No. 17/572,092, filed Jan. 10, 2022, 2022-0202741.
U.S. Appl. No. 16/653,787, filed Oct. 15, 2016, 2020-0138744.
U.S. Appl. No. 17/100,674, filed Nov. 20, 2020, 2021-0322339.
U.S. Appl. No. 12/778,094, filed May 11, 2010, 2011-0027247.
U.S. Appl. No. 14/171,419, filed Feb. 3, 2014, U.S. Pat. No. 9,896,731.
U.S. Appl. No. 15/862,856, filed Jan. 5, 2018, U.S. Pat. No. 10,351,915.
U.S. Appl. No. 16/421,788, filed May 24, 2019, U.S. Pat. No. 11,028,446.
U.S. Appl. No. 17/232,795, filed Apr. 16, 2021, 2022-0081720.
U.S. Appl. No. 12/777,902, filed May 11, 2010, U.S. Pat. No. 10,519,504.
U.S. Appl. No. 12/778,029, filed May 11, 2010, U.S. Pat. No. 9,205,064.
U.S. Appl. No. 14/940,614, filed Nov. 13, 2015, 2016-0145693.
U.S. Appl. No. 15/841,972, filed Dec. 14, 2017, 2018-0334721.
U.S. Appl. No. 16/819,811, filed Mar. 19, 2020, 2021-0332439.
U.S. Appl. No. 12/778,054, filed May 11, 2010, 2011-0020312.
U.S. Appl. No. 12/778,010, filed May 11, 2010, 2011-0123986.
U.S. Appl. No. 15/011,196, filed Jan. 29, 2016, 2017-0137879.
U.S. Appl. No. 15/837,505, filed Dec. 11, 2017, 2019-0010554.
U.S. Appl. No. 16/456,257, filed Jun. 28, 2019.
U.S. Appl. No. 16/805,557, filed Feb. 28, 2020, 2021-0002725.

* cited by examiner

METHODS OF TREATMENT OF TEMOZOLOMIDE-RESISTANT GLIOMA USING COENZYME Q10

RELATED APPLICATIONS

This application is a continuation of U.S. patent application Ser. No. 15/353,724, filed on Nov. 16, 2016 which, in turn, claims priority to U.S. Provisional Patent Application No. 62/256,107 filed on Nov. 16, 2015. The entire contents of each of the foregoing applications are incorporated herein by reference.

BACKGROUND

High Grade Gliomas, including anaplastic astrocytomas, anaplastic oligodendrogliomas and glioblastomas (GBM), are the most common and most aggressive primary brain tumors. Prognosis for patients with high-grade gliomas remains poor. The estimated median survival for patients with GBM is between 12 to 18 months. Recurrence after initial therapy with temozolomide and radiation is nearly universal. Since May 2009, the majority of patients in the US with an initial recurrence of high-grade glioma receive bevacizumab, a monoclonal antibody against vascular endothelial growth factor (VEGF), which is thought to prevent angiogenesis in these highly vascular tumors. Bevacizumab has response rates from 32-62% and has improved overall median survival in patients with recurrent high-grade gliomas (Chamberlain M. C., 2009, Neurology 72(8): 772-3). However, the response is short lived, and nearly 100% of patients eventually progress despite bevacizumab. No chemotherapeutic agent administered following progression through bevacizumab has made a significant impact on survival (Shen et al., 2012, Journal of Cancer Therapy 3: 491-503). Therefore, patients with high-grade gliomas who have progressed through bevacizumab represent a population in dire need of a feasible and tolerable treatment.

SUMMARY OF THE INVENTION

The present invention is based, at least in part, on the discovery that mitochondrial Complex II activity is linked to Coenzyme Q10-induced cytotoxicity and apoptosis. Complex II, also known as succinate-coenzyme Q reductase (SDH, EC 1.3.5.1), is one of the five complexes involved in oxidative phosphorylation in the inner mitochondrial membrane. It catalyzes electron transfer from succinate to the electron carrier, ubiquinone. The product ubiquinol is utilized by complex III in the respiratory chain. Because Complex II activity has been shown to increase in TMZ-resistant glioblastomas (GB), and TMZ-resistant GB appears to be more reliant on Complex II-driven respiration, TMZ-resistant GB is expected to be especially sensitive to Coenzyme Q10 compounds. Moreover, other cancers having elevated Complex II activity or which are more reliant on Complex II-driven respiration would similarly be expected to be particularly sensitive to Coenzyme Q10 compounds.

In one aspect, the invention provides a method of treating a glioma in a subject, wherein the subject has failed treatment for the glioma with temozolomide (TMZ), the method comprising administering to the subject a composition comprising a Coenzyme Q10 compound, thereby treating the glioma in the subject.

In one embodiment, the glioma is a glioblastoma.

In one embodiment, the glioma is a refractory glioma. In one embodiment, the glioma is refractory to an anti-cancer agent selected from the group consisting of TMZ and bevacizumab.

In one embodiment, the glioma exhibits increased Complex II activity relative to a glioma that is not TMZ-resistant.

In one embodiment, the subject has failed treatment for the glioma with at least one additional anti-cancer agent. In one embodiment, the at least one additional anti-cancer agent is a chemotherapeutic agent. In one embodiment, the at least one additional anti-cancer agent is an anti-angiogenic agent. In one embodiment, the at least one additional anti-cancer agent is bevacizumab.

In one embodiment, the failed treatment comprises tumor growth during or after treatment with the TMZ.

In one embodiment, the failed treatment comprises tumor growth during or after treatment with the at least one additional anti-cancer agent.

In one embodiment, the subject demonstrates a clinical benefit as a result of administration of the composition comprising the Coenzyme Q10 compound. In one embodiment, the clinical benefit is selected from the group consisting of stable disease per RECIST 1.1 criteria, partial response per RECIST 1.1 criteria, and complete response per RECIST 1.1 criteria. In one embodiment, the subject achieves or maintains stable disease by RECIST 1.1 criteria as a result of administration of the composition comprising the Coenzyme Q10 compound. In one embodiment, the subject achieves or maintains a partial response by RECIST 1.1 criteria as a result of administration of the composition comprising the Coenzyme Q10 compound. In one embodiment, the subject achieves or maintains a complete response by RECIST 1.1 criteria as a result of administration of the composition comprising the Coenzyme Q10 compound.

In one embodiment, the glioma comprises a Stage I tumor. In one embodiment, the glioma comprises a Stage II tumor. In one embodiment, the glioma comprises a Stage III tumor. In one embodiment, the glioma comprises a Stage IV tumor.

In one embodiment, the glioma is a low grade glioma. In one embodiment, the glioma is a high grade glioma. In one embodiment, the glioma is metastatic.

In one embodiment, the subject has further failed treatment with a chemotherapeutic agent selected from the group consisting of carmustine (BCNU), thalidomide, irinotecan, lomustine (CCNU), procarbazine, vincristine, and a platinum compound.

In one embodiment, the Coenzyme Q10 compound is Coenzyme Q10.

In one embodiment, the composition comprising the Coenzyme Q10 compound is administered one time per week, two times per week, or three times per week. In one embodiment, the composition comprising the Coenzyme Q10 compound is administered at least one time per week, at least two times per week, or at least three times per week.

In one embodiment, the Coenzyme Q10 is administered at a dose selected from the group consisting of at least 15.5 mg/kg/day (24 hours), at least 16.7 mg/kg/day (24 hours), at least 19.0 mg/kg/day (24 hours), at least 20.5 mg/kg/day (24 hours), at least 22.0 mg/kg/day (24 hours), at least 25.0 mg/kg/day (24 hours), at least 27.3 mg/kg/day (24 hours), at least 29.3 mg/kg/day (24 hours), at least 33.4 mg/kg/day (24 hours), at least 36.7 mg/kg/day (24 hours), at least 34.1 mg/kg/day (24 hours), at least 41.7 mg/kg/day (24 hours), at least 42.5 mg/kg/day (24 hours), at least 45.7 mg/kg/day (24 hours), at least 52.0 mg/kg/day (24 hours), at least 53.1 mg/kg/day (24 hours), at least 57 mg/kg/day (24 hours), at least 64.9 mg/kg/day (24 hours), at least 66.7 mg/kg/day (24 hours), at least 71.7 mg/kg/day (24 hours), at least 81.5 mg/kg/day (24 hours), at least 88.8 mg/kg/day (24 hours), at least 95.3 mg/kg/day (24 hours), at least 108.5 mg/kg/day (24 hours), at least 117.9 mg/kg/day (24 hours), at least 126.7 mg/kg/day (24 hours), at least 144.2 mg/kg/day (24 hours), at least 156.7 mg/kg/day (24 hours), at least 168.3 mg/kg/day (24 hours), at least 191.6 mg/kg/day (24 hours), at least 208.5 mg/kg/day (24 hours), at least 224 mg/kg/day (24 hours), and at least 254.9 mg/kg/day (24 hours).

In one embodiment, the Coenzyme Q10 is administered at a dose selected from the group consisting of at least 100 mg/kg/week, at least 132 mg/kg/week, at least 171 mg/kg/week, at least 215 mg/kg/week, at least 274 mg/kg/week, at least 430 mg/kg/week, at least 572 mg/kg/week, at least 760 mg/kg/week, at least 1010 mg/kg/week, and at least 1344 mg/kg/week.

In one embodiment, the Coenzyme Q10 is administered at a dose selected from the group consisting of about 100 mg/kg/week, about 132 mg/kg/week, about 171 mg/kg/week, about 215 mg/kg/week, about 274 mg/kg/week, about 430 mg/kg/week, about 572 mg/kg/week, about 760 mg/kg/week, about 1010 mg/kg/week, and about 1344 mg/kg/week.

In one embodiment, the Coenzyme Q10 is administered at a dose selected from the group consisting of at least 50 mg/kg/dose, at least 66 mg/kg/dose, at least 88 mg/kg/dose, at least 110 mg/kg/dose, at least 137 mg/kg/dose, at least 171 mg/kg/dose, at least 215 mg/kg/dose, at least 286 mg/kg/dose, at least 380 mg/kg/dose, at least 505 mg/kg/dose, and at least 672 mg/kg/dose.

In one embodiment, the Coenzyme Q10 is administered at a dose selected from the group consisting of about 50 mg/kg/dose, about 66 mg/kg/dose, about 88 mg/kg/dose, about 110 mg/kg/dose, about mg/kg/dose, about 171 mg/kg/dose, about 215 mg/kg/dose, about 286 mg/kg/dose, about 380 mg/kg/dose, about 505 mg/kg/dose, and about 672 mg/kg/dose.

In one embodiment, the dose of Coenzyme Q10 is administered by continuous infusion over about 72 hours.

In one embodiment, the composition comprising the Coenzyme Q10 compound is administered by injection or infusion. In one embodiment, the composition comprising the Coenzyme Q10 compound is administered intravenously. In one embodiment, the composition comprising the Coenzyme Q10 is administered by continuous infusion.

In one embodiment, the composition comprising the Coenzyme Q10 is administered by continuous infusion for at least 48 hours, at least 72 hours, at least 96 hours, at least 120 hours, or at least 144 hours.

In one embodiment, at least 12 doses, at least 15 doses, at least 26 doses, or at least 33 doses of the composition comprising the Coenzyme Q10 compound are administered to the subject.

In one embodiment, the subject has failed 8 or fewer chemotherapeutic regimens. In one embodiment, the subject has failed 5 or fewer chemotherapeutic regimens.

In one embodiment, the composition comprising the Coenzyme Q10 compound is administered topically. In one embodiment, the composition comprising the Coenzyme Q10 compound is administered orally. In one embodiment, the composition comprising the Coenzyme Q10 compound is administered by inhalation.

In one embodiment, the subject is human.

In one embodiment, the composition comprising the Coenzyme Q10 compound is administered to the subject with an additional anti-cancer agent. In one embodiment, the additional anti-cancer agent is a chemotherapeutic agent. In one embodiment, the additional anti-cancer agent is an anti-angiogenic agent. In one embodiment, the additional anti-cancer agent is bevacizumab, TMZ or a combination thereof.

In another aspect, the invention provides a method of treating a cancer that exhibits increased Complex II activity in a subject, the method comprising administering to the subject a composition comprising a Coenzyme Q10 compound, thereby treating the cancer that exhibits increased Complex II activity in the subject.

In one embodiment, the subject has failed treatment for the cancer with at least one anti-cancer agent. In one embodiment, the at least one anti-cancer agent is a chemotherapeutic agent. In one embodiment, the at least one anti-cancer agent is an anti-angiogenic agent.

In one embodiment, the subject demonstrates a clinical benefit as a result of administration of the composition comprising the Coenzyme Q10 compound. In one embodiment, the clinical benefit is selected from the group consisting of stable disease per RECIST 1.1 criteria, partial response per RECIST 1.1 criteria, and complete response per RECIST 1.1 criteria.

In one embodiment, the cancer is metastatic.

In one embodiment, the Coenzyme Q10 compound is Coenzyme Q10.

In one embodiment, the composition comprising the Coenzyme Q10 compound is administered one time per week, two times per week, or three times per week. In one embodiment, the composition comprising the Coenzyme Q10 compound is administered at least one time per week, at least two times per week, or at least three times per week.

In one embodiment, the Coenzyme Q10 is administered at a dose selected from the group consisting of at least 15.5 mg/kg/day (24 hours), at least 16.7 mg/kg/day (24 hours), at least 19.0 mg/kg/day (24 hours), at least 20.5 mg/kg/day (24 hours), at least 22.0 mg/kg/day (24 hours), at least 25.0 mg/kg/day (24 hours), at least 27.3 mg/kg/day (24 hours), at least 29.3 mg/kg/day (24 hours), at least 33.4 mg/kg/day (24 hours), at least 36.7 mg/kg/day (24 hours), at least 34.1 mg/kg/day (24 hours), at least 41.7 mg/kg/day (24 hours), at least 42.5 mg/kg/day (24 hours), at least 45.7 mg/kg/day (24 hours), at least 52.0 mg/kg/day (24 hours), at least 53.1 mg/kg/day (24 hours), at least 57 mg/kg/day (24 hours), at least 64.9 mg/kg/day (24 hours), at least 66.7 mg/kg/day (24 hours), at least 71.7 mg/kg/day (24 hours), at least 81.5 mg/kg/day (24 hours), at least 88.8 mg/kg/day (24 hours), at least 95.3 mg/kg/day (24 hours), at least 108.5 mg/kg/day (24 hours), at least 117.9 mg/kg/day (24 hours), at least 126.7 mg/kg/day (24 hours), at least 144.2 mg/kg/day (24 hours), at least 156.7 mg/kg/day (24 hours), at least 168.3 mg/kg/day (24 hours), at least 191.6 mg/kg/day (24 hours), at least 208.5 mg/kg/day (24 hours), at least 224 mg/kg/day (24 hours), and at least 254.9 mg/kg/day (24 hours).

In one embodiment, the Coenzyme Q10 is administered at a dose selected from the group consisting of at least 100 mg/kg/week, at least 132 mg/kg/week, at least 171 mg/kg/week, at least 215 mg/kg/week, at least 274 mg/kg/week, at least 430 mg/kg/week, at least 572 mg/kg/week, at least 760 mg/kg/week, at least 1010 mg/kg/week, and at least 1344 mg/kg/week.

In one embodiment, the Coenzyme Q10 is administered at a dose selected from the group consisting of about 100 mg/kg/week, about 132 mg/kg/week, about 171 mg/kg/week, about 215 mg/kg/week, about 274 mg/kg/week, about 430 mg/kg/week, about 572 mg/kg/week, about 760 mg/kg/week, about 1010 mg/kg/week, and about 1344 mg/kg/week.

In one embodiment, the Coenzyme Q10 is administered at a dose selected from the group consisting of at least 50 mg/kg/dose, at least 66 mg/kg/dose, at least 88 mg/kg/dose, at least 110 mg/kg/dose, at least 137 mg/kg/dose, at least 171 mg/kg/dose, at least 215 mg/kg/dose, at least 286 mg/kg/dose, at least 380 mg/kg/dose, at least 505 mg/kg/dose, and at least 672 mg/kg/dose.

In one embodiment, the Coenzyme Q10 is administered at a dose selected from the group consisting of about 50 mg/kg/dose, about 66 mg/kg/dose, about 88 mg/kg/dose, about 110 mg/kg/dose, about mg/kg/dose, about 171 mg/kg/dose, about 215 mg/kg/dose, about 286 mg/kg/dose, about 380 mg/kg/dose, about 505 mg/kg/dose, and about 672 mg/kg/dose.

In one embodiment, the dose of Coenzyme Q10 is administered by continuous infusion over about 72 hours.

In one embodiment, the composition comprising the Coenzyme Q10 compound is administered by injection or infusion. In one embodiment, the composition comprising the Coenzyme Q10 compound is administered intravenously. In one embodiment, the composition comprising the Coenzyme Q10 is administered by continuous infusion.

In one embodiment, the composition comprising the Coenzyme Q10 is administered by continuous infusion for at least 48 hours, at least 72 hours, at least 96 hours, at least 120 hours, or at least 144 hours.

In one embodiment, at least 12 doses, at least 15 doses, at least 26 doses, or at least 33 doses of the composition comprising the Coenzyme Q10 compound are administered to the subject.

In one embodiment, the subject has failed 8 or fewer chemotherapeutic regimens. In one embodiment, the subject has failed 5 or fewer chemotherapeutic regimens.

In one embodiment, the composition comprising the Coenzyme Q10 compound is administered topically. In one embodiment, the composition comprising the Coenzyme Q10 compound is administered orally. In one embodiment, the composition comprising the Coenzyme Q10 compound is administered by inhalation.

In one embodiment, the subject is human.

In one embodiment, the composition comprising the Coenzyme Q10 compound is administered to the subject with an additional anti-cancer agent. In one embodiment, the additional anti-cancer agent is a chemotherapeutic agent. In one embodiment, the additional anti-cancer agent is an anti-angiogenic agent. In one embodiment, the additional anti-cancer agent is bevacizumab, TMZ or a combination thereof.

In another aspect, the invention provides a composition comprising a Coenzyme Q10 compound for practicing any of the foregoing methods.

In yet another aspect, the invention provides a composition comprising a Coenzyme Q10 compound in the preparation of a medicament for carrying out any of the foregoing methods.

In still another aspect, the invention provides a kit for practicing any of the foregoing methods.

Accordingly, the present invention provides, in certain aspects, a method of treating a glioma in a subject, wherein the subject has failed treatment for the glioma with temozolomide (TMZ), the method comprising administering to the subject a composition comprising a Coenzyme Q10 compound, thereby treating the glioma in the subject. In certain embodiments, the subject has failed treatment for the glioma with at least one additional chemotherapeutic agent. In certain embodiments, the at least one additional chemotherapeutic agent is bevacizumab. In certain embodiments, the failed treatment comprises tumor growth during or after treatment with the TMZ. In certain embodiments, the failed treatment comprises tumor growth during or after treatment with the at least one additional chemotherapeutic agent.

In certain embodiments, the subject demonstrates a clinical benefit as a result of administration of the composition comprising the Coenzyme Q10 compound. In certain embodiments, the clinical benefit is selected from the group consisting of stable disease per RECIST 1.1 criteria, partial response per RECIST 1.1 criteria, and complete response per RECIST 1.1 criteria. In certain embodiments, the subject achieves or maintains stable disease by RECIST 1.1 criteria as a result of administration of the composition comprising the Coenzyme Q10 compound. In certain embodiments, the subject achieves or maintains a partial response by RECIST 1.1 criteria as a result of administration of the composition comprising the Coenzyme Q10 compound. In certain embodiments, the subject achieves or maintains a complete response by RECIST 1.1 criteria as a result of administration of the composition comprising the Coenzyme Q10 compound. In certain embodiments, the subject does not exhibit a dose limiting toxicity in response to administration of the composition comprising the Coenzyme Q10 compound. In certain embodiments, the subject does not exhibit a grade III toxicity as a result of administration of the composition comprising the Coenzyme Q10 compound. In certain embodiments, the subject does not exhibit a grade IV toxicity as a result of administration of the composition comprising the Coenzyme Q10 compound.

In certain embodiments, the glioma comprises a Stage I tumor. In certain embodiments, the glioma comprises a Stage II tumor. In certain embodiments, the glioma comprises a Stage III tumor. In certain embodiments, the glioma comprises a Stage IV tumor. In certain embodiments, the glioma is a low grade glioma. In certain embodiments, the glioma is a high grade glioma. In certain embodiments, the glioma is metastatic. In certain embodiments, the glioma is a glioblastoma. In certain embodiments, the glioma is a refractory glioma, e.g., refractory glioblastoma. In certain embodiments, the refractory glioma (e.g. glioblastoma) is initially unresponsive to chemo- or radiation therapy. In certain embodiments the refractory glioma (e.g. glioblastoma) is initially response to chemo- or radiation therapy, but becomes unresponsive to chemo- or radiation therapy over time. In certain embodiments, the glioma is refractory to TMZ. In certain embodiments, the glioma is refractory to bevacizumab. In certain embodiments, the glioma is refractory to TMZ and bevacizumab. In certain embodiments, the subject has further failed treatment with a chemotherapeutic agent selected from the group consisting of carmustine (BCNU), thalidomide, irinotecan, lomustine (CCNU), procarbazine, vincristine, and a platinum compound.

In certain embodiments, the Coenzyme Q10 compound is Coenzyme Q10. In certain embodiments, the composition comprising the Coenzyme Q10 compound is administered at least one time per week. In certain embodiments, the composition comprising the Coenzyme Q10 compound is administered at least two times per week. In certain embodiments, the composition comprising the Coenzyme Q10 compound is administered at least three times per week. In certain embodiments, the composition comprising the Coenzyme Q10 compound is administered one time per week. In certain embodiments, the composition comprising the Coenzyme Q10 compound is administered two times per week. In certain embodiments, the composition comprising the Coenzyme Q10 compound is administered three times per week.

In certain embodiments, the Coenzyme Q10 is administered at a dose selected from the group consisting of about 11.8 mg/kg/day (24 hours), about 12.5 mg/kg/day (24 hours), about 14.4 mg/kg/day (24 hours), about 15.6 mg/kg (24 hours), about 16.5 mg/kg/day (24 hours), about 19 mg/kg/day (24 hours), about 20.4 mg/kg/day (24 hours), about 22 mg/kg/day (24 hours), about 25 mg/kg/day (24 hours), about 27.5 mg/kg/day (24 hours), about 29.3 mg/kg/day (24 hours), about 33 mg/kg/day (24 hours), about 34.2 mg/kg/day (24 hours), about 36.7 mg/kg/day (24 hours), about 41.7 mg/kg/day (24 hours), 42.8 mg/kg/day (24 hours), about 44 mg/kg/day (24 hours), about 45.7 mg/kg/day (24 hours), about 51.9 mg/kg/day (24 hours), about 53.8 mg/kg/day (24 hours), about 55 mg/kg/day (24 hours), about 57 mg/kg/day (24 hours), about 58.7 mg/kg/day (24 hours), about 64.8 mg/kg/day (24 hours), about 66.7 mg/kg/day (24 hours), about 68.5 mg/kg/day (24 hours), about 71.7 mg/kg/day (24 hours), about 73.4 mg/kg/day (24 hours), about 81.5 mg/kg/day (24 hours), about 85.5 mg/kg/day (24 hours), about 91.7 mg/kg/day (24 hours), about 107.5 mg/kg/day (24 hours), about 114.6 mg/kg/day (24 hours), and about 143.3 mg/kg/day (24 hours).

In certain embodiments, the Coenzyme Q10 is administered at a dose selected from the group consisting of about 38 mg/kg/week, about 50 mg/kg/week, about 66 mg/kg/week, about 76 mg/kg/week, about 88 mg/kg/week, about 100 mg/kg/week, about 110 mg/kg/week, about 132 mg/kg/week, about 137 mg/kg/week, about 171 mg/kg/week, about 176 mg/kg/week, about 215 mg/kg/week, about 220 mg/kg/week, about 274 mg/kg/week, about 342 mg/kg week, and about 430 mg/kg/week.

In certain embodiments, the Coenzyme Q10 is administered at a dose of at least 50 mg/kg/dose. In certain embodiments, the Coenzyme Q10 is administered at a dose of at least 75 mg/kg/dose. In certain embodiments, the Coenzyme Q10 is administered at a dose of at least 100 mg/kg/dose. In certain embodiments, the Coenzyme Q10 is administered at a dose of at least 125 mg/kg/dose. In certain embodiments, the Coenzyme Q10 is administered at a dose of at least 150 mg/kg/dose. In certain embodiments, the Coenzyme Q10 is administered at a dose of at least 200 mg/kg/dose. In certain embodiments, the composition comprising the Coenzyme Q10 compound is administered at a dose that does not result in a Grade III toxicity in the subject. In certain embodiments, the composition comprising the Coenzyme Q10 compound is administered at a dose that does not result in a Grade IV toxicity to the subject.

In certain embodiments, at least 12 doses of the composition comprising the Coenzyme Q10 compound are administered to the subject. In certain embodiments, at least 15 doses of the composition comprising the Coenzyme Q10 compound are administered to the subject. In certain embodiments, at least 26 doses of the composition comprising the Coenzyme Q10 compound are administered to the subject. In certain embodiments, at least 33 doses of the composition comprising the Coenzyme Q10 compound are administered to the subject. In certain embodiments, the subject has failed 8 or fewer chemotherapeutic regimens. In certain embodiments, the subject has failed 5 or fewer chemotherapeutic regimens.

In certain embodiments, the composition comprising the Coenzyme Q10 compound is administered by injection or infusion. In certain embodiments, the composition comprising the Coenzyme Q10 compound is administered intravenously. In certain embodiments, the composition comprising the Coenzyme Q10 compound is administered topically. In certain embodiments, the composition comprising the Coenzyme Q10 compound is administered orally. In certain embodiments, the composition comprising the Coenzyme Q10 compound is administered by inhalation. In certain embodiments, the subject is human.

In certain embodiments, the composition comprising Coenzyme Q10 is administered to the subject with an additional agent. In certain embodiments, the additional agent is a chemotherapeutic agent.

In certain aspects, the present invention relates to a composition comprising a Coenzyme Q10 compound for practicing any one of the methods described above.

In certain aspects, the present invention relates to use of a composition comprising a Coenzyme Q10 compound in the preparation of a medicament for carrying out the methods described above.

In certain aspects, the present invention relates to a kit for practicing any one of the methods described above.

Other embodiments are provided infra.

BRIEF DESCRIPTION OF THE DRAWINGS

FIGS. 9A, 9B and 9C show the coronal sections 27 days, 34 days, and 103 days after C6 implantation, respectively. CoQ10 treatment was discontinued 34 days after C6 implantation.

FIGS. 10A, 10B and 10C show the coronal sections 27 days, 34 days, and 103 days after C6 implantation, respectively.

DETAILED DESCRIPTION AND PREFERRED EMBODIMENTS

I. Definitions

Figure 1A:
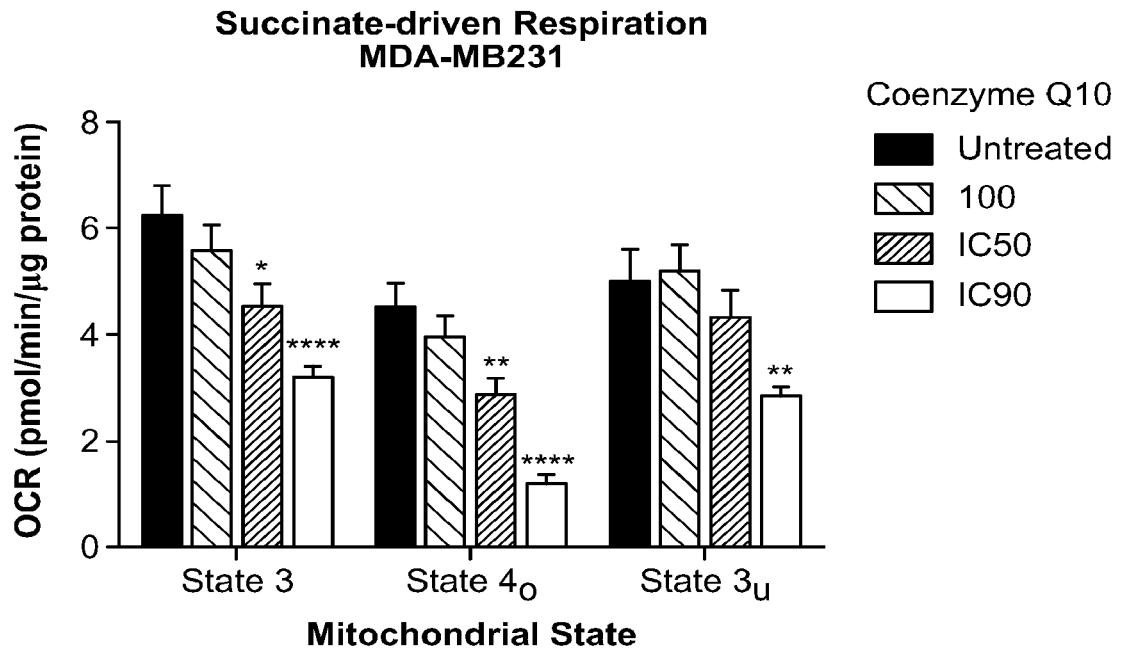
FIGS. 1A and 1B show the oxygen consumption rate (OCR) during various states of succinate-fueled mitochondrial respiration in the triple-negative breast cancer cell line MDA-MB231 (1A) and the mutant K-Ras-driven pancreatic cancer cell line MIA PaCa-2 (1B) treated with different concentrations of Coenzyme Q10. MDA-MB231 cells were treated with 100 μM, 155 μM (IC50) or 310 μM (IC90) Coenzyme Q10. MIA PaCa-2 cells were treated with 100 μM, 137 μM (IC50) or 274 μM (IC90) Coenzyme Q10. Mitochondrial states shown are State 3, State 4o (o=oligomycin), and State 3u (u=uncoupled).

The terms "administer", "administering" or "administration" include any method of delivery of a pharmaceutical composition or agent into a subject's system or to a particular region in or on a subject. In certain embodiments, the agent is delivered orally. In certain embodiments, the agent is administered parenterally. In certain embodiments, the agent is delivered by injection or infusion. In certain embodiments, the agent is delivered topically including transmucosally. In certain embodiments, the agent is delivered by inhalation. In certain embodiments of the invention, an agent is administered by parenteral delivery, including, intravenous, intramuscular, subcutaneous, intramedullary injections, as well as intrathecal, direct intraventricular, intraperitoneal, intranasal, or intraocular injections. In one embodiment, the compositions provided herein may be administered by injecting directly to a tumor. In some embodiments, the formulations of the invention may be administered by intravenous injection or intravenous infusion. In certain embodiments, the formulation of the invention can be administered by continuous infusion. In certain embodiments, administration is not oral. In certain embodiments, administration is systemic. In certain embodiments, administration is local. In some embodiments, one or more routes of administration may be combined, such as, for example, intravenous and intratumoral, or intravenous and peroral, or intravenous and oral, intravenous and topical, or intravenous and transdermal or transmucosal. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

"Adverse events" or "AEs" are characterized by grade depending on the severity. Some AE (e.g., nausea, low blood counts, pain, reduced blood clotting) can be treated so that the specific chemotherapeutic regimen can be continued or resumed. Some adverse events (e.g., loss of cardiac, liver, or kidney function; nausea) may not be treatable, requiring termination of treatment with the drug. Determination of AE grade and appropriate interventions can be determined by those of skill in the art. Common Terminology Criteria for Adverse Events v4.0 (CTCAE) (Publish Date: May 28, 2009) provide a grading scale for adverse events as follows:

Grade 1 Mild; asymptomatic or mild symptoms; clinical or diagnostic observations only; intervention not indicated.

Grade 2 Moderate; minimal, local or noninvasive intervention indicated; limiting age-appropriate instrumental activities of daily life (ADL).

Grade 3 Severe or medically significant but not immediately life-threatening; hospitalization or prolongation of hospitalization indicated; disabling, limiting self care ADL.

Grade 4 Life-threatening consequences; urgent intervention indicated.

Grade 5 Death related to adverse event.

An "anti-cancer agent" is understood as a drug used for the treatment of cancer. Anti-cancer agents include, but are not limited to, small molecules, hormones and hormone analogs, and biologics (e.g., antibodies, peptide drugs, nucleic acid drugs).

A "cancer therapeutic regimen" is a clinically accepted dosing protocol for the treatment of cancer that includes administration of one or more anti-cancer agents to a subject in specific amounts on a specific schedule.

The terms "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features.

A "cancer that exhibits increased Complex II activity" refers to a cancer that exhibits increased mitochondrial Complex II enzyme activity relative to a corresponding control cancer. For example, a cancer that is resistant to an anti-cancer agent (e.g. temozolomide or bevacizumab) may exhibit increased Complex II activity relative to a corresponding cancer that is sensitive to the anti-cancer agent. In some embodiments, a cancer that originates in a particular tissue (e.g., brain, breast, lung, prostate, pancreatic esophageal, gastric, bladder, appendiceal or colon tissue) may exhibit increased Complex II activity relative to the average level of Complex II activity of corresponding cancers originating in the same tissue.

As used herein, "co-administration" or "combination therapy" is understood as administration of two or more active agents using separate formulations or a single pharmaceutical formulation, or consecutive administration in any order such that, there is a time period while both (or all) active agents simultaneously exert their biological activities. Co-administration does not require that the agents are administered at the same time, at the same frequency, or by the same route of administration. As used herein, "co-administration" or "combination therapy" includes administration of a composition comprising a Coenzyme Q10 compound with one or more additional anti-cancer agents, e.g., chemotherapeutic agents, or administration of two or more CoQ10 compounds. Examples of anticancer agents, including chemotherapeutic agents, are provided herein.

As used herein, "continuous infusion" is understood as administration of a dose of the formulation continuously for at least 24 hours. Continuous administration is typically facilitated by use of a pump, either an implantable or external pump. A formulation can be administered by continuous infusion in multiple, separated doses, with a break of one or more days between continuous infusion doses.

As used herein, a "formulation" is understood as an active ingredient, e.g., CoQ10, a metabolite of CoQ10, a biosynthetic precursor of CoQ10, or a CoQ10 related compound, in combination with any pharmaceutically acceptable carrier. Formulations can include, but are not limited to, aqueous formulations, liposomal formulations, suspensions, emulsions, microemulsions, nanoemulsions, nanosuspensions, formulations for specific routes of administration, such as cream, lotion, and ointment formulations for topical administration, solid formulations for oral administration, and liquid formulations for injection or inhalation.

A "glioma" is a type of tumor that starts in the brain or spine and arises from glial cells. The most common site of gliomas is the brain. Gliomas make up about 30% of all brain and central nervous system tumors and 80% of all malignant brain tumors. Gliomas include, but are not limited to, ependymomas, astrocytomas (e.g. glioblastoma, a malignant astrocytoma), oligodendrogliomas, brainstem gliomas, optic nerve gliomas, and mixed gliomas (e.g. oligoastrocytomas) which contain cells from different types of glia. In a particular embodiment, the glioma is a glioblastoma. Glioblastoma is also known as glioblastoma multiforme and grade IV astrocytoma. Gliomas may be characterized as low-grade gliomas or high-grade gliomas. Low-grade gliomas are well-differentiated (not anaplastic) and tend to exhibit benign tendencies and portend a better prognosis for the patient. However, they have a uniform rate of recurrence and increase in grade over time so should be classified as malignant. High-grade gliomas are undifferentiated or anaplastic, malignant, and carry a worse prognosis. In some embodiments, the glioma (e.g. glioblastoma) is malignant. In some embodiments the glioma (e.g. glioblastoma) is non-malignant, i.e., benign.

As used herein, a "pharmaceutically acceptable" component is one that is suitable for use with humans and/or animals without undue adverse side effects (such as toxicity, irritation, and allergic response) commensurate with a reasonable benefit/risk ratio.

A "solid tumor" is a tumor that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. The tumor does not need to have measurable dimensions.

Specific criteria for the staging of cancer are dependent on the specific cancer type based on tumor size, histological characteristics, tumor markers, and other criteria known by those of skill in the art. Generally, cancer stages can be described as follows:

Stage 0 Carcinoma in situ

Stage I, Stage II, and Stage III Higher numbers indicate more extensive disease: Larger tumor size and/or spread of the cancer beyond the organ in which it first developed to nearby lymph nodes and/or tissues or organs adjacent to the location of the primary tumor Stage IV The cancer has spread to distant tissues or organs As used herein, the terms "treat," "treating" or "treatment" refer, preferably, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) state of disease, amelioration or palliation of the disease state, diminishing rate of or time to progression, and remission (whether partial or total). "Treatment" of a glioma (e.g. glioblastoma) can also mean prolonging survival as compared to expected survival in the absence of treatment. Treatment need not be curative. In certain embodiments, treatment includes one or more of a decrease in pain or an increase in the quality of life (QOL) as judged by a qualified individual, e.g., a treating physician, e.g., using accepted assessment tools of pain and QOL. In certain embodiments, treatment does not include one or more of a decrease in pain or an increase in the quality of life (QOL) as judged by a qualified individual, e.g., a treating physician, e.g., using accepted assessment tools of pain and QOL.

RECIST criteria are clinically accepted assessment criteria used to provide a standard approach to solid tumor measurement and provide definitions for objective assessment of change in tumor size for use in clinical trials. Such criteria can also be used to monitor response of an individual undergoing treatment for a solid tumor. The RECIST 1.1 criteria are discussed in detail in Eisenhauer et al., New response evaluation criteria in solid tumors: Revised RECIST guideline (version 1.1). Eur. J. Cancer. 45:228-247, 2009, which is incorporated herein by reference. Response criteria for target lesions include:

Complete Response (CR): Disappearance of all target lesions. Any pathological lymph nodes (whether target or non-target) must have a reduction in short axis to <10 mm.

Partial Response (PR): At least a 30% decrease in the sum of diameters of target lesion, taking as a reference the baseline sum diameters.

Progressive Diseases (PD): At least a 20% increase in the sum of diameters of target lesions, taking as a reference the smallest sum on the study (this includes the baseline sum if that is the smallest on the study). In addition to the relative increase of 20%, the sum must also demonstrate an absolute increase of at least 5 mm. (Note: the appearance of one or more new lesions is also considered progression.)

Stable Disease (SD): Neither sufficient shrinkage to qualify for PR nor sufficient increase to qualify for PD, taking as a reference the smallest sum diameters while on study.

RECIST 1.1 criteria also consider non-target lesions which are defined as lesions that may be measureable, but need not be measured, and should only be assessed qualitatively at the desired time points. Response criteria for non-target lesions include:

Complete Response (CR): Disappearance of all non-target lesions and normalization of tumor marker levels. All lymph nodes must be non-pathological in size (<10 mm short axis).

Non-CR/Non-PD: Persistence of one or more non-target lesion(s) and/or maintenance of tumor marker level above the normal limits.

Progressive Disease (PD): Unequivocal progression (emphasis in original) of existing non-target lesions. The appearance of one or more new lesions is also considered progression. To achieve "unequivocal progression" on the basis of non-target disease, there must be an overall level of substantial worsening of non-target disease such that, even in the presence of SD or PR in target disease, the overall tumor burden has increased sufficiently to merit discontinuation of therapy. A modest "increase" in the size of one or more non-target lesions is usually not sufficient to qualify for unequivocal progression status. The designation of overall progression solely on the basis of change in non-target disease in the face of SD or PR in target disease will therefore be extremely rare.

A "subject who has failed treatment for the glioma" or a "subject who has failed a cancer therapeutic regimen for the glioma" is a subject with a glioma (e.g glioblastoma) that does not respond, or ceases to respond to treatment with a cancer therapeutic regimen per RECIST 1.1 criteria (see, Eisenhauer et al., 2009 and as discussed above), i.e., does not achieve a complete response, partial response, or stable disease in the target lesion; or does not achieve complete response or non-CR/non-PD of non-target lesions, either during or after completion of the cancer therapeutic regimen, either alone or in conjunction with surgery and/or radiation therapy which, when possible, are often clinically indicated in conjunction with anti-cancer agents. A failed cancer therapeutic regime results in, e.g., tumor growth, increased tumor burden, and/or tumor metastasis. A failed cancer therapeutic regimen as used herein includes a treatment regimen that was terminated due to a dose limiting toxicity, e.g., a grade III or a grade IV toxicity that cannot be resolved to allow continuation or resumption of treatment with the cancer therapeutic agent or regimen that caused the toxicity. A failed cancer therapeutic regimen includes a treatment regimen that does not result in at least stable disease for all target and non-target lesions for an extended period, e.g., at least 1 month, at least 2 months, at least 3 months, at least 4 months, at least 5 months, at least 6 months, at least 12 months, at least 18 months, or any time period less than a clinically defined cure. A failed cancer therapeutic regimen includes a treatment regimen that results in progressive disease of at least one target lesion during treatment with the chemotherapeutic agent, or results in progressive disease less than 2 weeks, less than 1 month, less than two months, less than 3 months, less than 4 months, less than 5 months, less than 6 months, less than 12 months, or less than 18 months after the conclusion of the treatment regimen, or less than any time period less than a clinically defined cure.

A failed cancer therapeutic regimen does not include a treatment regimen wherein the subject treated for a glioma (e.g. glioblastoma) achieves a clinically defined cure, e.g., 5 years of complete response after the end of the treatment regimen, and wherein the subject is subsequently diagnosed with a distinct cancer, e.g., more than 5 years, more than 6 years, more than 7 years, more than 8 years, more than 9 years, more than 10 years, more than 11 years, more than 12 years, more than 13 years, more than 14 years, or more than 15 years after the end of the treatment regimen. For example, a subject who suffered from a glioma (e.g. glioblastoma) may develop cancer later in life after being cured of the glioma. In such a subject, the cancer therapeutic regimen to treat the glioma is considered to have been successful.

A "refractory glioma" is a glioma (e.g. glioblastoma) which is either initially unresponsive to a cancer therapeutic regimen or radiation therapy, or which is initially responsive to a cancer therapeutic regimen or radiation therapy but becomes unresponsive to the cancer therapeutic regimen or radiation therapy over time.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this disclosure.

As used herein, the term "survival" refers to the continuation of life of a subject which has been treated for a disease or condition, e.g., a glioma (e.g. glioblastoma). The time of survival can be defined from an arbitrary point such as time of entry into a clinical trial, time from completion or failure or an earlier treatment regimen, time from diagnosis, etc.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the term "therapeutically effective amount" refers to an amount, e.g., of a compound of the present disclosure, effective to yield the desired therapeutic response or sufficient to treat a disease in a subject. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives. The "therapeutically effective amount" will vary depending on the compound, the disease and its severity and the age, weight, etc., of the patient to be treated. A therapeutically effective amount can be administered in one or more administrations.

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

II. Coenzyme Q10 Compounds

Coenzyme Q10 (CoQ10) compounds are intended to include a class of CoQ10 related compounds. Coenzyme Q10 compounds effective for the methods described herein include CoQ10, a metabolite of CoQ10, a biosynthetic precursor of CoQ10, an analog of CoQ10, a derivative of CoQ10, and CoQ10 related compounds. An analog of CoQ10 includes analogs having no or at least one isoprenyl repeats. CoQ10 has the following structure:

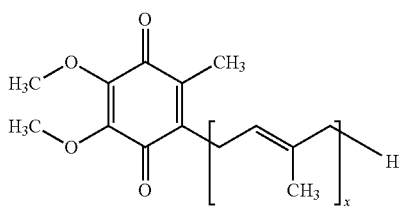

wherein x is 10. In the instant invention, CoQ10 compounds can include derivatives of CoQ10 in which x is any number of isoprenyl units from 4-10, or any number of isoprenyl units from 6-10, or any number of isoprenyl units from 8-10, or 9-10 isoprenyl units. CoQ10 includes the fully oxidized version, also known as ubiquinone, the partially oxidized version, also known as semiquinone or ubisemiquinone, or the fully reduced version, also known as ubiquinol; or any mixtures or combinations thereof. In certain embodiments, the composition comprising Coenzyme Q10 for use in the treatment methods herein (e.g., treatment of a glioma, e.g. glioblastoma) is ubiquinone or fully oxidized CoQ10. In certain embodiments, the composition comprising Coenzyme Q10 for use in the treatment methods herein (e.g., treatment of a glioma, e.g. glioblastoma) is ubiquinol.

In certain embodiments of the present invention, the therapeutic agent is Coenzyme Q10 (CoQ10). Coenzyme Q10, also referred to herein as CoQ10, is also known as ubiquinone, or ubidecarenone. CoQ10 is art-recognized and further described in International Publication No. WO 2005/069916 (Appln. No. PCT/US2005/001581), WO 2008/116135 (Appln. No. PCT/US08/57786), WO2010/132507 (Appln. No. PCT/US2010/034453), WO 2011/112900 (Appln. No. PCT/US2011/028042), and WO2012/174559 (Appln. No. PCT/US2012/043001) the entire contents of each of which are expressly incorporated by reference herein. CoQ10 is one of a series of polyprenyl 2,3-dimethoxy-5-methylbenzoquinone (ubiquinone) present in the mitochondrial electron transport systems of eukaryotic cells. Human cells produce CoQ10 exclusively and it is found in cell and mitochondrial membranes of all human cells, with the highest levels in organs with high energy requirements, such as the liver and the heart. The body pool of CoQ10 has been estimated to be about 2 grams, of which more than 50% is endogenous. Approximately 0.5 grams of CoQ10 is required from the diet or biosynthesis each day. CoQ10 is produced in ton quantities from the worldwide supplement market and can be obtained from Kaneka, with plants in Pasadena, Texas and Takasagoshi, Japan.

Coenzyme Q10 related compounds include, but are not limited to, benzoquinones, isoprenoids, farnesols, farnesyl acetate, farnesyl pyrophosphate, 1-phenylalanine, d-phenylalanine, dl-phenylalanine, 1-tyrosine, d-tyrosine, dl-tyrosine, 4-hydroxy-phenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C8 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like. In certain embodiments, such agents can be used for the treatment of certain cancers as provided herein, e.g, a glioma (e.g. glioblastoma), according to the methods provided herein.

Metabolites and biosynthetic precursors of CoQ10 include, but are not limited to, those compounds that are formed between the chemical/biological conversion of tyrosine and acetyl-CoA to ubiquinol. Intermediates of the coenzyme biosynthesis pathway include tyrosine, acetyl-CoA, 3-hexaprenyl-4-hydroxybenzoate, 3-hexaprenyl-4,5-dihydroxybenzoate, 3-hexaprenyl-4-hydroxy-5-methoxy-benzoate, 2-hexaprenyl-6-methoxy-1,4-benzoquinone, 2-hexaprenyl-3-methyl-6-methoxy-1,4-benzoquinone, 2-hexaprenyl-3-methyl-5-hydroxy-6-methoxy-1,4-benzoquinone, 3-Octaprenyl-4-hydroxybenzoate, 2-octaprenylphenol, 2-octaprenyl-6-metholxyphenol, 2-octaprenyl-3-methyl-6-methoxy-1,4-benzoquinone, 2-octaprenyl-3-methyl-5-hydroxy-6-methoxy-1,4-benzoquinone, 2-decaprenyl-3-methyl-5-hydroxy-6-methoxy-1,4-benzoquinone, 2-decaprenyl-3-methyl-6-methoxy-1,4-benzoquinone, 2-decaprenyl-6-methoxy-1,4-benzoquinone, 2-decaprenyl-6-methoxyphenol, 3-decaprenyl-4-hydroxy-5-methoxybenzoate, 3-decaprenyl-4,5-dihydroxybenzoate, 3-decaprenyl-4-hydroxybenzoate, 4-hydroxy phenylpyruvate, 4-hydroxyphenyllactate, 4-hydroxy-benzoate, 4-hydroxycinnamate, and hexaprenydiphosphate. In certain embodiments, such agents can be used for the treatment of certain cancers as provided herein, e.g., a glioma (e.g. glioblastoma), according to the methods provided herein.

III. Compositions

The present disclosure provides compositions comprising a Coenzyme Q10 compound for the treatment of certain cancers as provided herein, e.g, gliomas (e.g. glioblastomas). The compositions of the present disclosure can be administered to a patient either by themselves, or in pharmaceutical compositions where it is mixed with suitable carriers or excipient(s). In treating a patient exhibiting a disorder of interest, e.g., glioma, e.g. glioblastoma, a therapeutically effective amount of the composition comprising a Coenzyme Q10 compound is administered. A therapeutically effective dose refers to that amount of the compound which results in at least stable disease or a prolongation of survival in a patient.

Suitable routes of administration of the present compositions of the invention may include parenteral delivery, including, intravenous, intramuscular, subcutaneous, intramedullary injections, as well as intrathecal, direct intraventricular, intraperitoneal, intranasal, or intraocular injections, just to name a few. In one embodiment, the compositions provided herein may be administered by injecting directly to a tumor. In some embodiments, the formulations of the invention may be administered by intravenous injection or intravenous infusion. In some embodiments, the formulation is administered by continuous infusion. In one embodiment, the compositions of the invention are administered by intravenous injection. In one embodiment, the compositions of the invention are administered by intravenous infusion. In one embodiment, the Coenzyme Q10 is administered by continuous infusion, e.g., intravenous continuous infusion. In some embodiments, the Coenzyme Q10 is administered by continuous infusion for at least 36 hours, at least 48 hours, at least 60 hours, at least 72 hours, at least 84 hours, at least 96 hours, at least 108 hours, at least 120 hours, at least 132 hours, or at least 144 hours. In some embodiments, the continuous infusion is administered for about 36 hours, about 48 hours, about 60 hours, about 72 hours, about 84 hours, about 96 hours, about 108 hours, about 120 hours, about 132 hours, or about 144 hours. In a particular embodiment, the continuous infusion is administered for at least 72 hours, or for about 72 hours (about 3 days).

Where the route of administration is, for example intravenous infusion, embodiments are provided herein where the IV infusion comprises the active agent, e.g., CoQ10, at approximately a 40 mg/mL concentration. Where the composition is administered by IV infusion, it can be diluted in a pharmaceutically acceptable aqueous solution such as phosphate buffered saline or normal saline. In some embodiments, one or more routes of administration may be combined, such as, for example, intravenous and intratumoral, or intravenous and peroral, or intravenous and oral, or intravenous and topical, transdermal, or transmucosal.

In some embodiments, suitable routes of administration of the present compositions of the invention include topical, inhalable, or oral administration.

The compositions described herein may be administered to a subject in any suitable formulation. These include, for example, liquid, semi-solid, and solid dosage forms, such as liquid solutions (e.g., injectable and infusible solutions), dispersions or suspensions, tablets, pills, powders, creams, lotions, liniments, ointments, or pastes, drops for administration to the eye, ear or nose, liposomes, and suppositories. The preferred form depends on the intended mode of administration and therapeutic application.

In certain embodiments, a composition comprising a Coenzyme Q10 compound may be prepared with a carrier that will protect against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

For example, a composition comprising a Coenzyme Q10 compound can be formulated for parenteral delivery, e.g., for subcutaneous, intravenous, intramuscular, or intratumoral injection. The compositions may be administered in a single bolus, multiple injections, or by continuous infusion (for example, intravenously or by peritoneal dialysis). For parenteral administration, the compositions may be formulated in a sterilized pyrogen-free form.

Use of pharmaceutically acceptable carriers to formulate the Coenzyme Q10 compounds disclosed herein, for the practice of the present invention, into dosages suitable for systemic administration is within the scope of the present disclosure. With proper choice of carrier and suitable manufacturing practice, the compositions of the present disclosure, in particular, those formulated as solutions, may be administered parenterally, such as by intravenous injection.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices may be desirable. The data obtained from these cell culture assays and animal studies can be used in formulating a range of dosage for use in human. The dosage of such compounds may be within a range of circulating concentrations that include the ED50 with little or no toxicity. The dosage may vary within this range depending upon the dosage form employed and the route of administration utilized.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for intravenous administration may be in the form of solutions of colloidal dispersion.

Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

IV. Formulations

The active agent, e.g., a CoQ10 compound, can be delivered in any pharmaceutically acceptable carrier for the desired route of administration. As used herein, formulations including CoQ10 compounds are formulated for any route of administration unless otherwise clearly indicated. In preferred embodiments, the formulations are for administration by injection, infusion, or topical administration. In certain embodiments, the CoQ10 compounds are not delivered orally.

Preferred therapeutic formulations for use in the methods of the invention comprise the active agent (e.g., a CoQ10 compound) in a microparticle formation, e.g., for intravenous administration. Such intravenous formulations are provided, for example, in WO2011/112900 (Appln. No. PCT/US2011/028042), the entire contents of which are expressly incorporated herein by reference, and an exemplary intravenous formulation as described in WO2011/112900 (Appln. No. PCT/US2011/028042). Through high pressure homogenization, active agent (e.g., a CoQ10 compound) particles are reduced to produce particles that are small enough to pass through a 200-nm sterilizing filter. Particles that are small enough to pass through a 200-nm sterilizing filter can be injected intravenously. These particles are much smaller than blood cells and therefore will not embolize capillaries. Red blood cells for example are 6-micron×2-micron disks. The particles are dispersed to and are encased or surrounded by a stabilizing agent. While not wishing to be bound by any theory, it is believed that the stabilizing agents are attracted to the hydrophobic therapeutic agent such that the dispersed particles of the hydrophobic therapeutic agent are surrounded by the stabilizing agent forming a suspension or an emulsion. The dispersed particles in the suspension or emulsion comprises a stabilizing agent surface and a core consisting of the hydrophobic therapeutic agent, e.g., a CoQ10 compound, in a solid particulate form (suspension) or in an immiscible liquid form (emulsion). The dispersed particles can be entrenched in the lipophilic regions of a liposome.

Dispersed colloidal systems permit a high drug load in the formulation without the use of co-solvents. Additionally, high and relatively reproducible plasma levels are achieved without the dependence on endogenous low-density lipoprotein carriers. More importantly, the formulations allow sustained high drug levels in solid tumors due to the passive accumulation of the colloidal particles of the hydrophobic therapeutic agent.

A preferred intravenous formulation substantially comprises a continuous phase of water and dispersed solids (suspension) or dispersed immiscible liquid (emulsion). Dispersed colloidal systems, in which the particles are composed largely of the active agent (drug) itself, can often deliver more drug per unit volume than continuous solubilizing systems, if the system can be made adequately stable.

As the formulation medium, the aqueous solution may include Hank's solution, Ringer's solution, phosphate buffered saline (PBS), physiological saline buffer or other suitable salts or combinations to achieve the appropriate pH and osmolarity for parenterally delivered formulations. Aqueous solutions can be used to dilute the formulations for administration to the desired concentration. For example, aqueous solutions can be used to dilute a formulation for intravenous administration from a concentration of about 4% w/v to a lower concentration to facilitate administration of lower doses of CoQ10. The aqueous solution may contain substances which increase the viscosity of the solution, such as sodium carboxymethyl cellulose, sorbitol, or dextran.

The active agent (e.g., a CoQ10 compound) is dispersed in the aqueous solution such that a colloidal dispersion is formed wherein the nano-dispersion particles of the hydrophobic therapeutic agent are covered or encased or encircled by the dispersion stabilizing agents to form nano-dispersions of the active agent (e.g., a CoQ10 compound) particles. The nano-dispersed active agent (e.g., a CoQ10 compound) particles have a core formed of the hydrophobic therapeutic agent that is surrounded by the stabilizing agent. Similarly, in certain aspects, the stabilizing agent is a phospholipid having both a hydrophilic and lipophilic portion. The phospholipids form liposomes or other nanoparticles upon homogenization. In certain aspects these liposomes are bi-layered unilamellar liposomes while in other embodiments the liposomes are bi-layered multi-lamellar liposomes. The dispersed active agent (e.g., a CoQ10 compound) particles are dispersed in the lipophilic portion of the bi-layered structure of the liposome formed from the phospholipids. In certain other aspects the core of the liposome, like the core of the nano-dispersion of active agent (e.g., a CoQ10 compound) particles, is formed of the hydrophobic therapeutic agent and the outer layer is formed of the bi-layered structure of the phospholipid. In certain embodiments the colloidal dispersions are treated by a lyophilization process whereby the nanoparticle dispersion is converted to a dry powder.

In some embodiments, the formulation for injection or infusion used is a 4% sterile aqueous colloidal dispersion containing CoQ10 in a nanosuspension as prepared in WO2011/112900, the entire contents of which are incorporated herein by reference. In certain embodiments, the formulation includes an aqueous solution; a hydrophobic active agent, e.g., CoQ10, a CoQ10 precursor or metabolite or a CoQ10 related compound, dispersed to form a colloidal nano-dispersion of particles; and at least one of a dispersion stabilizing agent and an opsonization reducer; wherein the colloidal nano-dispersion of the active agent is dispersed into nano-dispersion particles having a mean size of less than 200-nm.

In certain embodiments, the dispersion stabilizing agent includes, but is not limited to, pegylated castor oil, Cremphor® EL, Cremophor® RH 40, Pegylated vitamin E, Vitamin E TPGS, and Dimyristoylphosphatidyl choline (DMPC).

In certain embodiments, the opsonization reducer is a poloxamer or a poloxamines.

In certain embodiments, the colloidal nano-dispersion is a suspension or an emulsion. Optionally, a colloidal nano-dispersion is in a crystalline form or a super-cooled melt form.

In certain embodiments, the formulation for injection or infusion includes a lyoprotectant such as a nutritive sugar including, but not limited to, lactose, mannose, maltose, galactose, fructose, sorbose, raffinose, neuraminic acid, glucosamine, galactosamine, N-methylglucosamine, mannitol, sorbitol, arginine, glycine and sucrose, or any combination thereof.

In certain embodiments, the formulation for injection or infusion includes an aqueous solution; a hydrophobic active agent dispersed to form a colloidal nano-dispersion of particles; and at least one of a dispersion stabilizing agent and an opsonization reducer. The colloidal nano-dispersion of the active agent is dispersed into nano-dispersion particles having sizes of less than 200-nm. In some embodiments the dispersion stabilizing agent is selected from natural or semisynthetic phospholipids. For example, suitable stabilizing agents include polyethoxylated (a/k/a pegylated) castor oil (Cremophor® EL), polyethoxylated hydrogenated castor oil (Cremophor® RH 40), Tocopherol polyethylene glycol succinate (Pegylated vitamin E, Vitamin E TPGS), Sorbitan fatty acid esters (Spans®), Bile acids and bile-acid salts or Dimyristoylphosphatidyl choline (DMPC). In some embodiments the stabilizing agent is DMPC.

In certain embodiments the formulation is suitable for parenteral administration, including intravenous, intraperitoneal, orthotopical, intracranial, intramuscular, subcutaneous, intramedullary injections, as well as intrathecal, direct intraventricular, intranasal, or intraocular injections. In certain embodiments, the formulation contains CoQ10, dimyristoyl-phophatidylcholine, and poloxamer 188 in a ratio of 4:3:1.5 respectively that is designed to stabilize the nanosuspension of the particles. In some embodiments, the formulation includes a phosphate buffer saline solution which contains sodium phosphate dibasic, potassium phosphate monobasic, potassium chloride, sodium chloride and water for injection. In certain embodiments, the 4% sterile aqueous colloidal dispersion containing CoQ10 in a nanosuspension is diluted in the phosphate buffered saline solution provided, e.g., 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, or other appropriate ratio bracketed by any two of the values.

In some embodiments, the formulation is a topical formulation. Topical formulations of CoQ10 compounds are provided, for example in WO2010/132507 (PCT Appln. No. PCT/US2010/034453), WO2008116135 (PCT Appln. No. PCT/US2008/116135), and WO2005/069916 (PCT Appln. PC/US2005/001581), the entire contents of each of which are expressly incorporated herein by reference.

Formulations suitable for topical administration include liquid or semi-liquid preparations suitable for penetration through the skin, such as liniments, lotions, creams, ointments or pastes, and drops suitable for administration to the eye, ear, or nose. Drops according to the present disclosure may include sterile aqueous or oily solutions or suspensions and may be prepared by dissolving the active ingredient in a suitable aqueous solution of a bactericidal and/or fungicidal agent and/or any other suitable preservative, and in some embodiments including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present disclosure include those suitable for application to the skin or eye. An eye lotion may include a sterile aqueous solution optionally containing a bactericide and may be prepared by methods similar to those for the preparation of drops. Lotions or liniments for application to the skin may also include an agent to hasten drying and to cool the skin, such as an alcohol, and/or a moisturizer such as glycerol or an oil such as castor oil or arachis oil.

Creams, ointments or pastes useful in the methods of the invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may include hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as siliceous silicas, and other ingredients such as lanolin, may also be included.

In some embodiments, the remaining component of a topical delivery vehicle may be water or a water phase, in embodiments purified, e.g. deionized, water, glycerine, propylene glycol, ethoxydiglycol, phenoxyethanol, and cross linked acrylic acid polymers. Such delivery vehicle compositions may contain water or a water phase in an amount of from about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle may have a viscosity of at least about 30 centipoises.

Topical formulations can also include an oil phase including, for example, oil phase which, in turn, may include emollients, fatty alcohols, emulsifiers, combinations thereof, and the like. For example, an oil phase could include emollients such as C12-15 alkyl benzoates (commercially available as FINSOLV™ TN from Finetex Inc. (Edison, N.J.)), capric-caprylic triglycerides (commercially available from Huls as MIGLYOL™ 812), and the like. Other suitable emollients which may be utilized include vegetable derived oils (corn oil, safflower oil, olive oil, macadamian nut oil, etc.); various synthetic esters, including caprates, linoleates, dilinoleates, isostearates, fumarates, sebacates, lactates, citrates, stearates, palmitates, and the like; synthetic medium chain triglycerides, silicone oils or polymers; fatty alcohols such as cetyl alcohol, stearyl alcohol, cetearyl alcohol, lauryl alcohol, combinations thereof, and the like; and emulsifiers including glyceryl stearate, PEG-100 stearate, Glyceryl Stearate, Glyceryl Stearate SE, neutralized or partially neutralized fatty acids, including stearic, palmitic, oleic, and the like; vegetable oil extracts containing fatty acids, Ceteareth®-20, Ceteth®-20, PEG-150 Stearate, PEG-8 Laurate, PEG-8 Oleate, PEG-8 Stearate, PEG-20 Stearate, PEG-40 Stearate, PEG-150 Distearate, PEG-8 Distearate, combinations thereof, and the like; or other non-polar cosmetic or pharmaceutically acceptable materials used for skin emolliency within the purview of those skilled in the art, combinations thereof, and the like.

Topical formulations can also include a liposomal concentrate including, for example, a phospholipid such as lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof, at least one lipophilic bioactive agent, and at least one solubilizer. The liposomal concentrate may be in combination with at least one pharmaceutically acceptable carrier possessing at least one permeation enhancer in an amount from about 0.5% by weight to about 20% by weight of the composition. The phospholipid may present in the composition in an amount from about 2% to about 20% by weight of the composition and the bioactive agent may be present in an amount from about 0.5% to about 20% by weight of the composition.

Transdermal skin penetration enhancers can also be used to facilitate delivery of CoQ10. Illustrative are sulfoxides such as ethoxydiglycol, 1,3-butylene glycol, isopentyl diol, 1,2-pentane diol, propylene glycol, 2-methyl propan-2-ol, propan-2-ol, ethyl-2-hydroxypropanoate, hexan-2,5-diol, di(2-hydroxypropyl)ether, pentan-2,4-diol, acetone, polyoxyethylene(2)methyl ether, 2-hydroxypropionic acid, 2-hydroxyoctanoic acid, propan-1-ol, 1,4 dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, diisopropyl adipate, diisopropyl sebacate, dibutyl sebacate, diethyl sebacate, dimethyl sebacate, dioctyl sebacate, dibuyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hyroxyoctanoic acid, dimethyl sulphoxide, methyl sufonyl methane, n,n-dimethyl acetamide, n,n-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, and combinations thereof.

Solubilizers, particularly for topical administration can include, but are not limited to, polyoxyalkylene dextrans, fatty acid esters of saccharose, fatty alcohol ethers of oligoglucosides, fatty acid esters of glycerol, fatty acid esters of polyoxyethylenes, polyethoxylated fatty acid esters of sorbitan, fatty acid esters of poly(ethylene oxide), fatty alcohol ethers of poly(ethylene oxide), alkylphenol ethers of poly(ethylene oxide), polyoxyethylene-polyoxypropylene block copolymers, ethoxylated oils, and combinations thereof.

Topical formulations can include emollients, including, but not limited to, C12-15 alkyl benzoates, capric-caprylic triglycerides, vegetable derived oils, caprates, linoleates, dilinoleates, isostearates, fumarates, sebacates, lactates, citrates, stearates, palmitates, synthetic medium chain triglycerides, silicone oils, polymers and combinations thereof; the fatty alcohol is selected from the group consisting of cetyl alcohol, stearyl alcohol, cetearyl alcohol, lauryl alcohol and combinations thereof and the emulsifier is selected from the group consisting of glyceryl stearate, polyethylene glycol 100 stearate, neutralized fatty acids, partially neutralized fatty acids, polyethylene glycol 150 stearate, polyethylene glycol 8 laurate, polyethylene glycol oleate, polyethylene glycol 8 stearate, polyethylene glycol 20 stearate, polyethylene glycol 40 stearate, polyethylene glycol 150 distearate, polyethylene glycol 8 distearate, and combinations thereof.

Topical formulations can include a neutralization phase comprising one or more of water, amines, sodium lactate, and lactic acid.

The water phase can further optionally include a permeation enhancer optionally in combination with a viscosity modifier selected from the group consisting of cross linked acrylic acid polymers, pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed, rice starch, corn starch, potato starch, wheat starch, algae extract, dextran, succinoglucan, carboxymethyl starch, methylhydroxypropyl starch, sodium alginate, alginic acid propylene glycol esters, sodium polyacrylate, polyethylacrylate, polyacrylamide, polyethyleneimine, bentonite, aluminum magnesium silicate, laponite, hectonite, and anhydrous silicic acid.

Topical formulations can also include a pigment such as titanium dioxide.

In an embodiment, a topical formulation for use in the methods of the invention includes an oil phase comprising C12-15 alkyl benzoates or capric/caprylic triglyceride, cetyl alcohol, stearyl alcohol, glyceryl stearate, and polyethylene glycol 100 stearate, in an amount of from about 5% to about 20% by weight of the composition; a water phase comprising glycerin, propylene glycol, ethoxydiglycol, phenoxyethanol, water, and a crosslinked acrylic acid polymer, in an amount of from about 60 to about 80% by weight of the composition; a neutralization phase comprising water, triethanolamine, sodium lactate, and lactic acid, in an amount of from about 0.1% to about 15% by weight of the composition; a pigment comprising titanium dioxide in an amount of from about 0.2% to about 2% by weight of the composition; and a liposomal concentrate comprising a polyethoxylated fatty acid ester of sorbitan, coenzyme Q10, a phosphatidylcholine lecithin, phenoxyethanol, propylene glycol, and water, in an amount of from about 0.1% to about 30% by weight of the composition, wherein the propylene glycol and ethoxydiglycol are present in a combined amount of from 3% by weight to about 15% by weight of the composition and the coenzyme Q10 is present in an amount of from about 0.75% by weight to about 10% by weight of the composition. Other formulations for use in the methods of the invention are provided, for example, in WO2008/116135 (PCT Application No. PCT/US08/57786), and in WO2010/132507 (PCT/US2010/034453), the entire contents of each of which are expressly incorporated herein by reference.

In one embodiment, a topical formulation for use in the methods of the invention is a 3% CoQ10 cream as described in US 2011/0027247, the entire contents of which are incorporated by reference herein. In one embodiment, the 3% CoQ10 comprises: (1) a phase A having C12-15 alkyl benzoate or capric/caprylic triglyceride at about 4.0% w/w of the composition, cetyl alcohol at about 2.00% w/w of the composition, stearyl alcohol at about 1.5% w/w, glyceryl stearate and PEG-100 at about 4.5% w/w; (2) a phase B having glycerin at about 2.00% w/w, propylene glycol at about 1.5% w/w, ethoxydiglycol at about 5.0% w/w, phenoxyethanol at about 0.475% w/w, a carbomer dispersion at about 40% w/w, purified water at about 16.7% w/w; (3) a phase C having triethanolamine at about 1.3% w/w, lactic acid at about 0.5% w/w, sodium lactate solution at about 2.0% w/w, water at about 2.5% w/w; (4) a phase D having titanium dioxide at about 1.0% w/w; and (5) a phase E having CoQ10 21% concentrate at about 15.0% w/w.

A CoQ10 21% concentrate composition (phase E in above 3% cream) can be prepared by combining phases A and B as described below. Phase A includes Ubidecarenone USP (CoQ10) at 21% w/w and polysorbate 80 NF at 25% w/w. Phase B includes propylene glycol USP at 10.00% w/w, phenoxyethanol NF at 0.50% w/w, lecithin NF (PHOSPHOLIPON 85G) at 8.00% w/w and purified water USP at 35.50% w/w. All weight percentages are relative to the weight of the entire CoQ10 21% concentrate composition. The percentages and further details are listed in the following table.

TABLE 1

| Phase | Trade Name | INCI Name | Percent |
|---|---|---|---|
| A | RITABATE 80 | POLYSORBATE 80 | 25.000 |
| A | UBIDECARENONE | UBIQUINONE | 21.000 |
| B | PURIFIED WATER | WATER | 35.500 |
| B | PROPYLENE GLYCOL | PROPYLENE GLYCOL | 10.000 |
| B | PHENOXYETHANOL | PHENOXYETHANOL | 0.500 |
| B | PHOSPHOLIPON 85G | LECITHIN | 8.000 |
| Totals | | | 100.000 |

The phenoxyethanol and propylene glycol are placed in a suitable container and mixed until clear. The required amount of water is added to a second container (Mix Tank 1). Mix Tank 1 is heated to between 45 and 55° C. while being mixed. The phenoxyethanol/propylene glycol solution is added to the water and mixed until it was clear and uniform. When the contents of the water phase in Mix Tank 1 are within the range of 45 to 55° C., Phospholipon G is added with low to moderate mixing. While avoiding any foaming, the contents of Mix Tank 1 is mixed until the Phospholipon 85G was uniformly dispersed. The polysorbate 80 is added to a suitable container (Mix Tank 2) and heated to between 50 and 60° C. The Ubidecarenone is then added to Mix Tank 2. While maintaining the temperature at between 50 and 60° C. Mix Tank 2 is mixed until all the Ubidecarenone is dissolved. After all the Ubidecarenone has been dissolved, the water phase is slowly transferred to Mix Tank 2. When all materials have been combined, the contents are homogenized until dispersion is smooth and uniform. While being careful not to overheat, the temperature is maintained at between 50 and 60° C. The homogenization is then stopped and the contents of Mix Tank 2 are transferred to a suitable container for storage.

In some embodiments, a formulation for any route of administration for use in the invention may include from about 0.001% to about 20% (w/w) of CoQ10, more preferably between about 0.01% and about 15% and even more preferably between about 0.1% to about 10% (w/w) of CoQ10. In certain embodiments, a formulation for any route of administration for use in the invention may include from about 1% to about 10% (w/w) of CoQ10. In certain embodiments, a formulation for any route of administration for use in the invention may include from about 2% to about 8% (w/w) of CoQ10. In certain embodiments, a formulation for any route of administration for use in the invention may include from about 2% to about 7% (w/w) of CoQ10. In certain embodiments, a formulation for any route of administration for use in the invention may include from about 3% to about 6% (w/w) of CoQ10. In certain embodiments, a formulation for any route of administration for use in the invention may include from about 3% to about 5% (w/w) of CoQ10. In certain embodiments, a formulation for any route of administration for use in the invention may include from about 3.5% to about 4.5% (w/w) of CoQ10. In certain embodiments, a formulation for any route of administration for use in the invention may include from about 3.5% to about 5% (w/w) of CoQ10. In one embodiment a formulation includes about 4% (w/w) of CoQ10. In one embodiment a formulation includes about 8% (w/w) of CoQ10. In one embodiment a formulation includes about 3% (w/w) of CoQ10. In various embodiments, the formulation includes about 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% (w/w) of CoQ10, or any range bracketed by any two values recited. In certain embodiments, the formulations can be prepared as a percent weight to volume rather than a percent weight to weight. Depending on the formulation, the concentration of CoQ10 may be the same, or about the same in the w/w and the w/v percent formulations. CoQ10 can be obtained from Kaneka Q10 as Kaneka Q10 (USP UBIDECARENONE) in powdered form (Pasadena, Texas, USA). CoQ10 used in the methods exemplified herein have the following characteristics: residual solvents meet USP 467 requirement; water content is less than 0.0%, less than 0.05% or less than 0.2%; residue on ignition is 0.0%, less than 0.05%, or less than 0.2%; heavy metal content is less than 0.002%, or less than 0.001%; purity of between 98-100% or 99.9%, or 99.5%.

In certain embodiments, the concentration of CoQ10 in the formulation is 1 mg/mL to 150 mg/mL. In one embodiment, the concentration of CoQ10 in the formulation is 5 mg/mL to 125 mg/mL. In one embodiment, the concentration of CoQ10 in the formulation is 10 mg/mL to 100 mg/mL. In one embodiment, the concentration of CoQ10 in the formulation is 20 mg/mL to 90 mg/mL. In one embodiment, the concentration of CoQ10 is 30 mg/mL to 80 mg/mL. In one embodiment, the concentration of CoQ10 is 30 mg/mL to 70 mg/mL. In one embodiment, the concentration of CoQ10 is 30 mg/mL to 60 mg/mL. In one embodiment, the concentration of CoQ10 is 30 mg/mL to 50 mg/mL. In one embodiment, the concentration of CoQ10 is 35 mg/mL to 45 mg/mL. It should be understood that additional ranges having any one of the foregoing values as the upper or lower limits are also intended to be part of this invention, e.g., 10 mg/mL to 50 mg/mL, or 20 mg/mL to 60 mg/mL.

In certain embodiments, the concentration of CoQ10 in the formulation is about 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90 or 95 mg/mL. In one embodiment, the concentration of CoQ10 in the formulation is about 50 mg/mL. In one embodiment, the concentration of CoQ10 in the formulation is about 60 mg/mL. In one embodiment, the concentration of CoQ10 in the formulation is about 30 mg/mL. In a preferred embodiment, the concentration of CoQ10 in the formulation is about 40 mg/mL. It should be understood that ranges having any one of these values as the upper or lower limits are also intended to be part of this invention, e.g. between 37 mg/mL and 47 mg/mL, or between 31 mg/mL and 49 mg/mL.

It is understood that formulations can similarly be prepared containing CoQ10 precursors, metabolites, and related compounds.

V. Methods of Treatment

In certain aspects, the invention relates to a method of treating a cancer that exhibits increased Complex II activity in a subject, the method comprising administering to the subject a composition comprising a Coenzyme Q10 compound, thereby treating the cancer in the subject.

The cancer that exhibits increased Complex II activity may be, for example, a cancer that has failed treatment with at least one anti-cancer agent. The at least one anti-cancer agent may include, but is not limited to, a chemotherapeutic agent and an anti-angiogenic agent. In a particular embodiment, the anti-cancer agent is temozolomide or bevacizumab. In some embodiments, the cancer that exhibits increased Complex II activity may be a metastatic cancer. In some embodiments, the cancer that exhibits increased Complex II activity exhibits at least 10%, 20%, 30%, 40%, 50%, 60%, 70%, 80%, 90%, 100%, or more, e.g., at least 125%, 150%, 175% or 200% of the Complex II activity of TMZ-resistant glioma cells derived from TMZ-sensitive U251 cells as described by Oliva et al. (2010, J Biol. Chem. 285(51): 39759-39767) using a method for determining Complex II activity described below.

Methods for determining Complex II activity in a cancer cell are known in the art and are described, for example, in: Oliva et al., 2010, J Biol. Chem. 285(51): 39759-39767; Darley-Usmar, V. M., et al., 1987, Mitochondria: A Practical Approach, pp. 113-152, IRL Press at Oxford University Press, Oxford; and Ragan, C. I., et al., 1987, Mitochondria: A Practical Approach, pp. 79-112, IRL Press at Oxford University Press, Oxford, each of which is incorporated by reference herein in its entirety. For example, Complex II activity may be determined by purifying the Complex II enzyme from a complex sample such as mitochondria, tissue homogenate or cell lysate from cancer cells using an anti-Complex II monoclonal antibody (mAb). After this purification, the Complex II enzyme may be quantified by detecting the production of ubiquinol by the enzyme using a colorimetric assay based on the dye DCPIP (2,6-diclorophenolindophenol). The ubiquinol produced by the Complex II enzyme reduces the blue colored DCPIP to the colorless compound $DCPIPH_2$. The reduction of DCPIP is detected by measuring a decrease in its absorbance at 600 nm. Kits for determining Complex II activity are commercially available, for example, the Complex II Enzyme Activity Microplate Assay Kit (ab109908) from Abcam (Cambridge, MA).

The subject afflicted with a cancer that exhibits increased Complex II activity may demonstrate a clinical benefit as a result of administration of the composition comprising the Coenzyme Q10 compound. In some embodiments, the clinical benefit is selected from the group consisting of stable disease per RECIST 1.1 criteria, partial response per RECIST 1.1 criteria, and complete response per RECIST 1.1 criteria.

The composition comprising the Coenzyme Q10 compound may be administered, for example, at least one time per week, at least two times per week, or at least three times per week. In some embodiments, the composition comprising the Coenzyme Q10 compound is administered by injection or infusion. In some embodiments, the composition comprising the Coenzyme Q10 compound is administered intravenously. In a particular embodiment, the Coenzyme Q10 compound (e.g. Coenzyme Q10) is administered by continuous infusion. The continuous infusion may be administered, for example, for at least 48 hours, at least 72 hours, at least 96 hours, at least 120 hours, or at least 144 hours or more. In other embodiments, the composition comprising the Coenzyme Q10 compound is administered topically. In certain embodiments of the aforementioned methods, the subject is human. In some embodiments, the composition comprising the Coenzyme Q10 compound is administered to the subject with an additional anti-cancer agent, for example, a chemotherapeutic agent or an anti-angiogenic agent.

In certain aspects, the invention relates to methods for the treatment of a glioma (e.g. a glioblastoma) in a subject comprising administering to the subject a composition comprising a Coenzyme Q10 compound (e.g. Coenzyme Q10), thereby treating the glioma in the subject. In some embodiments, the subject afflicted with the glioma (e.g. a glioblastoma) has not failed treatment with an anti-cancer agent.

In certain embodiments, formulations of the present disclosure may be utilized for the treatment of gliomas (e.g. glioblastomas) wherein the subject has failed treatment with at least one prior cancer therapeutic regimen, e.g., anti-cancer agent, e.g. chemotherapeutic regimen. In a particular embodiment, the at least one prior cancer therapeutic regimen comprises administration of temozolomide (TMZ) to the subject. Accordingly, in some embodiments, the present invention provides a method of treating a glioma (e.g. glioblastoma) in a subject, wherein the subject has failed treatment for the glioma with temozolomide (TMZ), the method comprising administering to the subject a composition comprising a Coenzyme Q10 compound, thereby treating the glioma in the subject. The formulations of the invention may also be utilized for inhibiting glioma (e.g. glioblastoma) tumor cell growth in a subject wherein the subject has failed at least one prior cancer therapeutic regimen (e.g. a cancer therapeutic regimen comprising administration of TMZ to the subject). Accordingly, the invention further provides methods of inhibiting glioma (e.g. glioblastoma) tumor cell growth in a subject, wherein the subject has failed at least one prior cancer therapeutic regimen, comprising administering the formulations of the invention to the subject, such that glioma tumor cell growth is inhibited. In a preferred embodiment, inhibiting glioma (e.g. glioblastoma) tumor growth includes achieving at least stable disease of the primary lesion by RECIST 1.1 criteria. In certain embodiments, the subject is a human subject.

Such formulations may include the hydrophobic therapeutic agent, e.g., CoQ10, its metabolites, or CoQ10 related compounds, in a pharmaceutically acceptable carrier. In some embodiments, such a formulation may include from about 0.001% to about 20% (w/w) of CoQ10, more preferably between about 0.01% and about 15% and even more preferably between about 0.1% to about 10% (w/w) of CoQ10. In one embodiment a formulation includes about 4% (w/w) of CoQ10. In one embodiment a formulation includes about 8% (w/w) of CoQ10. In various embodiments, the formulation includes about 0.1%, 0.2%. 0.3%, 0.4%. 0.5%, 0.6%, 0.7%, 0.8%. 0.9%, 1%, 2%, 3%, 4%, 5%, 6%, 7%, 8%, 9%, 10%, 11%, 12%, 13%, 14%, 15%, 16%, 17%, 18%, 19% or 20% (w/w) of CoQ10, or any range bracketed by those values. In certain embodiments, the formulations can be prepared as a percent weight to volume rather than a percent weight to weight. Depending on the formulation, the concentration of CoQ10 may be the same, or about the same in the w/w and the w/v percent formulations. As also noted herein, compositions of the present disclosure may be in a liquid form, capable of introduction into a subject by any means or route of administration within the purview of those skilled in the art. For example, compositions may be administered by routes of administration including, but not limited to, intravenous, intratumoral, combinations thereof, and the like.

In certain embodiments of the invention, methods are provided for treating or preventing a glioma (e.g. glioblastoma) in a human (e.g. a human that has failed treatment for the glioma with TMZ) by intravenously administering a composition comprising CoQ10, a CoQ10 precursor, metabolite, or related CoQ10 compound to the human such that treatment or prevention occurs, wherein the human is administered a dose of the formulation such that, preferably, CoQ10 is administered in the range of about 0.5 mg/kg/dose to about 10,000 mg/kg/dose, about 5 mg/kg/dose to about 5,000 mg/kg/dose, about 10 mg/kg/dose to about 3,000 mg/kg/dose. In one embodiment, the formulation is administered such that, preferably, CoQ10 is administered in the range of about 10 mg/kg/dose to about 1,400 mg/kg/dose. In one embodiment, the formulation is administered such that, preferably, CoQ10 is administered in the range of about 10 mg/kg/dose to about 650 mg/kg/dose. In one embodiment, the formulation is administered such that, preferably, CoQ10 is administered in the range of about 10 mg/kg/dose to about 200 mg/kg/dose.

In various embodiments, the formulation is administered such that, preferably, CoQ10 is administered at a dose of about 2 mg/kg/dose, 5 mg/kg/dose, 10 mg/kg/dose, 15 mg/kg/dose, 20 mg/kg/dose, 25 mg/kg/dose, 30 mg/kg/dose, 35 mg/kg/dose, 40 mg/kg/dose, 45 mg/kg/dose, 50 mg/kg/dose, 55 mg/kg/dose, 56 mg/kg/dose, 57 mg/kg/dose, 58 mg/kg/dose, 59 mg/kg/dose, 60 mg/kg/dose, 65 mg/kg/dose, 70 mg/kg/dose, 75 mg/kg/dose, 76 mg/kg/dose, 77 mg/kg/dose, 78 mg/kg/dose, 79 mg/kg/dose, 80 mg/kg/dose, 85 mg/kg/dose, 90 mg/kg/dose, 95 mg/kg/dose, 100 mg/kg/dose, 101 mg/kg/dose, 102 mg/kg/dose, 103 mg/kg/dose, 104 mg/kg/dose, 105 mg/kg/dose, 106 mg/kg/dose, 107 mg/kg/dose, 108 mg/kg/dose, 109 mg/kg/dose, 110 mg/kg/dose, 120 mg/kg/dose, 130 mg/kg/dose, 140 mg/kg/dose, 150 mg/kg/dose, 160 mg/kg/dose, 170 mg/kg/dose, 180 mg/kg/dose, 190 mg/kg/dose, 200 mg/kg/dose, 210 mg/kg/dose, 220 mg/kg/dose, 250 mg/kg/dose, 275 mg/kg/dose, 300 mg/kg/dose, 325 mg/kg/dose, 350 mg/kg/dose, 375 mg/kg/dose, 400 mg/kg/dose, 450 mg/kg/dose, 500 mg/kg/dose, 550 mg/kg/dose, 600 mg/kg/dose or 675 mg/kg/dose. In certain embodiments, the Coenzyme Q10 is administered at a dose selected from the group consisting of about 50 mg/kg/dose, about 66 mg/kg/dose, about 88 mg/kg/dose, about 110 mg/kg/dose, about mg/kg/dose, about 171 mg/kg/dose, about 215 mg/kg/dose, about 286 mg/kg/dose, about 380 mg/kg/dose, about 505 mg/kg/dose, and about 672 mg/kg/dose. In various embodiments, the dose is administered by continuous infusion over at least 48 hours, at least 72 hours or at least 96 hours. In various embodiments, the dose is administered by continuous infusion over about 48 hours, about 72 hours or about 96 hours.

In various embodiments, the formulation is administered such that, preferably, CoQ10 is administered at a dose of at least 2 mg/kg/dose, 5 mg/kg/dose, 10 mg/kg/dose, 15 mg/kg/dose, 20 mg/kg/dose, 25 mg/kg/dose, 30 mg/kg/dose, 35 mg/kg/dose, 40 mg/kg/dose, 45 mg/kg/dose, 50 mg/kg/dose, 55 mg/kg/dose, 56 mg/kg/dose, 57 mg/kg/dose, 58 mg/kg/dose, 59 mg/kg/dose, 60 mg/kg/dose, 65 mg/kg/dose, 70 mg/kg/dose, 75 mg/kg/dose, 76 mg/kg/dose, 77 mg/kg/dose, 78 mg/kg/dose, 79 mg/kg/dose, 80 mg/kg/dose, 85 mg/kg/dose, 90 mg/kg/dose, 95 mg/kg/dose, 100 mg/kg/dose, 101 mg/kg/dose, 102 mg/kg/dose, 103 mg/kg/dose, 104 mg/kg/dose, 105 mg/kg/dose, 106 mg/kg/dose, 107 mg/kg/dose, 108 mg/kg/dose, 109 mg/kg/dose, 110 mg/kg/dose, 120 mg/kg/dose, 130 mg/kg/dose, 140 mg/kg/dose, 150 mg/kg/dose, 160 mg/kg/dose, 170 mg/kg/dose, 180 mg/kg/dose, 190 mg/kg/dose, or 200 mg/kg/dose, 210 mg/kg/dose, 220 mg/kg/dose, 250 mg/kg/dose, 275 mg/kg/dose, 300 mg/kg/dose, 325 mg/kg/dose, 350 mg/kg/dose, 375 mg/kg/dose, 400 mg/kg/dose, 450 mg/kg/dose, 500 mg/kg/dose, 550 mg/kg/dose, 600 mg/kg/dose or 675 mg/kg/dose, wherein the dose does not result in any limiting toxicities. It should be understood that ranges having any one of these values as the upper or lower limits are also intended to be part of this invention, e.g., about 50 mg/kg/dose to about 200 mg/kg/dose, or about 650 mg/kg/dose to about 1400 mg/kg/dose, or about 55 mg/kg/dose to about 110 mg/kg/dose. In various embodiments, the dose is administered by continuous infusion over at least 48 hours, at least 72 hours or at least 96 hours. In various embodiments, the dose is administered by continuous infusion over about 48 hours, about 72 hours or about 96 hours.

In one embodiment the administered dose is at least about 1 mg/kg/dose, at least about 5 mg/kg/dose, at least about 10 mg/kg/dose, at least about 12.5 mg/kg/dose, at least about 20 mg/kg/dose, at least about 25 mg/kg/dose, at least about 30 mg/kg/dose, at least about 35 mg/kg/dose, at least about 40 mg/kg/dose, at least about 45 mg/kg/dose, at least about 50 mg/kg/dose, at least about 55 mg/kg/dose, at least about 60 mg/kg/dose, at least about 75 mg/kg/dose, at least about 100 mg/kg/dose, at least about 125 mg/kg/dose, at least about 150 mg/kg/dose, at least about 175 mg/kg/dose, at least about 200 mg/kg/dose, at least about 250 mg/kg/dose, at least about 300 mg/kg/dose, at least about 350 mg/kg/dose, at least about 400 mg/kg/dose, at least about 450 mg/kg/dose, at least about 500 mg/kg/dose, at least about 550 mg/kg/dose, at least about 600 mg/kg/dose, or at least about 600 mg/kg/dose. In certain embodiments, the Coenzyme Q10 is administered at a dose selected from the group consisting of at least 50 mg/kg/dose, at least 66 mg/kg/dose, at least 88 mg/kg/dose, at least 110 mg/kg/dose, at least 137 mg/kg/dose, at least 171 mg/kg/dose, at least 215 mg/kg/dose, at least 286 mg/kg/dose, at least 380 mg/kg/dose, at least 505 mg/kg/dose, or at least 672 mg/kg/dose. In various embodiments, the dose is administered by continuous infusion over at least 48 hours, at least 72 hours or at least 96 hours. In various embodiments, the dose is administered by continuous infusion over about 48 hours, about 72 hours or about 96 hours.

In certain embodiments, the administered dose is no more than about 20 mg/kg/dose, about 25 mg/kg/dose, about 30 mg/kg/dose, about 35 mg/kg/dose, about 40 mg/kg/dose, about 45 mg/kg/dose, about 50 mg/kg/dose, about 55 mg/kg/dose, about 60 mg/kg/dose, about 75 mg/kg/dose, about 100 mg/kg/dose, about 125 mg/kg/dose, about 150 mg/kg/dose, about 175 mg/kg/dose, about 200 mg/kg/dose, about 300 mg/kg/dose, about 400 mg/kg/dose, about 500 mg/kg/dose, about 600 mg/kg/dose, about 700 mg/kg/dose, about 800 mg/kg/dose, about 900 mg/kg/dose, about 1000 mg/kg/dose, about 1100 mg/kg/dose, about 1200 mg/kg/dose, or about 1300 mg/kg/dose. In various embodiments, the dose is administered by continuous infusion over at least 48 hours, at least 72 hours or at least 96 hours. In various embodiments, the dose is administered by continuous infusion over about 48 hours, about 72 hours or about 96 hours.

In all of the foregoing aspects, it is understood that any of the lower limit values and upper limit values can be combined to create a range. In certain embodiments, the administered dose is at least 75 mg/kg/dose or 100 mg/kg/dose or the rat equivalent to about, at least, 12.2 or 16.2 mg/kg/day in humans, or at least 85 mg/kg over a week period, or at least 113 mg/kg over a week period.

In certain embodiments, the Coenzyme Q10 is administered at a dose selected from the group consisting of about 11.8 mg/kg/day (24 hours), about 12.5 mg/kg/day (24 hours), about 14.4 mg/kg/day (24 hours), about 15.6 mg/kg (24 hours), about 16.5 mg/kg/day (24 hours), about 19 mg/kg/day (24 hours), about 20.4 mg/kg/day (24 hours), about 22 mg/kg/day (24 hours), about 25 mg/kg/day (24 hours), about 27.5 mg/kg/day (24 hours), about 29.3 mg/kg/day (24 hours), about 33 mg/kg/day (24 hours), about 34.2 mg/kg/day (24 hours), about 36.7 mg/kg/day (24 hours), about 41.7 mg/kg/day (24 hours), 42.8 mg/kg/day (24 hours), about 44 mg/kg/day (24 hours), about 45.7 mg/kg/day (24 hours), about 51.9 mg/kg/day (24 hours), about 53.8 mg/kg/day (24 hours), about 55 mg/kg/day (24 hours), about 57 mg/kg/day (24 hours), about 58.7 mg/kg/day (24 hours), about 64.8 mg/kg/day (24 hours), about 66.7 mg/kg/day (24 hours), about 68.5 mg/kg/day (24 hours), about 71.7 mg/kg/day (24 hours), about 73.4 mg/kg/day (24 hours), about 81.5 mg/kg/day (24 hours), about 85.5 mg/kg/day (24 hours), about 91.7 mg/kg/day (24 hours), about 107.5 mg/kg/day (24 hours), about 114.6 mg/kg/day (24 hours), and about 143.3 mg/kg/day (24 hours).

In certain embodiments, the Coenzyme Q10 is administered at a dose selected from the group consisting of at least 15.5 mg/kg/day (24 hours), at least 16.7 mg/kg/day (24 hours), at least 19.0 mg/kg/day (24 hours), at least 20.5 mg/kg/day (24 hours), at least 22.0 mg/kg/day (24 hours), at least 25.0 mg/kg/day (24 hours), at least 27.3 mg/kg/day (24 hours), at least 29.3 mg/kg/day (24 hours), at least 33.4 mg/kg/day (24 hours), at least 36.7 mg/kg/day (24 hours), at least 34.1 mg/kg/day (24 hours), at least 41.7 mg/kg/day (24 hours), at least 42.5 mg/kg/day (24 hours), at least 45.7 mg/kg/day (24 hours), at least 52.0 mg/kg/day (24 hours), at least 53.1 mg/kg/day (24 hours), at least 57 mg/kg/day (24 hours), at least 64.9 mg/kg/day (24 hours), at least 66.7 mg/kg/day (24 hours), at least 71.7 mg/kg/day (24 hours), at least 81.5 mg/kg/day (24 hours), at about 88.8 mg/kg/day (24 hours), at least 95.3 mg/kg/day (24 hours), at least 108.5 mg/kg/day (24 hours), at least 117.9 mg/kg/day (24 hours), at least 126.7 mg/kg/day (24 hours), at least 144.2 mg/kg/day (24 hours), at least 156.7 mg/kg/day (24 hours), at least 168.3 mg/kg/day (24 hours), at least 191.6 mg/kg/day (24 hours), at least 208.5 mg/kg/day (24 hours), at least 224 mg/kg/day (24 hours), and at least 254.9 mg/kg/day (24 hours).

In certain embodiments, the Coenzyme Q10 is administered at a dose selected from the group consisting of about 15.5 mg/kg/day (24 hours), about 16.7 mg/kg/day (24 hours), about 19.0 mg/kg/day (24 hours), about 20.5 mg/kg/day (24 hours), about 22.0 mg/kg/day (24 hours), about 25.0 mg/kg/day (24 hours), about 27.3 mg/kg/day (24 hours), about 29.3 mg/kg/day (24 hours), about 33.4 mg/kg/day (24 hours), about 36.7 mg/kg/day (24 hours), about 34.1 mg/kg/day (24 hours), about 41.7 mg/kg/day (24 hours), about 42.5 mg/kg/day (24 hours), about 45.7 mg/kg/day (24 hours), about 52.0 mg/kg/day (24 hours), about 53.1 mg/kg/day (24 hours), about 57 mg/kg/day (24 hours), about 64.9 mg/kg/day (24 hours), about 66.7 mg/kg/day (24 hours), about 71.7 mg/kg/day (24 hours), about 81.5 mg/kg/day (24 hours), about 88.8 mg/kg/day (24 hours), about 95.3 mg/kg/day (24 hours), about 108.5 mg/kg/day (24 hours), about 117.9 mg/kg/day (24 hours), about 126.7 mg/kg/day (24 hours), about 144.2 mg/kg/day (24 hours), about 156.7 mg/kg/day (24 hours), about 168.3 mg/kg/day (24 hours), about 191.6 mg/kg/day (24 hours), about 208.5 mg/kg/day (24 hours), about 224 mg/kg/day (24 hours), and about 254.9 mg/kg/day (24 hours).

In certain embodiments, the Coenzyme Q10 is administered at a dose selected from the group consisting of about 38 mg/kg/week, about 50 mg/kg/week, about 66 mg/kg/week, about 76 mg/kg/week, about 88 mg/kg/week, about 100 mg/kg/week, about 110 mg/kg/week, about 132 mg/kg/week, about 137 mg/kg/week, about 171 mg/kg/week, about 176 mg/kg/week, about 215 mg/kg/week, about 220 mg/kg/week, about 274 mg/kg/week, about 342 mg/kg week, and about 430 mg/kg/week. In certain embodiments, the Coenzyme Q10 is administered at a dose selected from the group consisting of about 100 mg/kg/week, about 132 mg/kg/week, about 171 mg/kg/week, about 215 mg/kg/week, about 274 mg/kg/week, about 430 mg/kg/week, about 572 mg/kg/week, about 760 mg/kg/week, about 1010 mg/kg/week, and about 1344 mg/kg/week.

In certain embodiments, the Coenzyme Q10 is administered at a dose selected from the group consisting of at least 100 mg/kg/week, at least 132 mg/kg/week, at least 171 mg/kg/week, at least 215 mg/kg/week, at least 274 mg/kg/week, at least 430 mg/kg/week, at least 572 mg/kg/week, at least 760 mg/kg/week, at least 1010 mg/kg/week, and at least 1344 mg/kg/week.

In various embodiments, the weekly dose is administered by two consecutive continuous infusions over about 72 hours each.

In one embodiment, the formulation, preferably, the CoQ10 formulation, is administered one time per week. In one embodiment, the formulation, preferably, the CoQ10 formulation, is administered two times per week. In one embodiment, the formulation, preferably, the CoQ10 formulation, is administered 3 times per week. In one embodiment, the formulation, preferably, the CoQ10 formulation, is administered four times per week. In another embodiment, the formulation, preferably, the CoQ10 formulation, is administered 5 times per week. In one embodiment, the formulation, preferably, the CoQ10 formulation, is administered once per day. In some embodiments, where the formulation is an IV formulation administered by infusion, the dosage is administered by infusion over about 1 hour, over about 2 hours, over about 3 hours, over about 4 hours, or longer. In one embodiment, the IV formulation is administered by infusion over about 4 hours, e.g., about 3.5 hours to about 4.5 hours. In certain embodiments, the formulation is administered over 4 or more hours. In certain embodiments, the formulation is administered over 8 or more hours. In certain embodiments, the formulation is administered over 12 hours or more. In certain embodiments, the formulation is administered over 18 or more hours. In certain embodiments, the formulation is administered over 24 or more hours. In certain embodiments, the formulation is administered over about 24 hours.

In certain embodiments, the formulation, preferably, a CoQ10 formulation, can be administered in one or more cycles. For example, the CoQ10 can be administered for 2, 3, 4, 5, 6, 7, 8, or more weeks consecutively, and then not administered for a period of 1, 2, 3, 4, or more weeks, providing a cycle of administration. In certain embodiments, the cycles are administered without a pause between cycles. In certain embodiments, at the end of one or more cycles, the patient is assessed to determine treatment efficacy, toxicity, and assess if the treatment should be continued, modified, or ended. The number of cycles of administration depends, for example, on the response of the subject, the severity of disease, other therapeutic interventions used on the subject, or any adverse response of the subject. In certain embodiments, the CoQ10 formulation is administered as long as the subject is exhibiting at least a stable response to treatment with no serious adverse events, e.g., dose limiting toxicities, grade IV toxicities, or persistent grade III toxicities that cannot be mitigated by the use of other interventions.

In another embodiment, the formulation, preferably, a CoQ10 formulation, is administered in the form of a CoQ10

IV formulation at a dosage of between about 10 mg/kg/dose and about 10,000 mg/kg/dose of CoQ10, about 20 mg/kg/dose to about 5000 mg/kg/dose, about 50 mg/kg/dose to about 3000 mg/kg/dose, about 100 mg/kg/dose to about 2000 mg/kg/dose, about 200 mg/kg/dose to about 1000 mg/kg/dose, about 300 mg/kg/dose to about 500 mg/kg/dose, or about 55 mg/kg/dose to about 110 mg/kg/dose wherein the CoQ10 formulation comprises between about 1% and 10% of CoQ10 (w/v). In one embodiment, the CoQ10 formulation comprises about 4% of CoQ10 (w/v). In one embodiment, the CoQ10 IV formulation comprises about 8% of CoQ10 (w/v). In other embodiments, the CoQ10 IV formulation comprises about 0.1%, 0.2%. 0.3%, 0.4%. 0.5%, 0.6%, 0.7%, 0.8%. 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of CoQ10 (w/v). It should be understood that ranges having any one of these values as the upper or lower limits are also intended to be part of this invention.

In the treatment of certain cancers according to the methods of the invention, e.g., treatment of a glioma (e.g. glioblastoma), the formulations may be in a pharmaceutically acceptable carrier that may be administered in a therapeutically effective amount to a subject as either a mono-therapy, in combination with at least one other anti-cancer agent, e.g., chemotherapeutic agent, for a given indication, in combination with radiotherapy, following surgical intervention to radically remove a tumor, in combination with other alternative and/or complementary acceptable treatments for cancer, and the like.

In certain embodiments, the effect a CoQ10 compound may have on certain cancers, e.g., glioma (e.g. glioblastoma) cells, according to the methods of the invention may depend, in part, on the various states of metabolic and oxidative flux exhibited by the glioma cells. A CoQ10 compound of the invention may be utilized to interrupt and/or interfere with the conversion of an oncogenic cell's dependency of glycolysis and increased lactate utility. As it relates to a cancer state, this interference with the glycolytic and oxidative flux of the tumor microenvironment may influence apoptosis and angiogenesis in a manner which reduces the viability or proliferative capacity of a cancer cell. In some embodiments, the interaction of a CoQ10 compound with glycolytic and oxidative flux factors may enhance the ability of the CoQ10 compound to exert its restorative apoptotic effect in the particular cancer, e.g., glioma (e.g. glioblastoma).

While the present disclosure has focused on CoQ10 and its metabolites, other compounds related to CoQ10 which may be administered instead of, or in combination with, CoQ10 include, but are not limited to, benzoquinones, isoprenoids, farnesols, farnesyl acetate, farnesyl pyrophosphate, 1-phenylalanine, d-phenylalanine, dl-phenylalanine, 1-tyrosine, d-tyrosine, dl-tyrosine, 4-hydroxy-phenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C8 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like. It is understood that such treatment methods can similarly be performed by administration of other CoQ10 precursors, metabolites, and related compounds.

In certain embodiments of the invention, the methods further include a treatment regimen which includes any one of or a combination of surgery, radiation, chemotherapy, e.g., hormone therapy, antibody therapy, therapy with growth factors, cytokines, and anti-angiogenic therapy.

(i) Treatment of Glioma after Failure of a Cancer Therapeutic Regimen

In one embodiment, administration of a CoQ10 compound as described herein, reduces glioma (e.g. glioblastoma) tumor size, inhibits glioma tumor growth and/or prolongs the survival time of a glioma tumor-bearing subject who has failed at least one prior cancer therapeutic regimen as compared to an appropriate control. Accordingly, this invention also relates to a method of treating glioma (e.g. glioblastoma) tumors in a human or other animal who has failed at least one prior cancer therapeutic regimen by administering to such human or animal an effective, non-toxic amount of a CoQ10 compound, for example, by administering an effective dose by IV administration, or, for example, by administering an effective dose by topical administration. One skilled in the art would be able, by routine experimentation with the guidance provided herein, to determine what an effective, non-toxic amount of a CoQ10 compound would be for the purpose of treating a glioma in a subject who has failed at least one prior cancer therapeutic regimen. For example, a therapeutically active amount of the CoQ10 compound may vary according to factors such as the disease stage (e.g., stage I versus stage IV), age, sex, medical complications (e.g., immunosuppressed conditions or diseases) and weight of the subject, and the ability of the CoQ10 compound to elicit a desired response in the subject. The dosage regimen may be adjusted to provide the optimum therapeutic response. For example, several divided doses may be administered daily, the dose may be administered by continuous infusion, or the dose may be proportionally reduced as indicated by the exigencies of the therapeutic situation.

In certain embodiments of the invention, the methods further include a treatment regimen which includes any one of or a combination of surgery, radiation, chemotherapy, e.g., hormone therapy, antibody therapy, therapy with growth factors, cytokines, and anti-angiogenic therapy.

It is understood that such treatment methods can similarly be performed by administration of CoQ10 precursors, metabolites, and related compounds.

Gliomas for treatment using the methods of the invention include, but are not limited to, ependymomas, astrocytomas (e.g. glioblastoma), oligodendrogliomas, brainstem gliomas, optic nerve gliomas, and mixed gliomas (e.g. oligoastrocytomas) which contain cells from different types of glia. In a particular embodiment, the glioma is a glioblastoma. In some embodiments, the glioma is a low-grade glioma. In other embodiments, the glioma is a high-grade glioma.

The compositions and methods provided herein are for the treatment of glioma (e.g. glioblastoma) in a subject wherein the subject has previously failed at least one prior (e.g., 1, 2, 3, 4, 5, 6, 7, 8, 9, 10, or more) cancer therapeutic, e.g., chemotherapeutic, regimen for the glioma. In a particular embodiment, the chemotherapeutic regimen comprises administering TMZ to the subject. In certain embodiments, the subject has failed treatment for the glioma with at least one additional cancer therapeutic agent, e.g. bevacizumab (Avastin). A subject who has failed a cancer therapeutic regimen does not achieve at least stable disease or loses stable disease as defined by RECIST 1.1 criteria after a short period in at least one target lesion during or after the treatment with the chemotherapeutic regimen. In certain embodiments, a short period is less than 6 months. In certain embodiments, a short period is less than 5 months. In certain embodiments, a short period is less than 4 months. In certain embodiments, a short period is less than 3 months. In certain embodiments, a short period is less than 2 months. In certain embodiments, a short period is less than 1 month. In certain embodiments, a short period is less than 2 weeks. A subject who has failed a cancer therapeutic regimen includes a subject who has progressive disease during treatment or shortly after the end of treatment with a cancer therapeutic regimen. In a preferred embodiment, the subject who has failed a cancer therapeutic regimen still has, or is suspected of having, the primary tumor. It is understood that it may not be possible or desirable to specifically identify the primary tumor, particularly when a subject presents with metastatic disease. In a preferred embodiment, the subject who has failed a cancer therapeutic regimen still has a tumor at the site of the primary tumor, i.e., in the organ in which the primary tumor arose. In certain embodiments, the primary tumor is a solid tumor.

A subject who has failed a cancer therapeutic regimen has not been cured of the glioma (e.g. glioblastoma) being treated or according to a clinical definition, e.g., achieving complete remission in target or non-target lesions per the RECIST 1.1 criteria for an extended period after the conclusion of treatment of the glioma, e.g., for at least one year, at least 5 years, at least 10 years. For example, a subject treated for a glioma (e.g. glioblastoma) who is cured, i.e., who has achieved complete remission, has a greater chance of suffering from a distinct cancer later in life. A subject successfully treated for a glioma (i.e., a subject who achieves clinical remission for a sufficient time to be considered cured, e.g., at least 5 years of clinical remission) who later develops a second cancer is not considered to have failed the first cancer therapeutic regimen.

A subject who has failed a cancer therapeutic regimen may have also undergone other treatments for the glioma (e.g. glioblastoma) in conjunction with an anticancer agent including surgery for tumor resection and/or radiation therapy. The subject may have undergone bone marrow transplant or other procedures. It is understood that failure of a cancer therapeutic regimen may be due, at least in part, to a failure of one or more interventions other than the anticancer agent.

Failure of a cancer therapeutic regimen can result from the subject suffering from a dose limiting toxicity, e.g., a grade IV toxicity or a lower grade toxicity that cannot be tolerated by the subject or resolved with other interventions, e.g., anti-nausea agents, stimulators of red blood cell production, agents to normalize clotting, agents to reduce immune/allergic response, etc., depending on the specific toxicity. It is understood that such dose limiting toxicities can result in a shortened or incomplete cancer therapeutic regimen being administered to the subject, resulting in reduced efficacy of the agent.

VI. Combination Therapies

In certain embodiments, the formulations of the invention, e.g., the CoQ10 formulations, can be used in combination therapy with at least one additional anticancer agent, e.g., chemotherapeutic agent. In preferred embodiments, CoQ10 is administered in an amount that would be therapeutically effective if delivered alone, i.e., CoQ10 is administered and/or acts as a therapeutic agent, and not predominantly as an agent to ameliorate side effects of other chemotherapy or other cancer treatments. CoQ10 and/or pharmaceutical formulations thereof and the additional therapeutic (anticancer) agent can act additively or, more preferably, synergistically. In one embodiment, CoQ10 and/or a pharmaceutical formulation thereof is administered concurrently with the administration of an additional anticancer (e.g., chemotherapeutic) agent. In another embodiment, a CoQ10 compound and/or pharmaceutical formulation thereof is administered prior or subsequent to administration of another therapeutic (anticancer) agent wherein both agents are present in the subject at the same time or have therapeutic activity in the subject at the same time. In one embodiment, the CoQ10 and additional anticancer (e.g., chemotherapeutic) agent act synergistically. In one embodiment, the CoQ10 and additional anticancer (e.g., chemotherapeutic) agent act additively.

Where the therapeutic methods of the invention further comprise administration of one or more additional therapeutic agents, e.g., one or more anticancer agents, the anticancer agents may include, e.g., chemotherapeutic agents, (e.g., small molecule anticancer agents), or biologic anticancer agents including both protein based and nucleic acid based therapeutics. In one embodiment, an additional anticancer agent for use in the therapeutic methods of the invention is a chemotherapeutic agent, e.g., TMZ. In one embodiment, an additional anticancer agent for use in the therapeutic methods of the invention is an antibody, e.g., bevacizumab.

Small molecule chemotherapeutic agents generally belong to various classes including, for example: (1) Topoisomerase II inhibitors (cytotoxic antibiotics), such as the anthracyclines/anthracenediones, e.g., doxorubicin, epirubicin, idarubicin and nemorubicin, the anthraquinones, e.g., mitoxantrone and losoxantrone, and the podophillotoxines, e.g., etoposide and teniposide; (2) Agents that affect microtubule formation (mitotic inhibitors), such as plant alkaloids (e.g., a compound belonging to a family of alkaline, nitrogen-containing molecules derived from plants that are biologically active and cytotoxic), e.g., taxanes, e.g., paclitaxel and docetaxel, and the vinka alkaloids, e.g., vinblastine, vincristine, and vinorelbine, and derivatives of podophyllotoxin; (3) Alkylating agents, such as nitrogen mustards, ethyleneimine compounds, alkyl sulphonates and other compounds with an alkylating action such as nitrosoureas, dacarbazine, cyclophosphamide, ifosfamide and melphalan; (4) Antimetabolites (nucleoside inhibitors), for example, folates, e.g., folic acid, fiuropyrimidines, purine or pyrimidine analogues such as 5-fluorouracil, capecitabine, gemcitabine, methotrexate, and edatrexate; (5) Topoisomerase I inhibitors, such as topotecan, irinotecan, and 9-nitrocamptothecin, camptothecin derivatives, and retinoic acid; and (6) Platinum compounds/complexes, such as cisplatin, oxaliplatin, and carboplatin.

Exemplary chemotherapeutic agents for use in the methods of the invention include, but are not limited to, amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-I1, IO-hydroxy-7-ethyl-camptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10, 11-methylenedioxycamptothecin, karenitecin, 9-nitrocamptothecin, TAS 103, vindesine, L-phenylalanine mustard, ifosphamidemefosfamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol), bleomycin, mTor, epidermal growth factor receptor (EGFR), and fibroblast growth factors (FGF) and combinations thereof which are readily apparent to one of skill in the art based on the appropriate standard of care for a particular tumor or cancer.

In another embodiment, an additional chemotherapeutic agent for use in the combination therapies of the invention is a biologic agent. Biologic agents (also called biologics) are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below and generally belong to various classes including, for example: (1) Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leuteinizing hormones; and (2) Enzymes, proteins, peptides, polyclonal and/or monoclonal antibodies, such as interleukins, interferons, colony stimulating factor, etc.

In one embodiment, the biologic is an interferon. Interferons (IFN) are a type biologic agent that naturally occurs in the body. Interferons are also produced in the laboratory and given to cancer patients in biological therapy. They have been shown to improve the way a cancer patient's immune system acts against cancer cells. Interferons may work directly on cancer cells to slow their growth, or they may cause cancer cells to change into cells with more normal behavior. Some interferons may also stimulate natural killer cells (NK) cells, T cells, and macrophages which are types of white blood cells in the bloodstream that help to fight cancer cells.

In one embodiment, the biologic is an interleukin. Interleukins (IL) stimulate the growth and activity of many immune cells. They are proteins (cytokines and chemokines) that occur naturally in the body, but can also be made in the laboratory. Some interleukins stimulate the growth and activity of immune cells, such as lymphocytes, which work to destroy cancer cells.

In another embodiment, the biologic is a colony-stimulating factor. Colony-stimulating factors (CSFs) are proteins given to patients to encourage stem cells within the bone marrow to produce more blood cells. The body constantly needs new white blood cells, red blood cells, and platelets, especially when cancer is present. CSFs are given, along with chemotherapy, to help boost the immune system. When cancer patients receive chemotherapy, the bone marrow's ability to produce new blood cells is suppressed, making patients more prone to developing infections. Parts of the immune system cannot function without blood cells, thus colony-stimulating factors encourage the bone marrow stem cells to produce white blood cells, platelets, and red blood cells.

With proper cell production, other cancer treatments can continue enabling patients to safely receive higher doses of chemotherapy.

In another embodiment, the biologic is an antibody. Antibodies, e.g., monoclonal antibodies, are agents, produced in the laboratory, that bind to cancer cells. Monoclonal antibody agents do not destroy healthy cells. Monoclonal antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation.

Examples of antibodies which may be used in the combination treatment of the invention include anti-CD20 antibodies, such as, but not limited to, cetuximab, Tositumomab, rituximab, and Ibritumomab. Anti-HER2 antibodies may also be used in combination with CoQ10 for the treatment of cancer. In one embodiment, the anti-HER2 antibody is Trastuzumab (Herceptin). Other examples of antibodies which may be used in combination with CoQ10 for the treatment of cancer include anti-CD52 antibodies (e.g., Alemtuzumab), anti-CD-22 antibodies (e.g., Epratuzumab), and anti-CD33 antibodies (e.g., Gemtuzumab ozogamicin). Anti-VEGF antibodies may also be used in combination with CoQ10 (e.g., for the treatment of glioma, such as glioblastoma). In one embodiment, the anti-VEGF antibody is bevacizumab. In other embodiments, the biologic agent is an antibody which is an anti-EGFR antibody e.g., cetuximab. Another example is the anti-glycoprotein 17-1A antibody edrecolomab. Numerous other anti-tumor antibodies are known in the art and would be understood by the skilled artisan to be encompassed by the present invention.

In another embodiment, the biologic is a cytokine. Cytokine therapy uses proteins (cytokines) to help a subject's immune system recognize and destroy those cells that are cancerous. Cytokines are produced naturally in the body by the immune system, but can also be produced in the laboratory. This therapy is used with advanced melanoma and with adjuvant therapy (therapy given after or in addition to the primary cancer treatment). Cytokine therapy reaches all parts of the body to kill cancer cells and prevent tumors from growing.

In another embodiment, the biologic is a fusion protein. For example, recombinant human Apo2L/TRAIL (GENETECH) may be used in a combination therapy. Apo2/TRAIL is the first dual pro-apoptotic receptor agonist designed to activate both pro-apoptotic receptors DR4 and DR5, which are involved in the regulation of apoptosis (programmed cell death).

In one embodiment, the biologic is a therapeutic nucleic acid molecule. Nucleic acid therapeutics are well known in the art. Nucleic acid therapeutics include both single stranded and double stranded (i.e., nucleic acid therapeutics having a complementary region of at least 15 nucleotides in length) nucleic acids that are complementary to a target sequence in a cell. Therapeutic nucleic acids can be directed against essentially any target nucleic acid sequence in a cell. In certain embodiments, the nucleic acid therapeutic is targeted against a nucleic acid sequence encoding a stimulator of angiogenesis, e.g., VEGF, FGF, or of tumor growth, e.g., EGFR.

Antisense nucleic acid therapeutic agents are single stranded nucleic acid therapeutics, typically about 16 to 30 nucleotides in length, and are complementary to a target nucleic acid sequence in the target cell, either in culture or in an organism.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. The antisense RNA molecule may have about 15-30 nucleotides that are complementary to the target mRNA. Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. The entire contents of each of the patents listed in this paragraph are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference.

Additional exemplary biologic agents for use in the methods of the invention include, but are not limited to, gefitinib (Iressa), anastrazole, diethylstilbesterol, estradiol, premarin, raloxifene, progesterone, norethynodrel, esthisterone, dimesthisterone, megestrol acetate, medroxyprogesterone acetate, hydroxyprogesterone caproate, norethisterone, methyltestosterone, testosterone, dexamthasone, prednisone, Cortisol, solumedrol, tamoxifen, fulvestrant, toremifene, aminoglutethimide, testolactone, droloxifene, anastrozole, bicalutamide, flutamide, nilutamide, goserelin, flutamide, leuprolide, triptorelin, aminoglutethimide, mitotane, goserelin, cetuximab, erlotinib, imatinib, Tositumomab, Alemtuzumab, Trastuzumab, Gemtuzumab, Rituximab, Ibritumomab tiuxetan, Bevacizumab, Denileukin diftitox, Daclizumab, interferon alpha, interferon beta, anti-4-1BB, anti-4-1BBL, anti-CD40, anti-CD 154, anti-OX40, anti-OX40L, anti-CD28, anti-CD80, anti-CD86, anti-CD70, anti-CD27, anti-HVEM, anti-LIGHT, anti-GITR, anti-GITRL, anti-CTLA-4, soluble OX40L, soluble 4-IBBL, soluble CD154, soluble GITRL, soluble LIGHT, soluble CD70, soluble CD80, soluble CD86, soluble CTLA4-Ig, GVAX®, and combinations thereof which are readily apparent to one of skill in the art based on the appropriate standard of care for a particular tumor or cancer. The soluble forms of agents may be made as, for example fusion proteins, by operatively linking the agent with, for example, Ig-Fc region.

It should be noted that more than one additional anticancer agent (e.g., chemotherapeutic agents), e.g., 2, 3, 4, 5, or more, may be administered in combination with the CoQ10 formulations provided herein. For example, in one embodiment two additional anticancer agents may be administered in combination with CoQ10. For example, in one embodiment, a chemotherapeutic small molecule agent, an anticancer biologic agent, and CoQ10 may be administered. Appropriate doses and routes of administration of the anticancer agents provided herein are known in the art.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Each patent, publication, and reference cited herein is incorporated herein by reference in their entirety. Further, WO 2008/116135 (PCT Appln. No. PCT/US2008/116135), WO2009/073843 (PCT Appln. No. PCT/US2008/085669), WO2010/132507 (PCT Appln. No. PCT/US2010/034453), WO2011/11290 (PCT Appln. No. PCT/US2011/028042), WO2012/174559 (PCT Appln. No. PCT/US2012/043001), US Patent Application Publication No.: US2011/0027247, US Patent Application Publication No.: US2015/0157559, are hereby incorporated by reference in their entirety.

EXAMPLES

Example 1: Assessment of Mitochondrial Function in MDA-MB231 and MIA PaCa-2 Cell Lines Treated with Coenzyme Q10

Figure 1B:
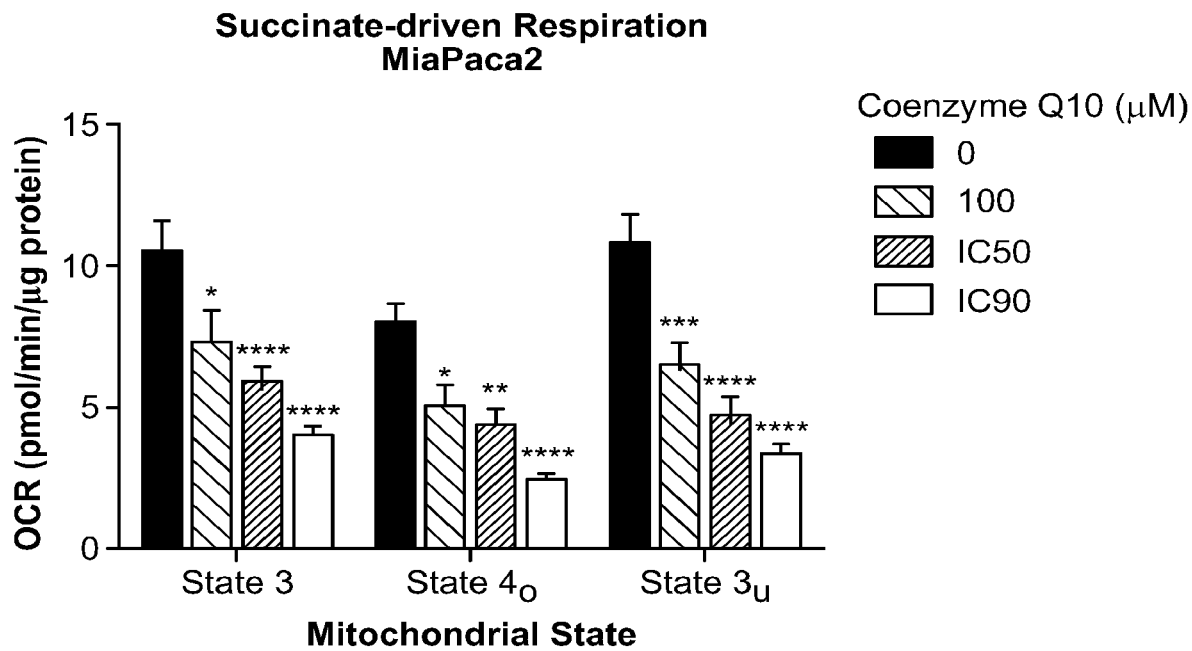

Oxygen consumption rate (OCR) was measured during various states of succinate-fueled mitochondrial respiration in the triple-negative breast cancer cell line MDA-MB231 and the mutant K-Ras-driven pancreatic cancer cell line MIA PaCa-2 treated with different concentrations of Coenzyme Q10. MDA-MB231 and MIA PaCa-2 have been previously found to be two of the most Coenzyme Q10 sensitive cell lines, with $IC_{50}$ values for Coenzyme Q10 of 155 and 137 µM, respectively, and $IC_{90}$ values of 310 and 274 µM, respectively. The assays were performed in permeabilized adherent cells using the Seahorse XF96 Analyzer. Cells were permeabilized with XF PMP reagent and put into mitochondrial State 3 by replacing the growth media with Mitochondrial Assay Solution (containing mannitol, sucrose, $KH_2PO_4$, $MgCl_2$, HEPES, and EGTA) supplemented with succinate, rotenone (to block reverse electron transfer back to Complex I), and ADP. OCR was measured in State 3, and then again upon sequential injection of oligomycin and FCCP to induce State 4o (o=oligomycin) and State 3u (u=uncoupled). MDA-MB231 cells were treated with 100 µM, 155 µM ($IC_{50}$) or 310 µM ($IC_{90}$) Coenzyme Q10. MIA PaCa-2 cells were treated with 100 µM, 137 µM ($IC_{50}$) or 274 µM ($IC_{90}$) Coenzyme Q10. As shown in FIG. 1, succinate-fueled respiration is significantly decreased by Coenzyme Q10 in a dose dependent manner.

Figure 2A:
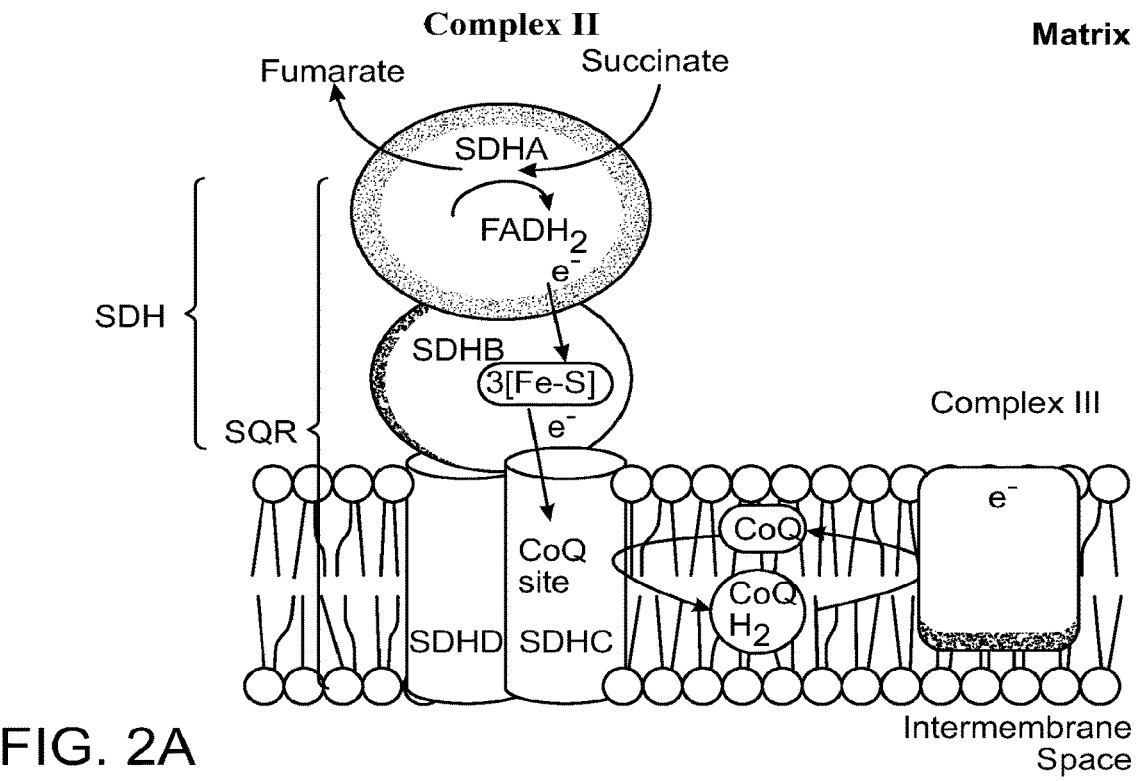
FIGS. 2A and 2B show mitochondrial respiratory chain Complex II in normal cells (2A) and during apoptosis (2B). Complex II disintegrates during apoptosis, which leads to the specific release of the succinate dehydrogenase (SDH) A/SDHB subcomplex into the matrix in response to a pH drop. This dissociation uncouples its two enzymatic activities (SDH and succinate coenzyme Q oxidoreductase (SQR) activities) for superoxide ($O_2^-$) production and subsequent apoptosis. From Grimm, 2013, Biochimica et Biophysica Acta 1827: 565-572, the entire contents of which are incorporated herein by reference.
Figure 2B:
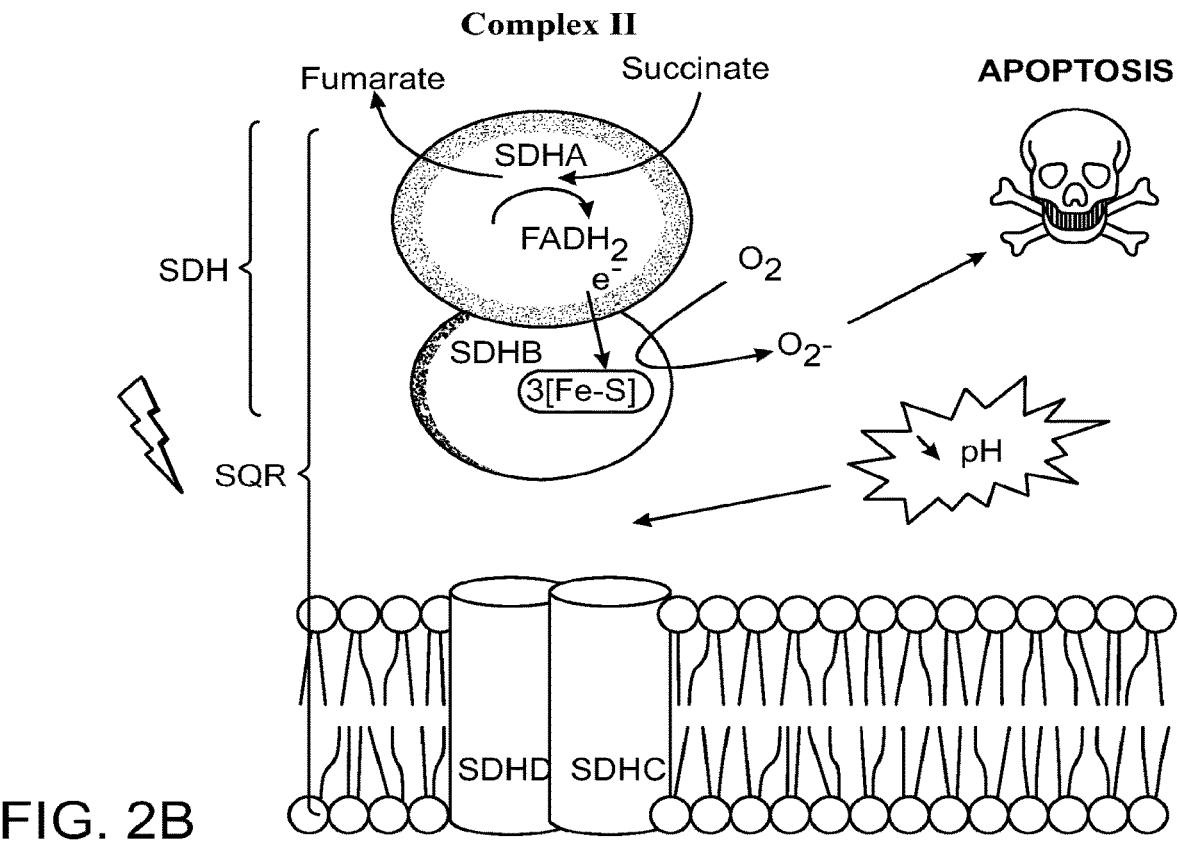

Example 2: Effects of Coenzyme Q10 on Mitochondrial Respiratory Chain Complex II in MDA-MB231 Breast Cancer Cells Succinate is a substrate for Complex II of the mitochondrial electron transport chain, the function of which is to catalyze the conversion of succinate to fumarate while in concert oxidizing FAD to FADH2. The electrons from FAD are then passed through Complexes II, III (by way of the Q pool), and IV, and finally to oxygen. Complex II has a well-defined role in activation and propagation of cell death signals. This is thought to result from enhanced reactive oxygen species production when electrons leak from Complex II during apoptosis. For example, Complex II disintegrates during apoptosis, which leads to the specific release of the succinate dehydrogenase (SDH) A/SDHB subcomplex into the matrix in response to a pH drop. This dissociation uncouples its two enzymatic activities (SDH and succinate coenzyme Q oxidoreductase (SQR) activities) for superoxide (02) production and subsequent apoptosis. See FIG. 2, mitochondrial respiratory chain Complex II in normal cells (top panel) and during apoptosis (bottom panel). Grimm, 2013, Biochimica et Biophysica Acta 1827: 565-572, the entire contents of which are incorporated herein by reference.

Figure 3:
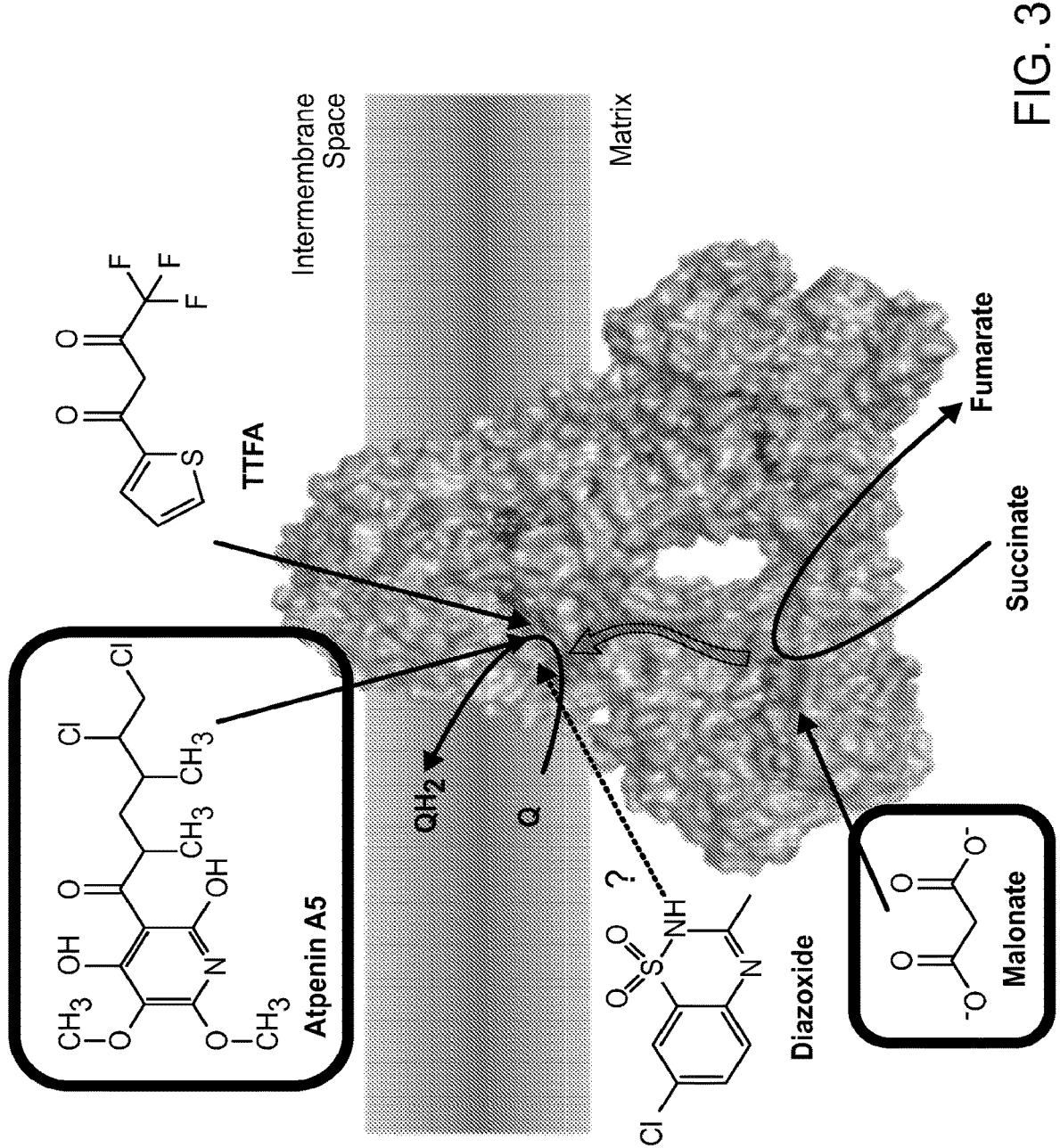
FIG. 3 shows two inhibitors of mitochondrial respiratory chain Complex II, atpenin A5 and malonate, which act at different sites on Complex II. Atpenin is a Complex II Qp site inhibitor which blocks the electron transfer from the terminal FeS-cluster onto ubiquinone and has been shown to increase ROS production. Malonate is a competitive inhibitor of the Complex II dicarboxylate site which prevents conversion of succinate to fumarate and oxidation of FAD to FADH2 and has been shown to decrease ROS.

To assess whether the effects of Coenzyme Q10 on Complex II-mediated respiration are functionally linked to Coenzyme Q10-induced cytotoxicity, MDA-MB231 cells were co-treated with two inhibitors of Complex II (atpenin A5 and malonate) which act at separate sites in Complex II. Atpenin A5 is a Complex II Qp site inhibitor which blocks the electron transfer from the terminal FeS-cluster onto ubiquinone and has been reported to increase ROS production. Malonate is a competitive inhibitor of the Complex II dicarboxylate site which prevents conversion of succinate to fumarate and oxidation of FAD to FADH2 and is reported to decrease ROS. See FIG. 3.

The viability of MDA-MB231 cells treated with atpenin A5 and Coenzyme Q10 or malonate and Coenzyme Q10 was determined by a CellTiter-Fluor viability assay (Promega, Cat. No. G6080). Briefly, cells were co-treated with 0, 25, 50, 100, 200, 400, 800 or 1600 µM Coenzyme Q10 and either 5 µM Atpenin A5 or 5 mM malonic acid for 72 h, and then assayed per the manufacture's protocol. The CellTiter-Fluor Cell Viability Assay measures a conserved and constitutive protease activity within live cells and therefore serves as a marker of cell viability. Results obtained using the CellTiter-Fluor Cell Viability Assay correlate well with other established methods of determining cell viability.

Figure 4A:
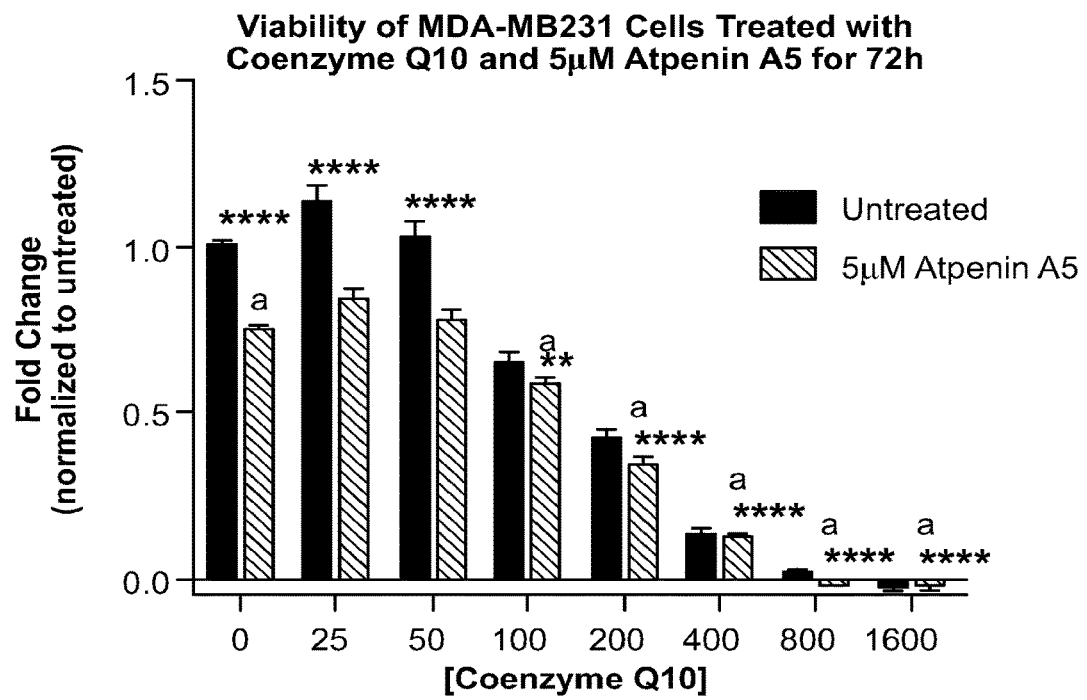
FIGS. 4A and 4B show the effect of the Complex II inhibitors atpenin A5 (4A) and malonate (4B) on Coenzyme Q10-induced cytotoxicity in the triple negative breast cancer cell line MDA-MB231. Atpenin A5 enhanced the cytotoxic effect of Coenzyme Q10 (4A), while malonate reduced the cytotoxic effect of Coenzyme Q10 (4B).
Figure 4B:
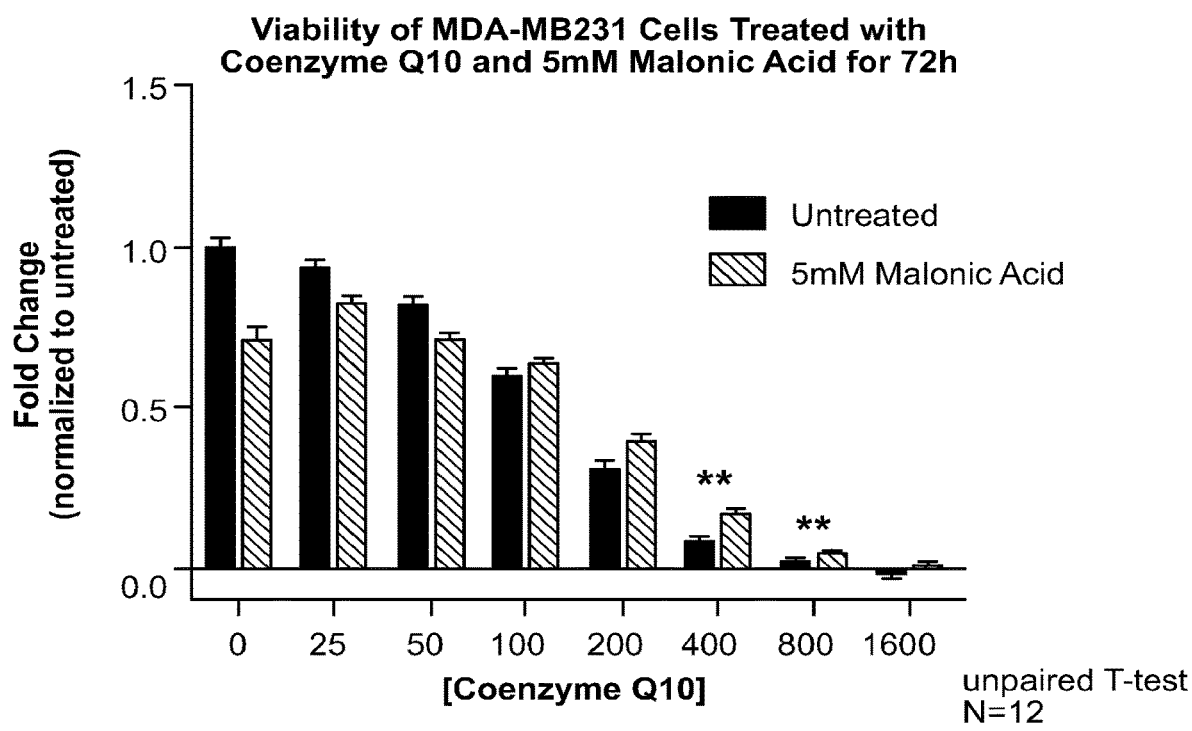

MDA-MB231 cells co-treated with Coenzyme Q10 and atpenin A5 exhibited enhanced cytotoxicity, whereas co-treatment with Coenzyme Q10 with malonate resulted in attenuation of Coenzyme Q10-induced cytotoxicity. See FIG. 4. These results suggest that electron flow through Complex II increases the efficacy of Coenzyme Q10 in initiating cell death, since promoting electron leakage out of Complex II (and likely ROS production), i.e. by treatment with atpenin A5, enhances cell death, whereas blocking election flow into Complex II (and likely decreasing ROS production), i.e. by treatment with malonate, attenuates cell death.

These results were confirmed using a second assay for cell death, propidium iodide (PI) and Annexin V flow cytometry, which assess apoptotic and necrotic cell death, respectively. MDA-MB231 cells were treated with Coenzyme Q10 and/or malonate as shown below:
1. Untreated
2. Malonate (5 mM)
3. Coenzyme Q10 $IC_{50}$ (155 µM)
4. Coenzyme Q10 $IC_{50}$ (155 µM)+Malonate (5 mM)
5. Coenzyme Q10 $IC_{90}$ (310 µM)
6. Coenzyme Q10 $IC_{90}$ (310 µM)+Malonate (5 mM)

At 72 hours post treatment, cell culture supernatant (containing detached apoptotic cells) and adherent cells were harvested by trypsinization, centrifuged at 500 g for 5 minutes, and the resulting pellets were washed in staining media (PBS, 0.5% FBS). Cells were co-stained with FITC conjugated anti-Annexin-V (1:100, Molecular Probes) to detect PS exposure on the outer membrane surface and Propidium Iodine (PI, 1:2500, Molecular Probes) in 200 µL binding buffer (Molecular Probes). After a 15 minute incubation in the dark, the percentage of Annexin V+/PI+ cells was analyzed using an Accuri C6 Flow Cytometer (BD Biosciences) and samples were run within one hour after staining.

The cells were rated as follows:
1. PI-negative and Annexin V-negative: viable
2. PI-negative and Annexin V-positive: early apoptosis
3. PI-positive and Annexin V-positive: late apoptosis
4. PI-positive and Annexin V-negative: dead.

Figure 5:
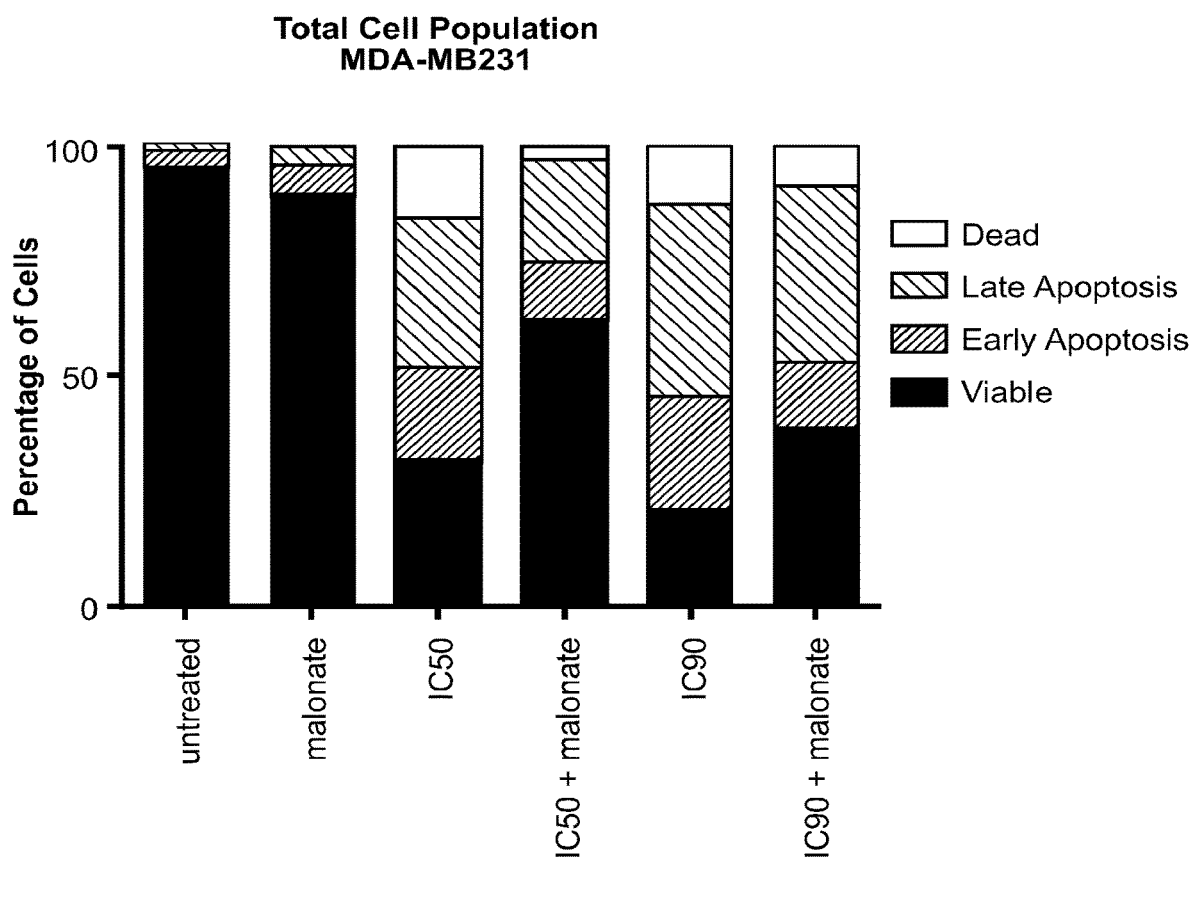
FIG. 5 shows the effect of the Complex II inhibitor malonate (5 mM) on Coenzyme Q10-induced cytotoxicity in the triple negative breast cancer cell line MDA-MB231. IC50=155 µM Coenzyme Q10; IC90=310 µM Coenzyme Q10. Cell status was determined by propidium iodide (PI) and Annexin V flow cytometry.
Figure 6:
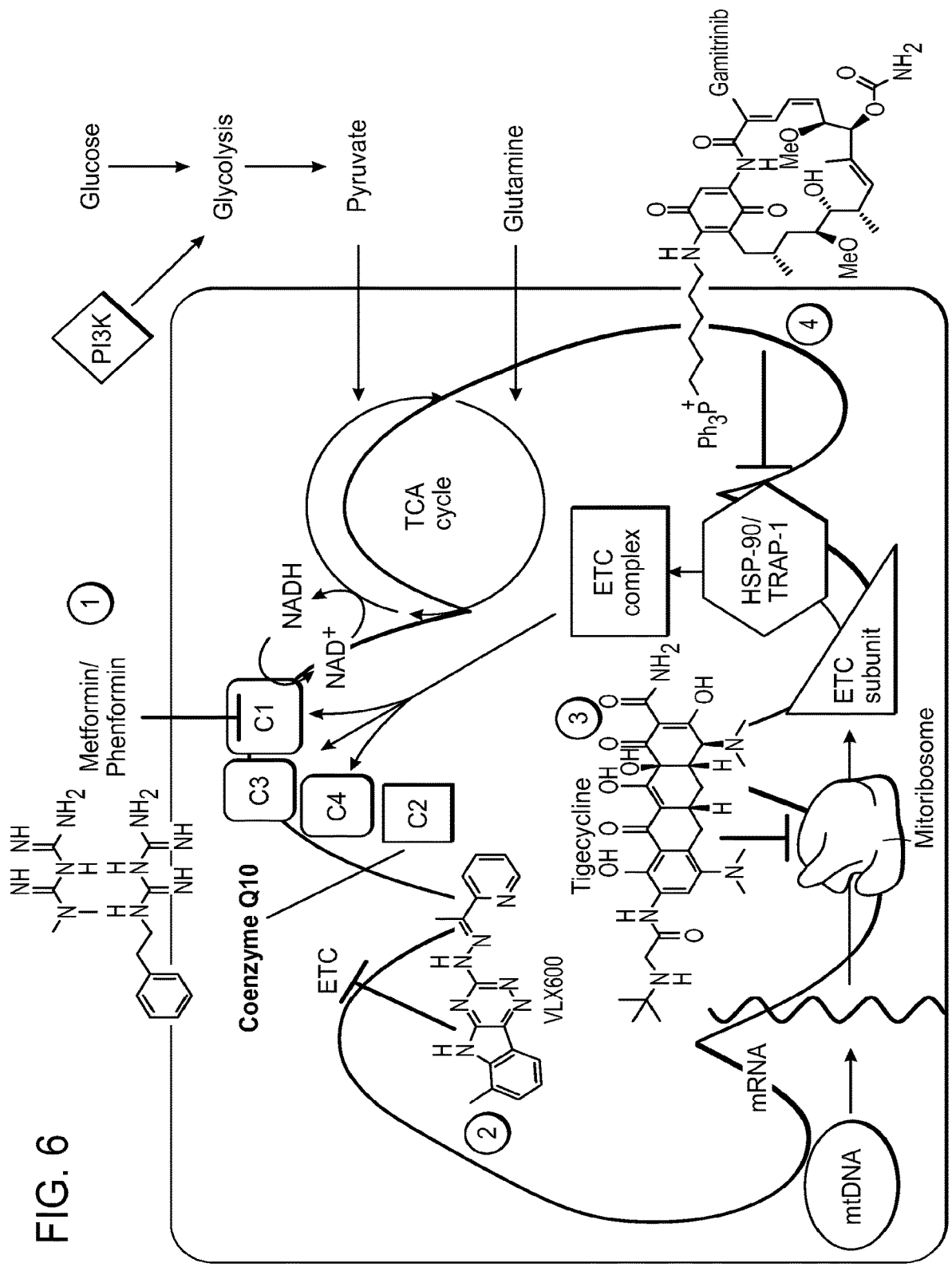
FIG. 6 shows a schematic illustrating drugs targeting the mitochondria. Coenzyme Q10 targets Complex II (C2). Adapted from Weinberg et al., 2015, Nature Chemical Biology 11: 9-15, the entire contents of which are incorporated herein by reference.

As shown in FIG. 5, malonate attenuated Coenzyme Q10-induced cell death in MDA-MB231 cells. Taken together, these data demonstrate that Complex II-mediated respiration is functionally linked to Coenzyme Q10-induced cytotoxicity.

Example 3: Effects of Coenzyme Q10 on Temozolomide-Resistant and Temozolomide-Sensitive Glioblastoma Cell Lines In Vitro Significant and consistent electron transport chain remodeling has been shown in temozolomide (TMZ)-resistant glioblastoma using in vitro models of TMZ chemo-resistance, paired tumor biopsies, and patient derived TMZ-sensitive and TMZ-resistant xenograft cell lines. See Oliva et al., 2010, J Biol. Chem. 285(51): 39759-39767, which is incorporated by reference herein in its entirety. For example, Oliva et al. demonstrated decreases in Complex I and V activity and increases in Complex II, III and IV activity in TMZ-resistant glioblastomas (GB). Based on these studies, it is clear that mitochondrial function in treatment naïve GB is quite different than that of TMZ refractory tumors. Moreover, TMZ refractory GB appears to be more reliant on Complex II-driven respiration. Taking into consideration the in vitro results described above obtained in other metabolically active cancer cell models demonstrating that increased electron flow through Complex II is associated with increased Coenzyme Q10-mediated cell death, TMZ-resistant glioblastoma is expected to be especially sensitive to Coenzyme Q10, and therefore CoQ10 will be highly effective in treating TMZ resistant glioblastoma.

Using the methods described above in Examples 1 and 2, further studies are conducted to characterize succinate-fueled respiration and its relationship to Coenzyme Q10 induced cell death in the TMZ-sensitive glioblastoma cell line U251 and the TMZ-resistant glioblastoma cell line UTMZ. This TMZ-resistant cell line was developed by subjecting mice with established flank tumors to successively higher doses of TMZ until tumor growth was no longer inhibited by 120 mg/kg/day TMZ for 5 days. See Oliva et al., cited above. Oxygen consumption rate (OCR) is measured during various states of succinate-fueled mitochondrial respiration in the TMZ-resistant and TMZ-sensitive cell glioblastoma cell lines treated with different concentrations of Coenzyme Q10 using the methods described above in Example 1. The sensitivity of the TMZ-resistant and TMZ-sensitive glioblastoma cell lines to Coenzyme Q10 is determined by measuring the $IC_{50}$ and $IC_{90}$ values for Coenzyme Q10 in these cell lines. To assess whether the effects of Coenzyme Q10 on Complex II-mediated respiration are functionally linked to Coenzyme Q10-induced cytotoxicity in glioblastoma, the TMZ-resistant and TMZ-sensitive glioblastoma cell lines are treated with atpenin A5 and malonate as described above in Example 2.

Example 4: Effects of Coenzyme Q10 Treatment in a Rat Model of Glioma

Figure 7:
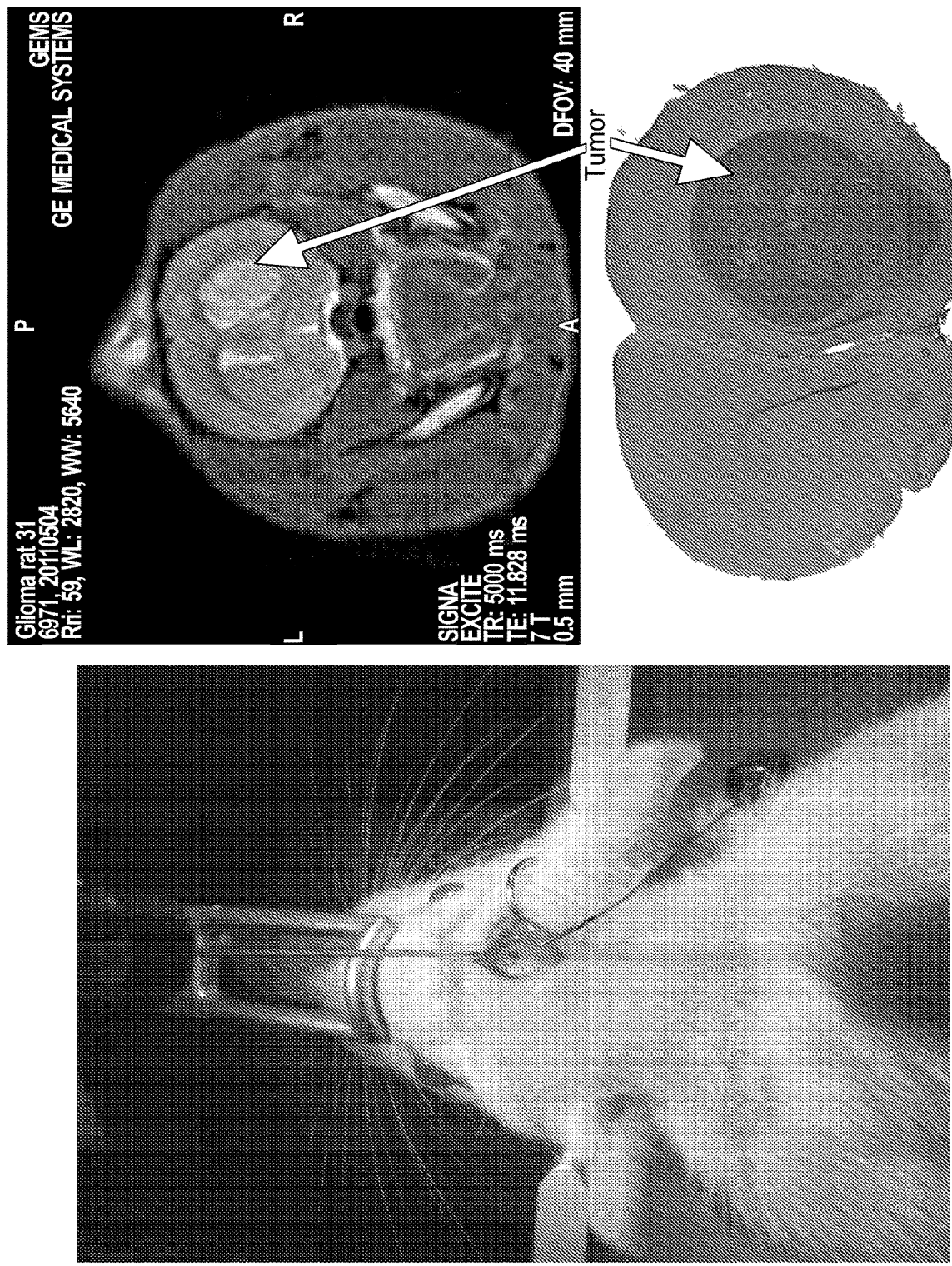
FIG. 7 shows an allograft of the C6 glioma cell line in rat which develops into a glioma-like tumor.
Figure 8:
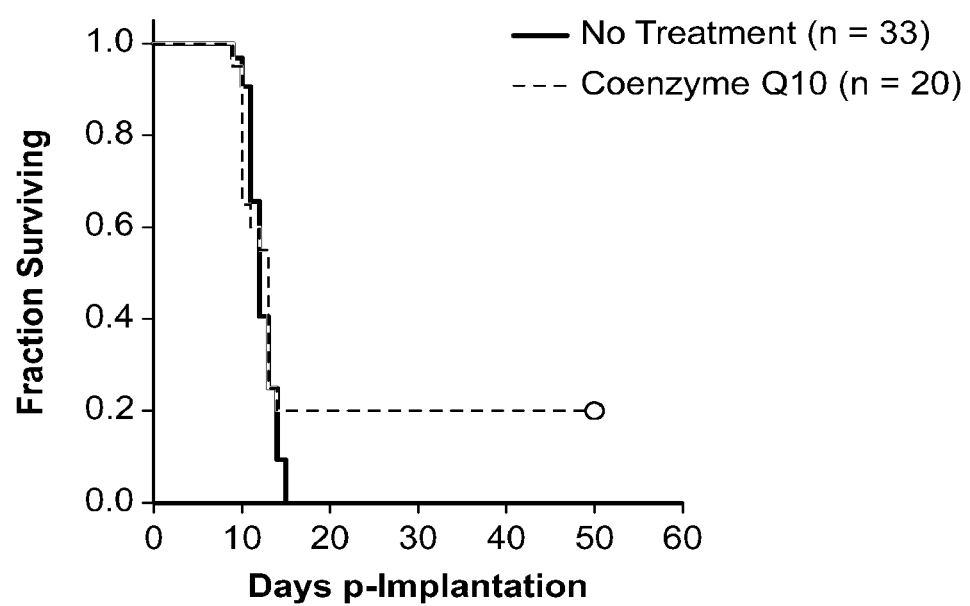
FIG. 8 shows survival rates of rats treated with Coenzyme Q10 by intraperitoneal injection. Rats were treated twice per day with 5, 10, 25 or 50 mg/kg Coenzyme Q10. Coenzyme Q10 treatment was initiated 1 day (n=3), 4 days (n=14), or 8 days (n=3) after implantation of C6 glioma cells. Of the four rats that were alive at Day 50, 1 received 10 mg/kg Coenzyme Q10 and 3 received 50 mg/kg Coenzyme Q10, and treatment was initiated 4 days or 8 days after implantation of C6 glioma cells.

Rat C6 glioma cells were implanted into Sprague-Dawley rats as shown in FIG. 7. The C6 glioma cells develop into a glioma-like tumor. The rats bearing C6 gliomas were treated twice per day with 5, 10, 25 or 50 mg/kg Coenzyme Q10 by intraperitoneal or subcutaneous injection. Coenzyme Q10 treatment was initiated 1 day (n=3), 4 days (n=14), or 8 days (n=3) after implantation of C6 glioma cells. Coenzyme Q10 treatment was continued twice daily until the rat died, or until 34 days after implantation of glioma cells. FIG. 8 shows a summary of survival rates of rats treated with Coenzyme Q10 (n=20) by intraperitoneal injection compared to untreated control rats (n=33). Four of the rats treated with Coenzyme Q10 survived for at least 50 days after implantation of the C6 glioma cells, while none of the untreated control rats survived more than 15 days after implantation. In fact, two of the rats treated with Coenzyme Q10 survived more than 100 days post implantation (see below and FIGS. 9 and 10). Of the four rats that were alive at Day 50, 1 received 10 mg/kg Coenzyme Q10 starting 4 days after implantation, and 3 received 50 mg/kg Coenzyme Q10 starting 4 days or 8 days after implantation.

Figure 9A:
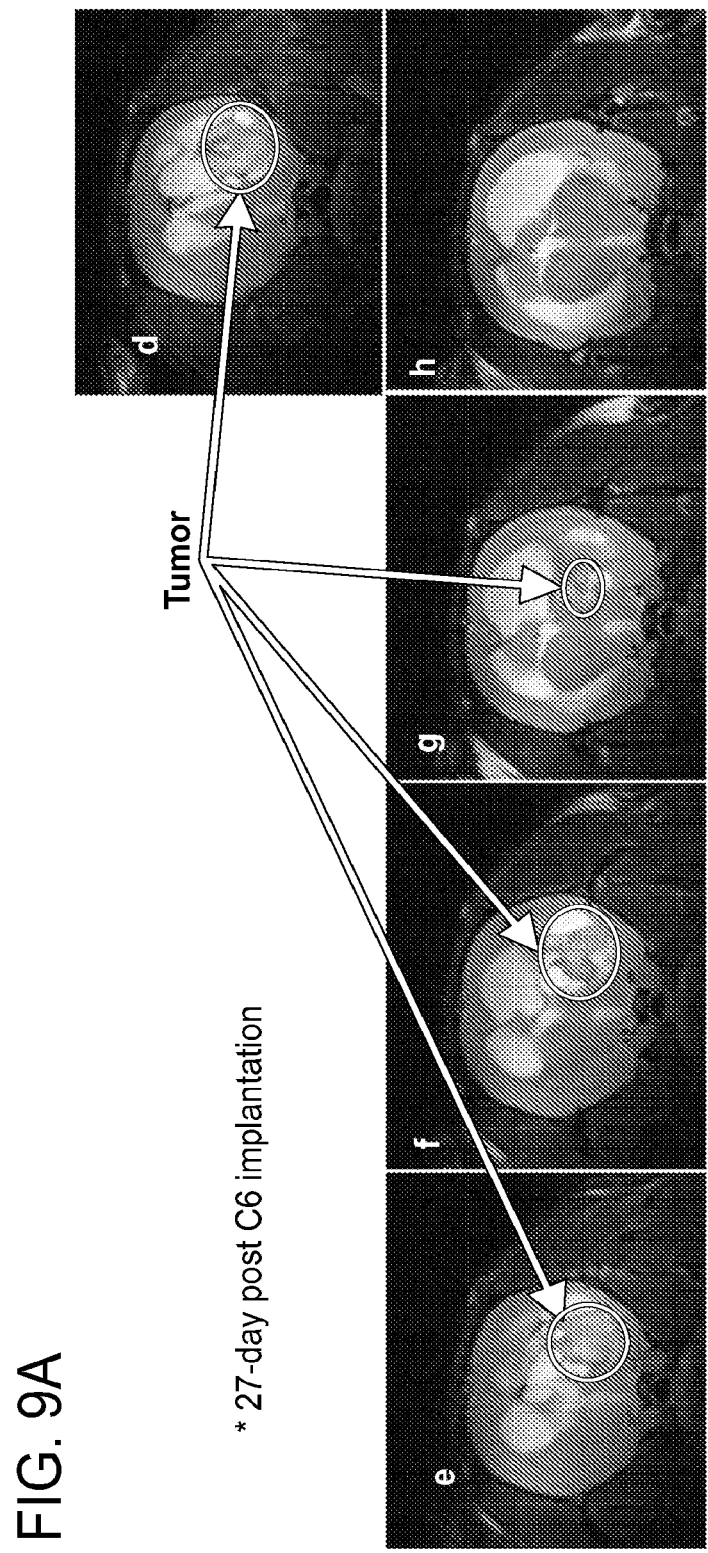
FIGS. 9A, 9B and 9C show serial coronal sections from a C6 implanted rat treated with 10 mg/kg Coenzyme Q10 twice daily by intraperitoneal injection.
Figure 9B:
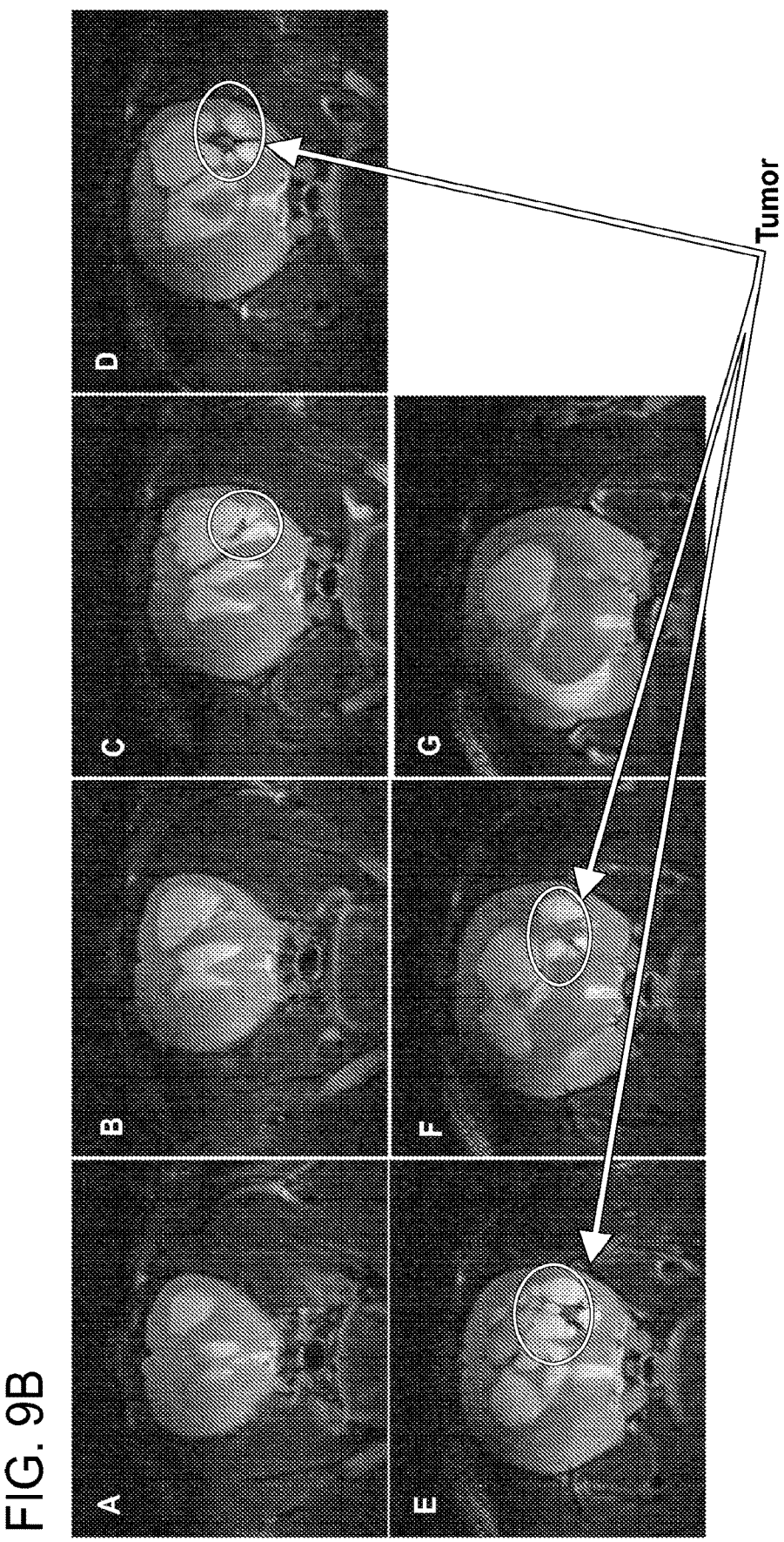
Figure 9C:
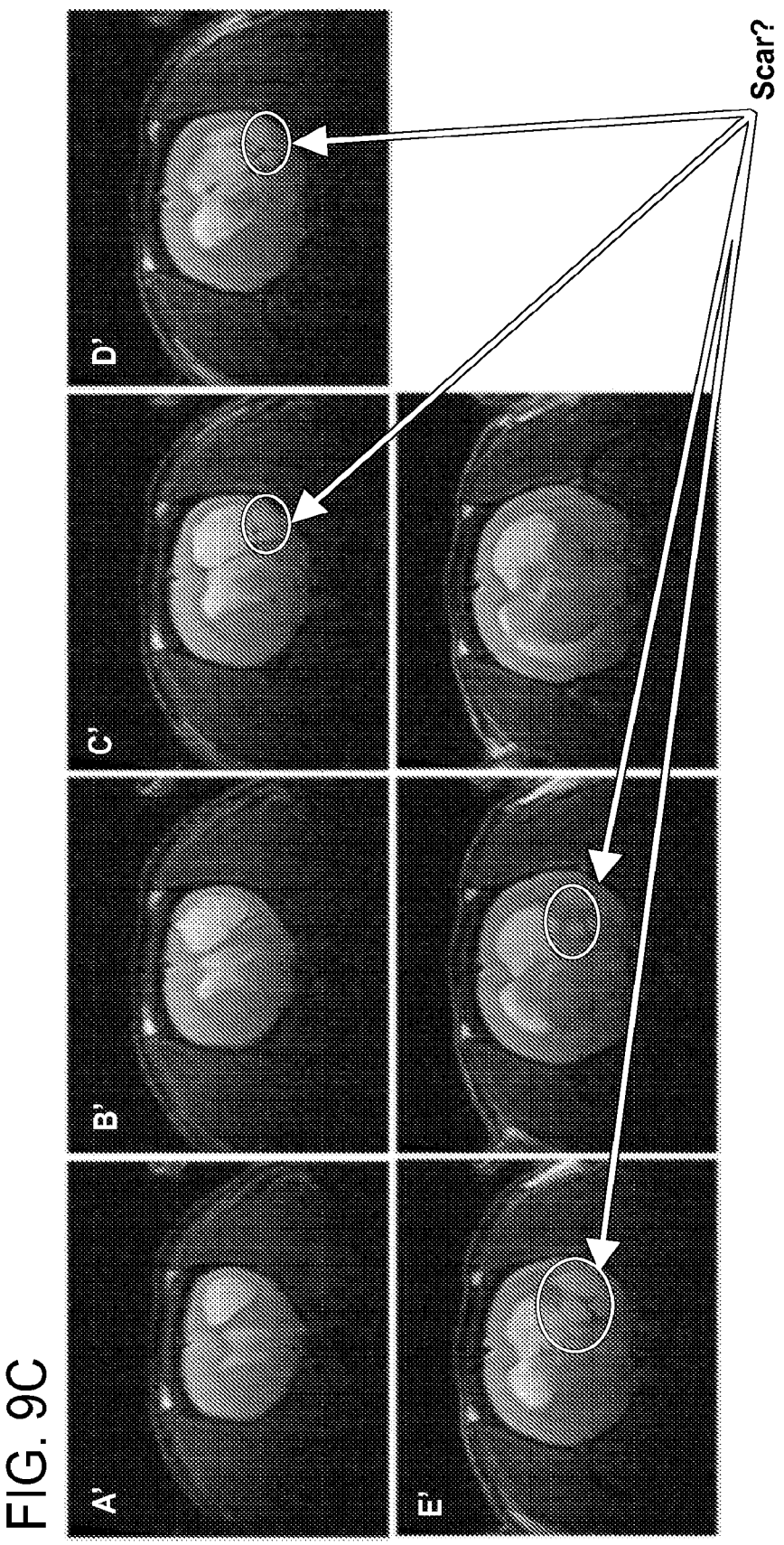
Figure 10A:
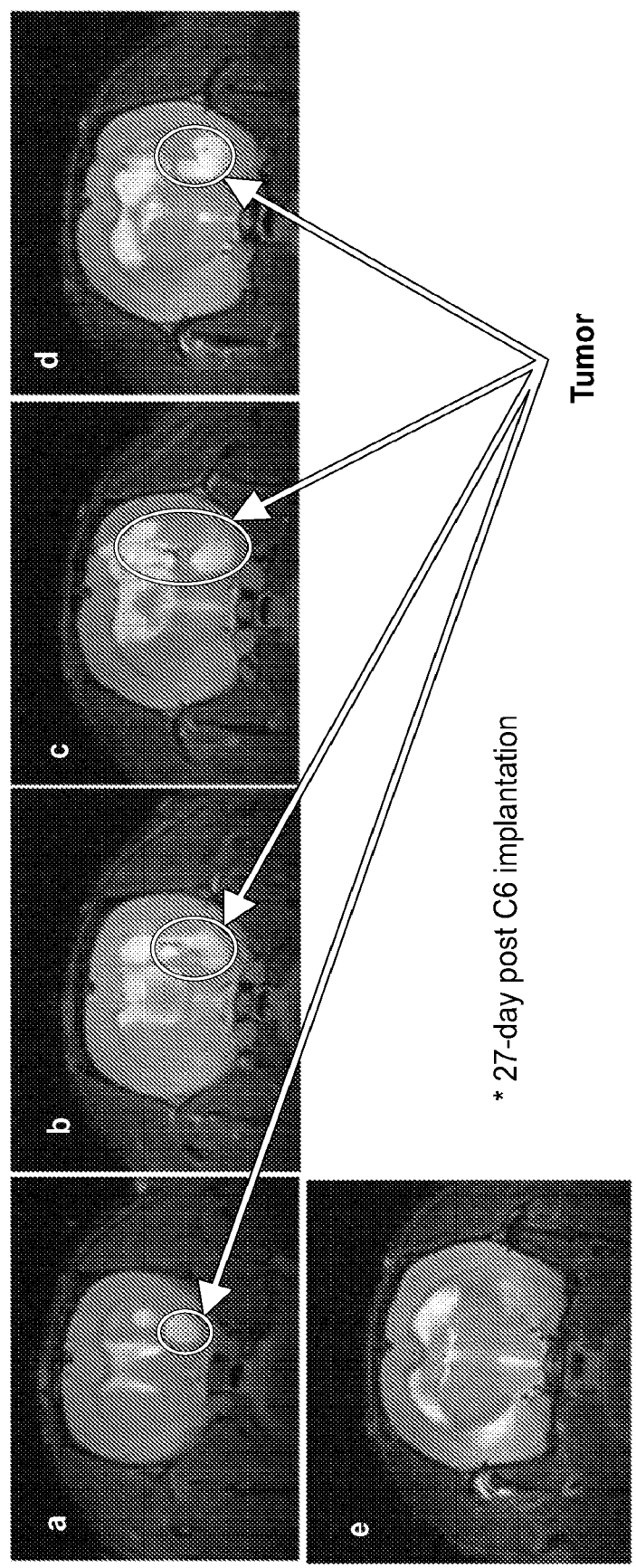
FIGS. 10A, 10B and 10C show serial coronal sections from a C6 implanted rat treated with 50 mg/kg Coenzyme Q10 twice daily by intraperitoneal injection.
Figure 10B:
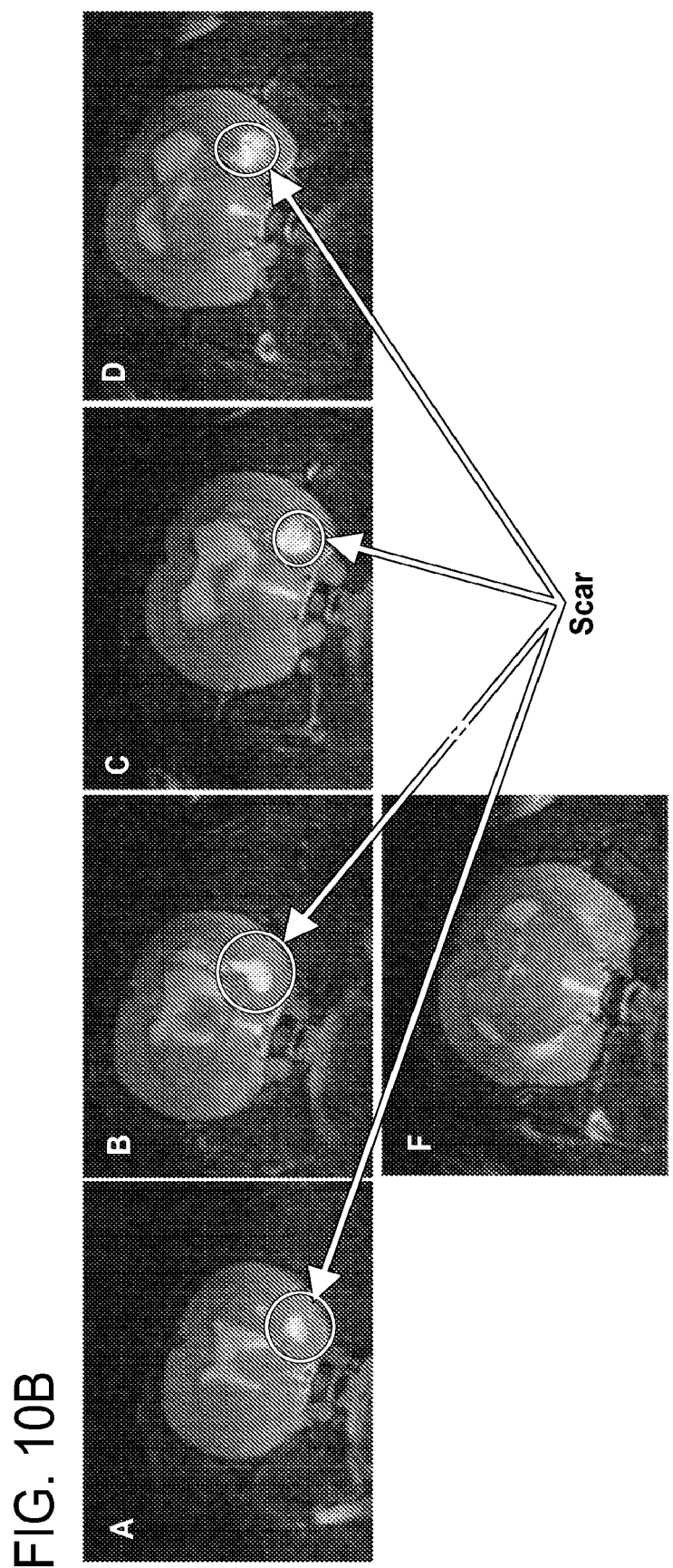
Figure 10C:
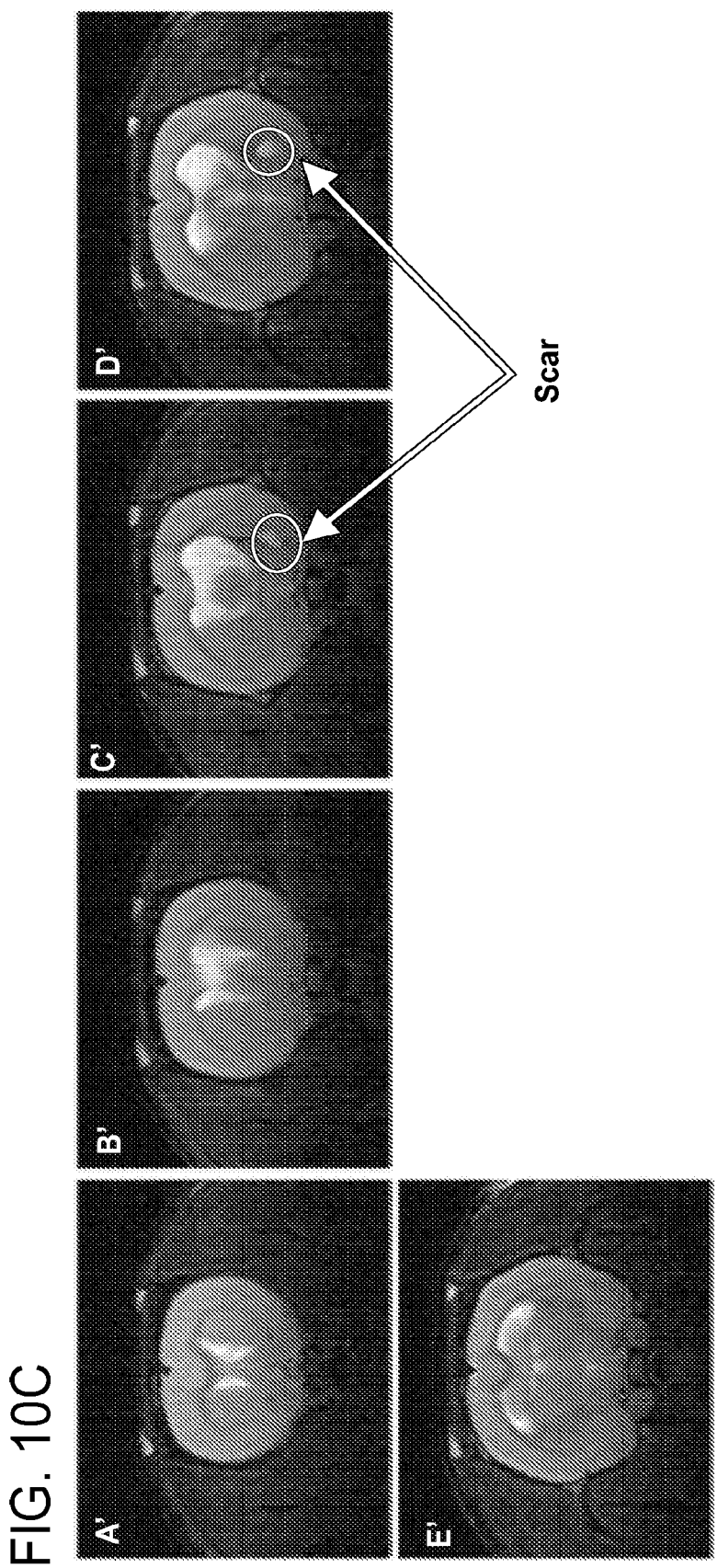

Serial coronal sections from two of the rats that were alive at Day 50 are shown in FIGS. 9 and 10. FIG. 9 shows serial coronal sections from the surviving rat treated with 10 mg/kg Coenzyme Q10 twice daily by intraperitoneal injection starting 4 days after implantation of C6 glioma cells. Enlarged ventricles (hydrocephalus) were present 27 days post C6 implantation (FIG. 9A). At 34 days post-implantation, enlarged ventricles were stilled observed. In addition, there was a complex mass in the tumor area which was not clearly growing (FIG. 9B). Coenzyme Q10 treatment was discontinued at Day 34. At 103 days post-implantation, the rat appeared normal with possible scar tissue in the tumor area (FIG. 9C). FIG. 10 shows coronal sections from a surviving rat treated with 50 mg/kg Coenzyme Q10 twice daily by intraperitoneal injection starting 4 days after implantation of C6 glioma cells. At 27 days post C6 implantation, a complex mass was visible, but it was unclear if this mass represented a tumor or a scar (FIG. 10A). At 34 days post C6 implantation, a scar was visible at the site of implantation and improvement in the overall condition of the rat was observed that was not consistent with tumor growth (FIG. 10B). At 103 days after C6 implantation, a scar was visible at the site of implantation, but the rat was clinically normal (FIG. 10C).

Figure 11:
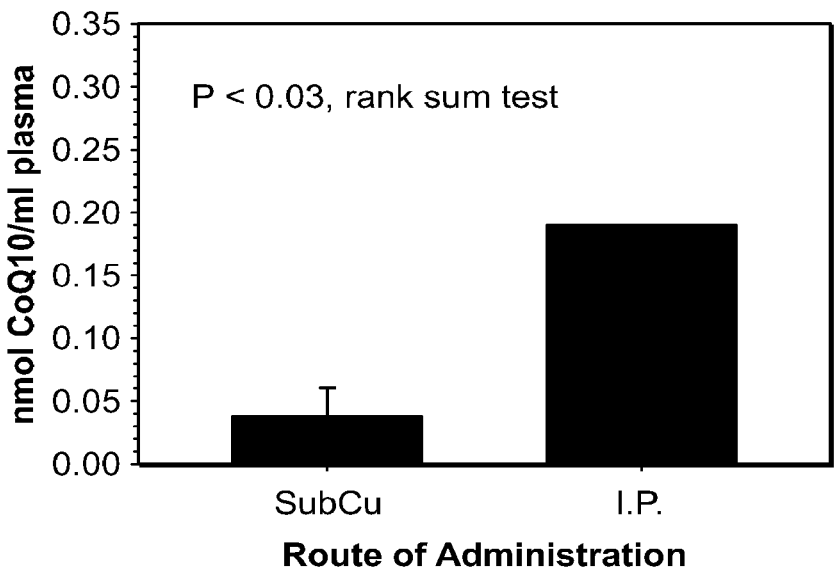
FIG. 11 shows Coenzyme Q10 plasma levels in tumor-bearing rats treated with 50 mg/kg Coenzyme Q10 twice daily by subcutaneous (SubCu) or intraperitoneal (I.P.) injection. Plasma sample was taken 4 days after Coenzyme Q10 treatment was initiated.
Figure 12:
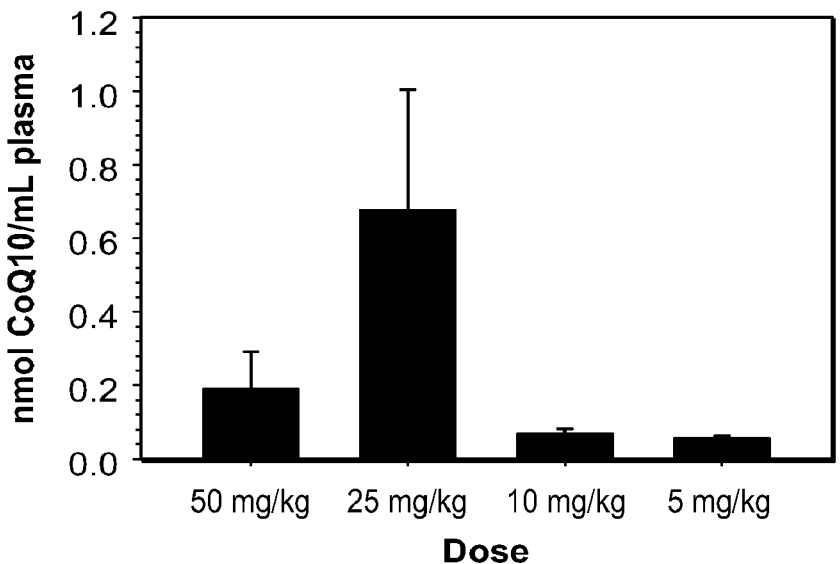
FIG. 12 shows Coenzyme Q10 plasma levels in healthy rats treated with 5, 10, 25 or 50 mg/kg Coenzyme Q10 twice daily. Plasma sample was taken 4 days after Coenzyme Q10 treatment was initiated.

Coenzyme Q10 plasma levels were measured in the rats bearing C6 gliomas four days after Coenzyme Q10 treatment was initiated. Intraperitoneal injection of 50 mg/kg Coenzyme Q10 twice daily resulted in significantly higher Coenzyme Q10 plasma levels compared to the same dose administered by subcutaneous injection. See FIG. 11. For rats administered 5, 10, 25 or 50 mg/kg Coenzyme Q10 twice daily by intraperitoneal injection, the 25 mg/kg dose resulted in the highest Coenzyme Q10 plasma levels four days after Coenzyme Q10 treatment was initiated. See FIG. 12.

These results demonstrate that Coenzyme Q10 is effective in treating gliomas. Furthermore, considering the in vitro results described above demonstrating that increased Complex II activity is associated with increased Coenzyme Q10-mediated cell death, and given that TMZ-resistant glioblastoma exhibits greater Complex II activity, the combined results of the in vitro and in vivo studies described above indicate that Coenzyme Q10 would be especially effective in treating TMZ-resistant glioma.

Example 5: Effects of Coenzyme Q10 on Temozolomide-Resistant and Temozolomide-Sensitive Glioblastoma In Vivo Equal numbers ($1\times10^7$) of human U373 cells left untreated and thus sensitive (TMZ-sensitive) versus TMZ long-term treated (TMZ-resistant) GBM cells (see Calve et al., 2010, Neoplasia 12(9): 727-739, which is incorporated by reference herein in its entirety) are suspended in MATRIGEL® and injected into mice. Tumors are allowed to develop, and treatment is not initiated unless tumors are present.

Mice having tumors are randomized into 4 groups of 30 mice each as follows:
  i. Group 1—No treatment, TMZ-sensitive
  ii. Group 2—No treatment, TMZ-resistant
  iii. Group 3—Intravenous single daily dose of 4% Coenzyme Q10, 50 mg/kg/day, TMZ-sensitive
  iv. Group 4—Intravenous single daily dose of 4% Coenzyme Q10, 50 mg/kg/day, TMZ-resistant Animals are observed for viability and tumor growth is monitored. Animal survival results are collected through day 400. Animals treated with Coenzyme Q10 display significantly increased survival and significantly reduced glioblastoma tumor growth as compared to control (untreated) animals.

Example 6: Effects of Coenzyme Q10 on Temozolomide-Resistant Glioblastoma in Humans The efficacy of Coenzyme Q10 in treating TMZ-resistant glioblastoma is evaluated in humans using Coenzyme Q10 monotherapy and Coenzyme Q10 in combination with chemotherapy. The Coenzyme Q10 is provided as a 4% coenzyme Q10 nanosuspension formulation as described in WO 2011/112900, the entire contents of which are expressly incorporated herein by reference. The study is designed with dosing schedules of a 24-hour infusion, 48-hour infusion, or 96-hour continuous infusion. This extended dosage schedule is intended to decrease Coenzyme Q10 $C_{max}$ values and maintain steady-state levels. Patient survival time and glioblastoma tumor status before, during, and after Coenzyme Q10 treatment is evaluated. Coenzyme Q10 treatment is expected to increase survival time and reduce tumor growth relative to standard chemotherapy. In addition, Coenzyme Q10 in combination with chemotherapy is expected to increase survival time and reduce tumor growth relative to Coenzyme Q10 alone or chemotherapy alone.

Example 7: A Study of Coenzyme Q10 in Combination with Bevacizumab and Temozolomide in Human Patients with Glioblastoma that has Recurred on a Bevacizumab Based Regimen The primary objective of this study is to determine the safety and tolerability of Coenzyme Q10 in combination with temozolomide and bevacizumab in recurrent glioblastoma (GB) patients. The secondary objectives are to determine the effect of the combination of Coenzyme Q10, bevacizumab and temozolomide on overall survival of GB patients from time of recurrence on bevacizumab, and to characterize the pharmacokinetics and pharmacodynamics of the combination of Coenzyme Q10, bevacizumab, and temozolomide.

Coenzyme Q10 Nanosuspension Injection (40 mg/mL) is administered intravenously (IV) over 144 hours (6 days) at the starting dose of 110 mg/kg. Each patient receives 2 consecutive 72-hour (3 day) infusions per week (Tuesday-Friday and Friday-Monday) during each 28-day cycle. Patients concurrently receive bevacizumab (2.5 mg/kg/week) and temozolomide (150 mg/m² for 5 days in a 28 day cycle). The size of the Phase I study is 10 patients and the size of the Phase II study is up to 40 patients.

1. Inclusion Criteria

The inclusion criteria are as follows: (1) Pathologically proven high-grade glioma (WHO III or IV) with an astrocytic component and must be in recurrence after treatment with bevacizumab; (2) Patients must have received conventional radiation therapy of total radiation dosage (ranging from 5400 to 6000 cGy administered in daily fractions of 150 to 200 cGy over 6 weeks, or the equivalent in a hypofractionated protocol) with concurrent temozolomide. Patients must have received bevacizumab and be in recurrence after bevacizumab treatment; (3) Patients must be at least 28 days from last administration of cytotoxic chemotherapy or other investigational agent; (4) Patients must be at least 14 days from the last administration of bevacizumab, but no longer than 48 days from the last administration of bevacizumab; (5) Patients must be >18 years of age; (6) Patients must have a life expectancy >6 weeks; (7) Patients must have a Karnofsky Performance Score (KPS) >60; (8) The patient has adequate organ and marrow function as follows: ANC ≥1500 mm3, platelets ≥100,000/mm3, hemoglobin ≥9 g/dL, serum creatinine ≤1.8 mg/dL or creatinine clearance >50 mL/min, bilirubin ≤1.5 mg/dL; alanine aminotransferase (ALT), aspartate transaminase (AST) ≤2.5 times the upper limit of normal if no liver involvement or ≤5 times the upper limit of normal with liver involvement; (9) The patient has adequate coagulation: prothrombin time (PT) and an International Normalized Ratio, and partial thromboplastin time (PTT)≤1.5 times the upper limit of normal; and (10) Ability to understand and the willingness to sign a written informed consent document.

2. Exclusion Criteria

Patients who meet any of the following criteria will be excluded from trial entry: (1) Patients who have had chemotherapy within 28 days, radiotherapy within 28 days, biological therapy within 14 days, and investigational therapy within 28 days prior to first dose of experimental drug. (2) Patients with the following co-morbid disease or incurrent illness: active heart disease including myocardial infarction within previous 3 months, symptomatic coronary artery disease, arrhythmias not controlled by medication, unstable angina pectoris, or uncontrolled congestive heart failure (NYHA class III and IV); uncontrolled or severe coagulopathies or a history of clinically significant bleeding within the past 6 months, such as hemoptysis, epistaxis, hematochezia, hematuria, or gastrointestinal bleeding; known predisposition for bleeding such as von Willebrand's disease or other such condition; the patient has uncontrolled concurrent illness including, but not limited to uncontrolled infection, symptomatic congestive heart failure (NYHA class III and IV), uncontrolled cardiac arrhythmia, or psychiatric illness/social situations that would limit compliance with study requirements; prior malignancy except for non-melanoma skin cancer and carcinoma in situ (of the cervix or bladder), unless diagnosed and definitively treated more than 3 years prior to first dose of investigational drug. (3) Is receiving any of the following medications: therapeutic doses of any anticoagulant, including LMWH. Concomitant use of warfarin, even at prophylactic doses, is prohibited; digoxin, digitoxin, lanatoside C or any type of *digitalis* alkaloids; colony stimulating factors (CSFs) that cannot be held during the monitoring period for dose-limiting toxicities (DLT); other investigational, chemotherapeutic, or biologic anti-cancer agents (within 28 days prior to first dose for all drugs other than BEV, which the patient may have received within 14 days of first dose). (4) The patient has significant unresolved toxicities from prior treatment that have not resolved or stabilized. (5) Known allergy to Coenzyme Q10. (6) Pregnant or lactating patients will not be enrolled. BEV is contraindicated in pregnancy. (7) The patient is known to be positive for the human immunodeficiency virus (HIV). The effect of Coenzyme Q10 on HIV medications is unknown and could lead to under or overdosing of these medications. Note: HIV testing is not required for eligibility, but if performed previously and was positive, the patient is ineligible for the study.

3. Patient Screening and Safety Assessment

The following procedures are performed for all potential subjects at the screening visit conducted within 14 days prior to the first dose of Coenzyme Q10: serum pregnancy test, laboratory tests, including chemistry, hematology, and coagulation parameters, urinalysis, MRI of the brain with and without contrast demonstrating progressive high grade glioma after therapy with bevacizumab, PET scan (≤2 weeks of first Coenzyme Q10 dose), Vitamin K level, Lipids, CRP. If screening evaluations are performed >7 days before the first dose of Coenzyme Q10, the following evaluations are repeated on Cycle 1, Day 1: Physical examination, Weight, Vital signs (5-minute sitting blood pressure, pulse, respiratory rate, oral temperature), CBC, PT/PTT/INR and platelets, Serum chemistry panel, including CMP and serum lipids, Urinalysis Pregnancy test (urine or serum) in women of childbearing potential, Concomitant medications. Safety assessments are performed weekly for Coenzyme Q10.

Prophylactic Vitamin K is given to all patients prior to the beginning of each week of therapy, unless contraindicated as determined by the Investigator. At each dose level, patients in the phase I portion are treated for 6 hours under observation during Cycle 1. PK and PD data is only collected for patients in the phase I portion of the study The following assessments are performed during Cycle 1 (within ±3 days unless noted otherwise): Day 1: Physical examination and weight; Day 1 and 2: ECG pre-dose and at 24 (+/−2 Hours) hours post start of infusion (90% of $C_{max}$); Days 1, 8, 15, and 22: Concomitant medications reviewed. Hematology, serum chemistry panel [including CMP and serum lipids], PT/PTT/INR and platelets and urinalysis ≤24-72 hours prior to each Tuesday dose (once a week). Patients should not be dosed until those are within normal limits or have returned to grade 1 or resolved from previous elevations with the exception of PT/PTT/INR which must be <1.5×ULN. See Table 4.0; Days 1 and 15: BEV infusion; Day 21: ECG before patient is discharged; Day 25: C-Reactive Protein; Days 1, 4, 8, 11, 15, 18, 22, and 25 Vital signs prior to each pump refill, 1-hr (+/−15 minutes) post start of infusion and prior to discharge. Assess for Adverse Events prior to start of infusion and prior to discharge on day 1. On all other days, assess for Adverse Events before patient is discharged. PT/PTT/INR and platelets ≤24-72 hours prior to each pump refill. As needed: Laboratory testing for any ≥grade 2 prolonged INR to determine the underlying cause. The workup should include: LFTs, levels of vitamin-K dependent coagulation factors (II, VII, IX, X), Protein C, and Protein S. If ≥grade 2 INR is not corrected following administration of Vitamin K, additional tests such as mixing studies, fibrinogen level, D-dimer and fibrin split products should be performed. PK blood and urine samples in phase I patients (see schedule in Section 8.1). PD blood and urine samples in phase I patients (see schedule in Section 8.1).

The following assessments are performed during Cycle 2 (within ±3 days unless noted otherwise): Day 1: Physical examination, weight, KPS performance status; Days 1-5: Oral temozolomide (150 mg/m²) nightly; Days 1, 8, 15, and 22: Concomitant medications reviewed. Hematology, serum chemistry panel [including CMP and serum lipids], PT/PTT/INR, platelets and urinalysis ≤24-72 hours prior to each Monday dose (weekly). Patients should not be dosed until those are within normal limits or have returned to grade 1 or resolved from previous elevations with the exception of PT/PTT/INR which must be <1.5×UNL; Day 25: C-Reactive Protein; Days 1, 4, 8, 11, 15, 18 22, and 25: Vital signs prior to each pump refill, 1-hr (+/−15 minutes) post start of infusion and prior to discharge. Assess for Adverse Events prior to start of infusion and prior to discharge on day 1. On all other days, assess for Adverse Events before patient is discharged. PT/PTT/INR and platelets ≤24-72 hours prior to each pump refill. As needed: Laboratory testing for any ≥grade 2 prolonged INR to determine the underlying cause. The workup should include: LFTs, levels of vitamin-K dependent coagulation factors (II, VII, IX, X), Protein C, and Protein S. If ≥grade 2 INR is not corrected following administration of Vitamin K, cryoprecipitate or fresh frozen plasma, additional tests such as mixing studies, fibrinogen level, D-dimer and fibrin split products should be performed. Days 1 and 15: BEV infusion; Per Standard of Care (roughly every 2 cycles): If the patient is receiving MRI for evaluation, tumor response assessment by RANO is recorded. Days 1, 15 and 22: PK and PD blood samples Day 28 (+/−2 weeks): PET-CT Brain; PK blood and urine samples in phase I patients. PD blood and urine samples in phase I patients.

The following assessments are performed during Cycles 3-12 (within ±3 days unless noted otherwise): Day 1: Physical examination, weight, KPS performance status; Days 1-5: Oral temozolomide (150 mg/m²) nightly; Days 1, 8, 15, and 22: Concomitant medications reviewed. Hematology, serum chemistry panel [including CMP and serum lipids], PT/PTT/INR, platelets and urinalysis ≤24-72 hours prior to each Monday dose (weekly). Patients should not be dosed until those are within normal limits or have returned to grade 1 or resolved from previous elevations with the exception of PT/PTT/INR which must be <1.5×UNL. Day 25: C-Reactive Protein; Days 1, 4, 8, 11, 15, 18 22, and 25: Vital signs prior to each pump refill, 1-hr (+/−15 minutes) post start of infusion and prior to discharge. Assess for Adverse Events prior to start of infusion and prior to discharge on day 1. On all other days, assess for Adverse Events before patient is discharged. PT/PTT/INR and platelets ≤24-72 hours prior to each pump refill. As needed: Laboratory testing for any ≥grade 2 prolonged INR to determine the underlying cause. The workup should include: LFTs, levels of vitamin-K dependent coagulation factors (II, VII, IX, X), Protein C, and Protein S. If ≥grade 2 INR is not corrected following administration of Vitamin K, cryoprecipitate or fresh frozen plasma, additional tests such as mixing studies, fibrinogen level, D-dimer and fibrin split products should be performed. Days 1 and 15: BEV infusion; Per Standard of Care (roughly every 2 cycles): If the patient is receiving MRI for evaluation, tumor response assessment by RANO will be recorded; Days 1, 15 and 22: PK and PD blood samples in phase I patients (see schedule in Section 8.1).

The following end of treatment assessments are performed 30 days (±5 days) after the last dose of Coenzyme Q10 but may occur earlier if requested by the investigator: Physical examination, Weight, Vital signs, ECG, KPS, Hematology, PT/PTT/INR and platelets, Serum chemistry panel (including CMP and serum lipids), C-Reactive Protein, Urinalysis, Tumor assessment, Concomitant medications, Adverse events. All patients who come off study will be followed every 3 months for overall survival. Blood and urine samples for hematology, coagulation, serum chemistry, and urinalysis are prepared using standard procedures.

| | |
|---|---|
| Hematology | CBC with differential, platelets |
| Coagulation | PT/PTT/INR (Screening only: Vitamin K) |
| Serum Chemistry | Albumin, alkaline phosphatase, ALT, AST, blood urea nitrogen (BUN), calcium, carbon dioxide, chloride, creatinine, gamma-glutamyl transferase (GGT), glucose, lactate dehydrogenase, phosphorus, potassium, sodium, total bilirubin, total protein, serum magnesium, cholesterol, triglycerides |
| Urinalysis | Appearance, color, pH, specific gravity, ketones, protein, glucose, bilirubin, nitrite, urobilinogen, and occult blood (microscopic examination of sediment will be performed only if the results of the urinalysis dipstick evaluation are positive) |
| Laboratory work-up for any ≥ grade 2 INR | LFTs, levels of Vitamin-K dependent coagulation factors (II, VII, IX, X), Protein C, and Protein S. If ≥ grade 2 INR is not corrected following administration of Vitamin K, cryoprecipitate or fresh frozen plasma, additional tests such as mixing studies, fibrinogen level, D-dimer and fibrin split products should be performed. |

4. Preparation and Administration of Coenzyme Q10

Coenzyme Q10 (Ubidecarenone, USP) Nanosuspension Injection, 40 mg/mL, is a sterile aqueous colloidal dispersion of nanoparticles of the active drug, Ubidecarenone USP (Coenzyme Q10). The investigational drug product for use in clinical trials is a 4% (w/v) sterile Coenzyme Q10 aqueous nanosuspension. It is intended to deliver a high dose of the active drug, Coenzyme Q10 (Ubidecarenone: 800 mg [20 mL] to 4000 mg [100 mL]) undiluted when administered as a single, slow 72-hour IV infusion. The drug product is produced using a microfluidization process which results in a stable nanosuspension with a mean particle size of 30 to 80 nm. The nanosuspension formulation consists of 40 mg/mL (36.0 to 44.0 mg/mL) Coenzyme Q10.

TABLE 10

Properties of Coenzyme Q10

| | |
|---|---|
| Chemical Name | 2-(3,7,11,15,19,23,27,31,35,39-decamethyltetra-conta-2,6,10,14,18,22,26,30,34,38-decaenyl)-5,6-dimethoxy-3-methyl-cyclohexa-2,5-diene-1,4-dione |
| INN Name | 2-[(2E,6E,10E,14E,18E,22E,26E,30E,34E)-3,7,11,15,19,23,27,31,35,39-decamethyltetra-conta-2,6,10,14,18,22,26,30,34,38-decaenyl]-5,6-dimethoxy-3-methylbenzene-1,4-dione |
| Alternate Names | Coenzyme Q10 is also known as ubiquinone, CoQ10, Q10 and Ubidecarenone |
| Active Ingredient | Ubidecarenone, USP |
| CAS Number | 303-98-0 |
| Molecular Formula | $C_{59}H_{90}O_4$ |
| Molecular Weight | 863.35 g |

Coenzyme Q10 is administered as a continuous IV infusion over 72 hours twice weekly of each 28-day cycle administered until unacceptable toxicity, withdrawal from study or death. Patients also receive bevacizumab (BEV) every 2 weeks and temozolomide (TMZ) every 4 weeks. Bevacizumab is a human monoclonal antibody to vascular endothelial growth factor (VEGF). Temozolomide is an oral alkylating chemotherapy. Coenzyme Q10 is supplied as a translucent to cloudy red-orange nanosuspension packaged in a 20 mL or 100 mL single-use clear glass vial, sealed with a chlorobutyl rubber stopper and an aluminum overcap. Each vial of drug product is supplied with a sterile syringe filter. The concentration of the sterile drug product is 40 mg/mL.

| Composition of Sterile Coenzyme Q10 Nanosuspension Injection (40 mg/mL) | | | |
|---|---|---|---|
| Ingredient | Vial Volume | Concentration | API Theoretical Quantity per vial |
| Coenzyme Q10 | 20 mL | 40 mg/mL | 800 mg |
| Coenzyme Q10 | 100 mL | 40 mg/mL | 4000 mg |

The volume of each dose of Coenzyme Q10 (40 mg/mL) is based on the patient's weight in kilograms and on cohort assignment. Instructions for preparing undiluted Coenzyme Q10 drug product for administration as a single 72-hour continuous infusion are as follows. Determine the total number of 20 mL (40 mg/mL; 800 mg) and 100 mL (40 mg/mL; 4000 mg) single-use vials that are needed for the patient dose and the capacity of the sterile empty IV bag that is needed (100 mL, 250 mL, or 500 mL). Gently agitate the vials by inversion until any suspended flocculants are no longer visible and drug suspension is uniform.

Accurately withdraw the required volume of drug product from the required number of 20 mL or 100 mL vials using sterile aseptic technique within a laminar flow hood or equivalent environment. Remove the overcap from the vials containing the drug product. Fit a needle to a 50 mL syringe and insert the needle through the septum into the vial and withdraw the required amount of product volume from the 20 mL or 100 mL vials. Fit a 5 µm syringe filter (supplied with each 20 mL and 100 mL vial) onto the syringe and then fit a new needle onto the syringe filter. Push the needle into the infusion bag and apply gentle pressure to the plunger to filter the product into the infusion bag. Repeat steps 2 through 6 until the total volume of the required dose has been loaded into the infusion bag. Discard any unused contents of the vials. Immediately before administration, mix the drug product contents of the infusion bag by manually inverting the filled IV bag back and forth several times to insure a homogeneous product prior to the infusion. The translucent to cloudy orange drug product is infused as a single, continuous 72-hour infusion with the IV set supplied.

Administration of Coenzyme Q10 to outpatients must be via a central line (MediPort) or peripherally inserted central catheter (PICC) line. The IV bags must be protected from UV light during each 72-hour infusion if a cassette and cassette pouch holder is not used with the pump provided.

For the first dose of each week, a loading dose (approximately 8.2% of the total volume) is infused over 1 hour with the remainder of the dose volume infused over 71 hours. At each dose level of Arm 1 and Arm 2, patients are treated for either 8 hours at minimum of outpatient monitoring or inpatient monitoring for the first 24-hrs of the first infusion of Cycle 1.

| Coenzyme Q10 Nanosuspension Injection Dose Cohorts | | | | |
|---|---|---|---|---|
| | Dose 1 (Tuesday) | | | |
| Cohort | Total Coenzyme Q10 Dose per 72 hr infusion (2X per week) | Loading Dose to be Infused over 1 Hour (8.2% of dose) | Remainder to be Infused Over 71 hr. | Dose 2 (Friday) | Total Coenzyme Q10 Dose per week |
| −1 | 50 mg/kg | 4.1 mg/kg | 45.9 mg/kg | 50 mg/kg | 100 mg/kg |
| 1 | 66 mg/kg | 5.4 mg/kg | 60.6 mg/kg | 66 mg/kg | 132 mg/kg |
| 2 | 88 mg/kg | 7.2 mg/kg | 80.8 mg/kg | 88 mg/kg | 176 mg/kg |
| 3 | 110 mg/kg | 9.0 mg/kg | 101.0 mg/kg | 110 mg/kg | 220 mg/kg |
| 4 | 137 mg/kg | 11.2 mg/kg | 125.8 mg/kg | 137 mg/kg | 274 mg/kg |
| 5 | 171 mg/kg | 14.0 mg/kg | 157.0 mg/kg | 171 mg/kg | 342 mg/kg |
| 6 | 215 mg/kg | 17.6 mg/kg | 197.4 mg/kg | 215 mg/kg | 430 mg/kg |
| 7 | 286 mg/kg | 23.4 mg/kg | 262.6 mg/kg | 286 mg/kg | 572 mg/kg |
| 8 | 380 mg/kg | 31.2 mg/kg | 348.8 mg/kg | 380 mg/kg | 760 mg/kg |
| 9 | 505 mg/kg | 41.4 mg/kg | 463.6 mg/kg | 505 mg/kg | 1010 mg/kg |
| 10 | 672 mg/kg | 55.1 mg/kg | 616.9 mg/kg | 672 mg/kg | 1344 mg/kg |

All AEs are assessed according to the NCI-CTCAE version 4.03. In the event of multiple toxicities, dose delays and modifications should occur in accordance with the worst toxicity observed. If the patient fails to meet the criteria for re-treatment, treatment may be delayed, followed by an additional evaluation to determine feasibility of retreatment.

The dose of Coenzyme Q10, defined as a 72-hour infusion, may be interrupted due to Coenzyme Q10 related clinically significant toxicity. No Coenzyme Q10 dose reductions are allowed during Cycle 1 or 2. No more than 6 doses may be missed during Cycle 1 & 2. If any of these situations were to occur, the patient must be withdrawn from study.

5. Dose Reduction During Cycles 3-12
Hematologic Toxicity

The Baseline Laboratory Requirements are ANC ≥1500 mm$^3$, platelets ≥100,000/mm$^3$, hemoglobin ≥9 g/dL and INR ≤1.5×UNL. Hematology and chemistry should be assessed weekly and coagulation should be repeated within 24-72 hours prior to initiation of each dose. Coenzyme Q10 must be held for any grade 3 or 4 hematologic toxicity that is at least possibly drug-related. Any grade 3 or 4 hematologic toxicity must return to a grade 1 or resolved with the exception of INR which must be ≤1.5×UNL prior to administration of Coenzyme Q10 in Cycles 3-12. Coenzyme Q10 may be resumed at a reduced dose.

To monitor and mitigate Coenzyme Q10-associated coagulopathies, PT, PTT, INR and platelet count must be assessed prior to administering each dose of Coenzyme Q10. Prophylactic Vitamin K is given to all patients prior to the beginning of every week of therapy, unless contraindicated as determined by the Investigator. An INR value of ≥grade 2 requires immediate treatment with Vitamin K, cryoprecipitate or fresh frozen plasma as clinically indicated. Any AE must decrease to ≤grade 1 and the INR must be ≤1.5×UNL before resuming Coenzyme Q10 treatment.

If a second adverse event of ≥grade 3 INR elevations occurs, permanently discontinue Coenzyme Q10. Permanently discontinue Coenzyme Q10 in patients who experience clinically significant bleeding in conjunction with a ≥grade 2 elevation in INR.

Non Hematologic Toxicity

A grade 3 or 4 non-hematologic toxicity that is at least possibly drug-related must return to grade 1 or resolve prior to administration of Coenzyme Q10 in Cycles 3-12. Coenzyme Q10 may be resumed at a reduced dose. Grade 3 fasting lipid abnormalities are an exception in the absence of clinical signs or symptoms. Coenzyme Q10 causes a false positive fasting lipid elevation. Abnormal fasting lipid profiles should be monitored closely however Coenzyme Q10 may continue in the absence of clinical signs or symptoms. Patients with toxicities that are manageable with supportive therapy may not require dose reductions. Patients requiring greater than 2 dose reductions of Coenzyme Q10 should be withdrawn from the study.

The invention claimed is:

1. A method of treating a glioma in a subject, the method comprising administering to the subject;
    a) a composition comprising a Coenzyme Q10 compound; and
    b) temozolomide (TMZ), thereby treating the glioma in the subject, wherein the composition comprising the Coenzyme Q10 compound is administered by injection or infusion.

2. The method of claim 1, wherein the glioma is a glioblastoma.

3. The method of claim 1, wherein the glioma is a refractory glioma.

4. The method of claim 3, wherein the glioma is refractory to an anti-cancer agent selected from the group consisting of temozolomide (TMZ) and bevacizumab.

5. The method of claim 1, wherein the subject has failed treatment for the glioma with bevacizumab.

6. The method of claim 1, wherein the subject demonstrates a clinical benefit as a result of administration of the composition comprising the Coenzyme Q10 compound.

7. The method of claim 6, wherein the clinical benefit is selected from the group consisting of stable disease per RECIST 1.1 criteria, partial response per RECIST 1.1 criteria, and complete response per RECIST 1.1 criteria.

8. The method of claim 1, wherein the glioma comprises a Stage IV tumor.

9. The method of claim 1, wherein the glioma is a low grade glioma.

10. The method of claim 1, wherein the glioma is a high grade glioma.

11. The method of claim 1, wherein the glioma is metastatic.

12. The method of claim 5, wherein the subject has further failed treatment with a chemotherapeutic agent selected from the group consisting of carmustine (BCNU), thalidomide, irinotecan, lomustine (CCNU), procarbazine, vincristine, and a platinum compound.

13. The method of claim 1, wherein the Coenzyme Q10 compound is Coenzyme Q10.

14. The method of claim 13, wherein the Coenzyme Q10 is administered at a dose selected from the group consisting of at least 50 mg/kg/dose, at least 66 mg/kg/dose, at least 88 mg/kg/dose, at least 110 mg/kg/dose, at least 137 mg/kg/dose, at least 171 mg/kg/dose, at least 215 mg/kg/dose, at least 286 mg/kg/dose, at least 380 mg/kg/dose, at least 505 mg/kg/dose, and at least 672 mg/kg/dose.

15. The method of claim 1, wherein the composition comprising the Coenzyme Q10 compound is administered intravenously.

16. The method of claim 1, wherein the composition comprising the Coenzyme Q10 is administered by continuous infusion.

17. The method of claim 16, wherein the composition comprising the Coenzyme Q10 is administered by continuous infusion for at least 48 hours, at least 72 hours, at least 96 hours, at least 120 hours, or at least 144 hours.

18. The method of claim 1, wherein the subject is human.

19. The method of claim 1, wherein the method further comprises administering an additional anti-cancer agent to the subject.

20. The method of claim 19, wherein the additional anti-cancer agent is bevacizumab.

21. The method of claim 1, wherein the method further comprises administering radiation to the subject.

* * * * *